US011220545B2

United States Patent
Freeman et al.

(10) Patent No.: US 11,220,545 B2
(45) Date of Patent: Jan. 11, 2022

(54) METHODS FOR UPREGULATING IMMUNE RESPONSES USING COMBINATIONS OF ANTI-RGMB AND ANTI-PD-1 AGENTS

(71) Applicant: Dana-Farber Cancer Institute, Inc., Boston, MA (US)

(72) Inventors: Gordon J. Freeman, Brookline, MA (US); Yanping Xiao, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 1047 days.

(21) Appl. No.: 15/533,532

(22) PCT Filed: Dec. 7, 2015

(86) PCT No.: PCT/US2015/064203
§ 371 (c)(1),
(2) Date: Mar. 21, 2018

(87) PCT Pub. No.: WO2016/094273
PCT Pub. Date: Jun. 16, 2016

(65) Prior Publication Data
US 2018/0002422 A1     Jan. 4, 2018

Related U.S. Application Data

(60) Provisional application No. 62/088,855, filed on Dec. 8, 2014.

(51) Int. Cl.
| | |
|---|---|
| C07K 16/28 | (2006.01) |
| A61K 39/395 | (2006.01) |
| A61K 31/7088 | (2006.01) |
| A61K 45/06 | (2006.01) |
| C12N 15/113 | (2010.01) |
| A61K 39/00 | (2006.01) |

(52) U.S. Cl.
CPC ...... *C07K 16/2818* (2013.01); *A61K 31/7088* (2013.01); *A61K 39/39541* (2013.01); *A61K 45/06* (2013.01); *C07K 16/28* (2013.01); *C12N 15/1138* (2013.01); *A61K 2039/505* (2013.01); *A61K 2039/507* (2013.01); *C07K 2317/31* (2013.01); *C07K 2317/76* (2013.01); *C12N 2310/11* (2013.01); *C12N 2310/14* (2013.01); *C12N 2310/16* (2013.01); *C12N 2320/31* (2013.01)

(58) Field of Classification Search
None
See application file for complete search history.

(56) References Cited

U.S. PATENT DOCUMENTS

| | | | | |
|---|---|---|---|---|
| 7,595,048 | B2 * | 9/2009 | Honjo | A61P 37/04 424/142.1 |
| 9,845,356 | B2 * | 12/2017 | Freeman | A61P 29/00 |
| 10,093,734 | B2 * | 10/2018 | Meyer | C07K 16/22 |
| 10,457,733 | B2 * | 10/2019 | Freeman | G01N 33/6872 |
| 2006/0063208 | A1 * | 3/2006 | Woolf | C12N 15/113 435/7.2 |
| 2008/0118511 | A1 * | 5/2008 | Freeman | A61P 35/00 424/139.1 |
| 2009/0217401 | A1 * | 8/2009 | Korman | A61K 51/10 800/18 |
| 2010/0040614 | A1 * | 2/2010 | Ahmed | A61P 33/00 424/133.1 |
| 2010/0055102 | A1 | 3/2010 | Langermann | |
| 2010/0151492 | A1 | 6/2010 | Ahmed et al. | |
| 2011/0195068 | A1 * | 8/2011 | Langermann | A61P 31/14 424/133.1 |
| 2015/0197571 | A1 * | 7/2015 | Freeman | A61P 5/14 424/136.1 |
| 2015/0299322 | A1 * | 10/2015 | Freeman | G01N 33/5047 424/134.1 |

FOREIGN PATENT DOCUMENTS

| | | |
|---|---|---|
| WO | WO-2014/022759 A1 | 2/2014 |

OTHER PUBLICATIONS

Huang Z. Pharmacology and Therapeutics, 2000, 86: 201-215.*
Nguen et al. (2015) Nature Reviews Immunology 15: 45-56.*
International Search Report and Written Opinion for International Application No. PCT/US15/64203 dated Mar. 11, 2016.
Extended European Search Report issued by the European Patent Office in corresponding Application No. 15867409.3, dated Apr. 26, 2018.
Liang et al., "Regulation of PD-1, PD-L1, and PD-L2 expression during normal and autoimmune responses," Eur J Immunol, 33(10):2706-2716 (2003).
Xiao et al., "RGMb is a novel binding partner for PD-L2 and its engagement with PD-L2 promotes respiratory tolerance," J Exp Med, 211(5):943-959 (2014).

* cited by examiner

*Primary Examiner* — Ilia I Ouspenski
(74) *Attorney, Agent, or Firm* — Foley Hoag LLP

(57) ABSTRACT

The present invention relates to methods for upregulating immune responses using combinations of anti-RGMb and anti-PD-1 agents.

13 Claims, 7 Drawing Sheets

Specification includes a Sequence Listing.

METHODS FOR UPREGULATING IMMUNE RESPONSES USING COMBINATIONS OF ANTI-RGMB AND ANTI-PD-1 AGENTS

CROSS-REFERENCE TO RELATED APPLICATIONS

This application claims the benefit of U.S. Provisional Application No. 62/088,855, filed on 8 Dec. 2014; the entire contents of said application are incorporated herein in their entirety by this reference.

STATEMENT OF RIGHTS

This invention was made with government support under Grants P01 AI056299, U54CA163125, P50CA101942, and HHSN272201100018C awarded by the National Institutes of Health. The U.S. government has certain rights in the invention. This statement is included solely to comply with 37 C.F.R. § 401.14(a)(f)(4) and should not be taken as an assertion or admission that the application discloses and/or claims only one invention.

BACKGROUND OF THE INVENTION

Immune checkpoints, such as CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, HHLA2, butyrophilins, A2aR and many more, negatively regulate immune response progression based on complex and combinatorial interactions between numerous inputs. Different Immune checkpoints act m different contexts to suppress immune responses in different disorders, such that interfering with any specific immune checkpoint may not significantly alter an immunological response to a specific disorder. While some progress has been made to determine which interventions at which particular nodes of the immune checkpoint regulatory system can be targeted for benefiting the treatment of disorders for which an increased immunological response is desired, it is not currently possible to identify specific interactions having significant, such as synergistic, anti-cancer therapeutic efficacy. Accordingly, there is a great need in the art to define specific combinations of immune checkpoints useful for treating disorders that would benefit from increased immunological responses.

SUMMARY OF THE INVENTION

The present invention is based, at least in part, on the discovery that selectively inhibiting or blocking the expression or activity of both RGMb and PD-1 is useful in upregulating an immune response to thereby treat conditions the would benefit from upregulating an immune response (e.g., infections and cancers, such as colorectal cancer).

In one aspect, a method of treating a subject having a condition that would benefit from upregulation of an immune response comprising administering to the subject a therapeutically effective amount of at least one agent that selectively inhibits or blocks the expression or activity of both RGMb and PD-1 such that the condition that would benefit from upregulation of an immune response is treated, is provided.

Numerous embodiments are described herein that can be applied to any aspect of the present invention or embodiment thereof. For example, in one embodiment, the at least one agent is a bispecific or multispecific antibody, or antigen binding fragment thereof, selective for both RGMb and PD-1. In another embodiment, the at least one agent is a combination of agents comprising a first agent that selectively inhibits or blocks the expression or activity of RGMb and a second agent that selectively inhibits or blocks the expression or activity of PD-1. In still another embodiment, the first agent is an antibody, or an antigen binding fragment thereof, which specifically binds to RGMb protein, and wherein said second agent is an antibody, or an antigen binding fragment thereof, which specifically binds to PD-1 protein. In yet another embodiment, the antibody, or antigen binding fragment thereof, is murine, chimeric, humanized, composite, or human. In another embodiment, the antibody, or an antigen binding fragment thereof, is detectably labeled, comprises an effector domain, comprises an Fc domain, and/or is selected from the group consisting of Fv, F(ab')2, Fab', dsFv, scFv, sc(Fv)2, and diabodies fragments. In still another embodiment, the antibody, or antigen binding fragment thereof, is conjugated to a cytotoxic agent (e.g., a chemotherapeutic agent, a biologic agent, a toxin, or a radioactive isotope). In yet another embodiment, the at least one agent is selected from the group consisting of: a blocking antibody that binds RGMb, a non-activating form of RGMb, a soluble form of RGMb, a soluble form of an RGMb natural binding partner, an RGMb fission protein, a nucleic acid molecule that blocks RGMb transcription or translation, a small molecule RGMb antagonist, a blocking antibody that recognizes PD-1, a non-activating form of PD-1, a soluble form of PD-1, a soluble form of a PD-1 natural binding partner, a PD-1 fusion protein, a nucleic acid molecule that blocks PD-1 transcription or translation, and a small molecule PD-1 antagonist. In another embodiment, the blocking antibody that binds RGMb is selected from the group consisting of 1) anti-RGMb antibodies that block the interaction between a BMP and RGMb without blocking the interaction between PD-L2 and RGMb, 2) anti-RGMb antibodies that block the interaction between NEO1 and RGMb without blocking the interaction between PD-L2 and RGMb, 3) anti-RGMb antibodies that block both the BMP/RGMb interaction and NEO1/RGMb interaction and without blocking the interaction between PD-L2 and RGMb, 4) anti-RGMb antibodies that block the interaction between a BMP and RGMb and block the interaction between PD-L2 and RGMb, 5) anti-RGMb antibodies that block the interaction between NEO1 and RGMb and block the interaction between PD-L2 and RGMb, and 6) anti-RGMb antibodies that block both the BMP/RGMb interaction and NEO1/RGMb interaction and further block fee interaction between PD-L2 and RGMb. In still another embodiment, the blocking antibody that binds PD-1 is selected from the group consisting of anti-PD-1 antibodies that block the interaction between PD-1 and PD-L1 without blocking the interaction between PD-1 and PD-L2; anti-PD-1 antibodies that block the interaction between PD-1 and PD-L2 without blocking the interaction between PD-1 and PD-1; and anti-PD-1 antibodies that block both the interaction between PD-1 and PD-L1 and the interaction between PD-L1 and PD-L2.

In some embodiments, the at least one agent comprises an RNA interfering agent which inhibits or blocks RGMb and/or PD-1 expression or activity (e.g., a small interfering RNA (siRNA), small hairpin RNA (shRNA), microRNA (miRNA), or a piwiRNA (piRNA)). In another embodiment, the at least one agent comprises an antisense oligonucleotide complementary to RGMb and/or PD-1. In still another embodiment, the at least one agent comprises a peptide or peptidomimetic that inhibits or blocks RGMb and/or PD-1 expression or activity. In yet another embodiment, the at least one agent comprises a small molecule that inhibits or blocks RGMb and/or PD-1 expression or activity (e.g., a small molecule that inhibits a protein-protein interaction between RGMb and a natural RGMb binding partner and/or PD-1 and a natural PD-1 binding partner). In another embodiment, the at least one agent comprises an aptamer that inhibits or blocks RGMb and/or PD-1 expression or activity. In still another embodiment, the at least one agent is administered in a pharmaceutically acceptable formulation. In yet another embodiment, anergy, exhaustion, and/or clonal deletion of immune cells in the subject is reduced. In another embodiment, the method further comprises administering one or more additional agents or therapies that upregulates an immune response or treats the condition (e.g., an additional agent or therapy selected from the group consisting of immunotherapy, immune checkpoint: inhibition, a vaccine, chemotherapy, radiation, epigenetic modifiers (e.g., histone deacetylase (HDAC) modifiers, methylation modifiers, phosphorylation modifiers, and the like), and targeted therapy). In still another embodiment, the condition that would benefit from upregulation of an immune response is selected from the group consisting of cancer, a viral infection, a bacterial infection, a protozoan infection, a helminth infection, asthma associated with impaired airway tolerance, a neurological disease, multiple sclerosis, and an immunosuppressive disease. In yet another embodiment, the condition is responsive to PD-1 blockade alone. In another embodiment, the condition is a cancer such as colorectal cancer. In still another embodiment, the subject is a mammal, such as an animal model of the condition or a human.

In another aspect, a kit for treating a subject having a condition that would benefit from upregulation of an immune response comprising at least one agent that selectively inhibits or blocks the expression or activity of both RGMb and PD-1, is provided.

In one embodiment, the at least one agent is a bispecific or multispecific antibody, or antigen binding fragment thereof, selective for both RGMb and PD-1. In another embodiment, the at least one agent is a combination of antibodies or antigen, binding fragments thereof, comprising a first an antibody, or an antigen binding fragment thereof, which specifically binds to RGMb protein, and a second agent antibody, or an antigen binding fragment thereof, which specifically binds to PD-1 protein. In still another embodiment, the antibody, or antigen binding fragment thereof, is murine, chimeric, humanized, composite, or human. In yet another embodiment, the antibody, or antigen binding fragment thereof, is detectably labeled, comprises an effector domain, comprises an Fc domain, and/or is selected from the group consisting of Fv, F(ab')2, Fab', dsFv, scFv, sc(Fv)2, rIgG, sdAb, sdFv, and diabodies fragments. In another embodiment, the antibody, or antigen binding fragment thereof, is conjugated to a cytotoxic agent. In still another embodiment, the cytotoxic agent is selected from, the group consisting of a chemotherapeutic agent, a biologic agent, a toxin, and a radioactive isotope. In yet another embodiment, the antibody that binds RGMb is selected from the group consisting of 1) anti-RGMb antibodies that block the interaction between a BMP and RGMb without blocking the interaction between PD-L2 and RGMb, 2) anti-RGMb antibodies that block the interaction between NEO1 and RGMb without blocking the interaction between PD-L2 and RGMb, 3) anti-RGMb antibodies that block both the BMP/RGMb interaction and NEO1/RGMb interaction and without blocking the interaction between PD-L2 and RGMb, 4) anti-RGMb antibodies that block the interaction between a BMP and RGMb and block the interaction between PD-L2 and RGMb, 5) anti-RGMb antibodies that block the interaction between NEO1 and RGMb and block the interaction between PD-L2 and RGMb, and 6) anti-RGMb antibodies that block both the BMP/RGMb interaction and NEO1/RGMb interaction and further block the interaction between PD-L2 and RGMb. In another embodiment, the blocking antibody that binds PD-1 is selected from the group consisting of anti-PD-1 antibodies that block the interaction between PD-1 and PD-L1 without blocking the interaction between PD-1 and PD-L2; anti-PD-1 antibodies that block the interaction between PD-1 and PD-L2 without blocking the interaction between PD-1 and PD-L1; and anti-PD-1 antibodies that block both the interaction between PD-1 and PD-L1 and the interaction between PD-L1 and PD-L2.

DETAILED DESCRIPTION OF THE INVENTION

Figure 1:
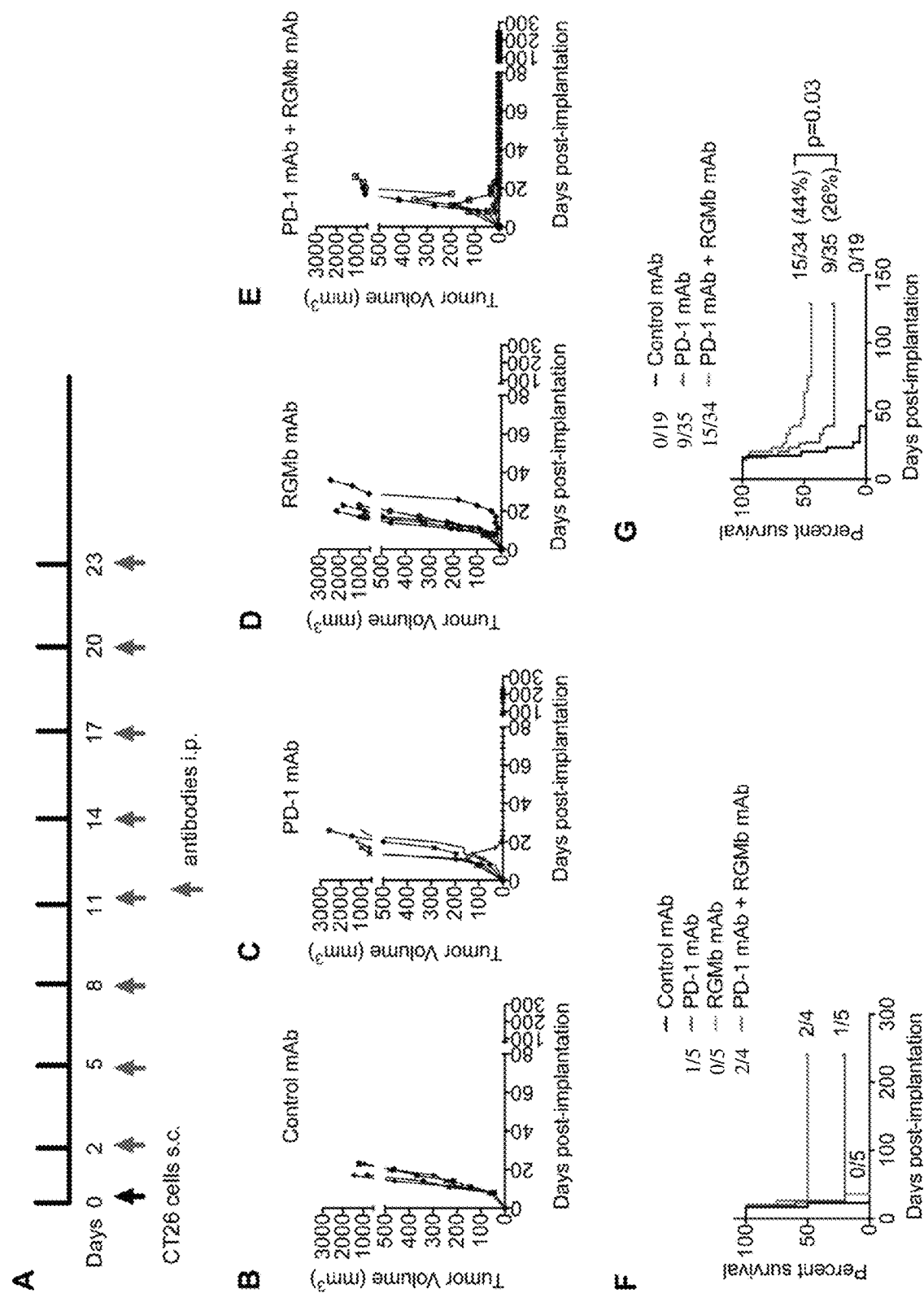
FIG. 1 includes 7 panels, identified as panels A, B, C, D, E, F, and G, which show anti-tumor efficacy of single and combination blockade of RGMb and PD-1. Panel A shows the experimental protocol used to study the CT26 syngeneic mouse model. BALB/c mice were injected with mouse colon cancer cell line CT26 subcutaneously in the left flank on day 0. Mice were treated with the indicated monoclonal antibodies (mAb) on days 2, 5, 8, 11, 14, 17, 20 and 23. Panels B-F show anti-tumor efficacies of RGMb and PD-1 mAbs, alone and in combination, as indicated by tumor volume (Panels B-E) and survival (Panel F). Panel G shows survival analysis results with pooled data from 3 experiments, n=19 (control mAb); n=35 (PD-1 mAb): n=34 (PD-1+RMGb mAb): p=0.03 (PD-1 mAb vs PD-1+RMGb mAs); and Kaplan-Meier survival analysis with Gehan-Breslow-Wilcoxon test.

Immune checkpoint, proteins are increasingly being recognized as important immunomodulators whose expression and/or activity inhibits immune responses that are desired. However, different immune checkpoints act in different contexts to suppress immune responses in different disorders, such that interfering with any specific immune checkpoint may not significantly alter an immunological response to a specific disorder. For example, colorectal cancer (CRC) is one of the leading causes of cancer related death in the Western world and is the third most common cancer diagnosed in the United States. Human CRC appears to be a poor responder to antibody blockade of programmed death-1 (PD-1) or PD-1 ligand 1 (PD-L1) in clinical trials.

Repulsive guidance molecule b (RGMb) is a receptor for PD-1 ligand 2 (PD-L2) (Xiao et al. (2014) *J. Exp. Med.* 211:943-959). RGMb, also known as DRAGON, was originally identified in the nervous system (Severyn et al. (2009) *Biochem. J.* 422:393-403). It is a member of the RGM family which consists of RGMa; RGMb and RGMc/hemojuvelin (Severyn et al. (2009) *Biochem. J.* 422:393-403). RGMs are glycosylphosphatidylinositol (gpi)-anchored membrane proteins that bind bone morphogenetic proteins (BMPs) and neogenin (Conrad et al. (2010) *Mol. Cell. Neurosci.* 43:222-231). Antibody blockade of the RGMb-PD-L2 interaction markedly impaired the development of respiratory tolerance (Xiao et al. (2014) *J. Exp. Med.* 211: 943-959). RGMb blockade might also break immune tolerance in the tumor microenviroment. As described herein, it was investigated whether specific combinations of immune checkpoints are active in regulating CRC and whether combinatorially inhibiting or blocking such immune checkpoints could upregulate immune responses, such as anti-CRC immune responses to thereby treat CRC. For example, the immunotherapeutic effect of antibody blockade of RGMb in the syngeneic mouse CT26 CRC model was determined. Single RGMb blockade showed no effect on survival. However, combination antibody blockade of RGMb and PD-1 increased survival, compared with PD-1 blockade alone (44% vs 26% long-term survival). Survivors were tumor-free and remained tumor-free after tumor re-challenges, indicating the development of immunologic memory. Long-term survivors (>6 months) showed no adverse events. Cell surface RGMb expression was detected on tumor infiltrating macrophages and dendritic cells. PD-L2 expression was up-regulated on tumor infiltrating macrophages after PD-1 mAb treatment and associated with higher level of IL-4 mRNA, which is correlated with smaller tumor volume. The results described herein indicate checkpoint combination immunotherapy for CRC and other cancers, especially where PD-1 blockade has some efficacy and/or may be insufficient.

I. Definitions

The articles "a" and "an" are used herein to refer to one or to more than one (i.e. to at least one) of the grammatical object of the article. By way of example, "an element" means one element or more than one element.

The "amount" of a marker, e.g., expression or copy number of a marker, or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker.

The term "altered level of expression" of a marker refers to an expression level or copy number of a marker in a test sample e.g., a sample derived from a subject suffering from cancer, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "altered activity" of a marker refers to an activity of a marker which is increased or decreased in a disease state, e.g., in a cancer sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

Unless otherwise specified herein, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody for simply "antibody portion"). The term "antigen-binding portion", as used herein, refers to one or more fragments of an antibody that retain the ability to specifically bind to an antigen (e.g., RGMb polypeptide or fragment thereof and/or PD-1 polypeptide or fragment thereof). It has been shown that the antigen-binding function of an antibody can be performed by fragments of a full-length, antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Bivalent mAbs can also consist of 2 IgV domains of 1 specificity and one IgV of the second specificity such that the antibody is bivalent (e.g., binds to 2 things but can have 2 copies of one of the binding specificities). Such, antibodies can be engineered by putting two IgVs in tandem on one side of the antibody. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16:778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl Acad. Sci. USA* 90:6444-6448; Poljak. R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein. As described further herein. The term "antibody" includes genetically engineered or otherwise modified forms of immunoglobulins, such as intrabodies, peptibodies, chimeric antibodies, fully human antibodies, humanized antibodies, and heteroconjugate antibodies (e.g., bispecific antibodies, diabodies, triabodies, tetrabodies, tandem di-scFv, tandem tri-scFv). The term functional antibody fragment also includes antigen binding fragments of antibodies including, but not limited to, fragment antigen binding (Fab) fragment, F(ab')$_2$ fragments, Fab' fragments, Fv fragments, recombinant IgG (rIgG) fragments, single chain variable fragment (scFv) and single domain antibodies (e.g., sdAb, sdFv, nanobody, and the like) fragments.

Antibodies may be polyclonal or monoclonal; xenogeneic, allogeneic, or syngeneic; or modified forms thereof (e.g., humanized, chimeric, etc.). Antibodies may also be fully human. Preferably, antibodies of the invention bind specifically or substantially specifically to RGMb and/or PD-1 polypeptides or fragments thereof. They may also be selective for such antigens such that they can distinguish such antigens from closely related antigens, such as other B7 family members. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

As used herein, a "blocking" antibody or an antibody "antagonist" is one which inhibits or reduces at least one biological activity of the antigen(s) it binds. For example, an anti-RGMb or anti-PD-1 antibody binds RGMb or PD-1, respectively, and inhibits the ability of RGMb to, for example, bind PD-L2, and inhibits the ability of PD-1 to, for example, bind PD-L1, PD-L2, or both PD-L1 and PD-L2. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluid that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The term "bispecific antibody" or "multispecific antibody" refers to an antibody that recognized more than one epitope. Such, antibodies are useful for targeting different proteins using the same agent. Methods of making such antibodies are well known in art (see, at least U.S. Pat. Nos. 5,798,229; 5,989,830; and Holliger et al. (2005) *Nat. Biotech.* 23:1126-1136).

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosareoma, lymphangioendotheliosareoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocyte, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

The term "control" refers to any reference standard suitable to provide a comparison to the expression products in the test sample, in one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/ tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository, in another preferred embodiment, the control may comprise a reference standard expression product level from any suitable source, including but not limited to housekeeping genes, an expression product level range from normal tissue (or other previously analyzed control sample), a previously determined expression product level range within a test sample from, a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/ tissue sample. In another preferred embodiment, the control may comprise an expression level for a set of patients, such as a set of cancer patients, or for a set of cancer patients receiving a certain treatment, or for a set: of patients with one outcome versus another outcome, in the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product, levels from cancer control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

The term "colorectal cancer" as used herein, is meant to include cancer of cells of the intestinal tract below the small intestine (e.g., the large intestine (colon), including the cecum, ascending colon, transverse colon, descending colon, and sigmoid colon, and rectum). Additionally, as used herein, the term "colorectal cancer" is meant to further include cancer of cells of the duodenum and small intestine (jejunum and ileum). Colorectal cancer also includes neoplastic diseases involving proliferation of a single clone of cells of the colon and includes adenocarcinoma and carcinoma of the colon whether in a primary site or metastasized.

Colorectal cancer (CRC) is the third most commonly diagnosed cancer and ranks second in cancer mortality. Extensive genetic and genomic analysis of human CRC has uncovered germline and somatic mutations relevant to CRC biology and malignant transformation (Fearon et al. (1990) *Cell* 61, 759-767). These mutations have been linked to well-defined disease stages from aberrant crypt proliferation or hyperplasic lesions to benign adenomas, to carcinoma in situ, and finally to invasive and metastatic disease, thereby establishing a genetic paradigm for cancer initiation and progression. Genetic and genomic instability are catalysts for colon carcinogenesis (Lengauer et at (1998) *Nature* 396:643-649), CRC can present with two distinct genomic profiles that have been termed (i) chromosomal instability neoplasia (CIN), characterized by rampant structural and numerical chromosomal aberrations driven in part by telomere dysfunction (Artandi et al. (2000) *Nature* 406:641-645; Fodde et al (2001) *Nat. Rev. Cancer* 1:55-67; Maser and DePinho (2002) *Science* 297:565-569; Rudolph et al. (2001) *Nat. Genet.* 28:155-159) and mitotic aberrations (Lengauer et al. (1998) *Nature* 396:643-649) and (ii) microsatellite instability neoplasia (MIN), characterized by near diploid karyotypes with alterations at the nucleotide level due to mutations in mismatch repair (MMR) genes (Fishel et al. (1993) *Cell* 75:1027-1038; Ilyas et al. (1999) *Eur. J. Cancer* 35:335-351; Modrich (1991) *Annu. Rev. Genet* 25:229-253; Parsons et al. (1995) *Science* 268:738-740; Parsons et al. (1993) *Cell* 75:1227-1236). Germline MMR mutations are highly penetrant lesions which drive the MIN phenotype in hereditary nonpolyposis colorectal cancers, accounting for 1-5% of CRC cases (de la Chapelle (2004) *Nat. Rev. Cancer* 4:769-780; Lynch and de la Chapelle (1999) *J. Med. Genet.* 36:801-818; Umar et al. (2004) *Nat. Rev. Cancer* 4:153-158). While CIN and MIN are mechanistically distinct their genomic and genetic consequences emphasize the requirement of dominant mutator mechanisms to drive intestinal epithelial cells towards a threshold of oncogenic changes needed for malignant transformation.

A growing number of genetic mutations have been identified and functionally validated in CRC pathogenesis. Activation of the WNT signaling pathway is an early requisite event for adenoma formation. Somatic alterations are present in APC in greater than 70% of nonfamilial sporadic cases and appear to contribute to genomic instability and induce the expression of c-myc and Cyclin D1 (Fodde et al. (2001) *Nat. Rev. Cancer* 1:55-67), while activating β-catenin mutations represent an alternative means of WNT pathway deregulation in CRC (Morin (199) *Science* 275:1787-1790). K-Ras mutations occur early in neoplastic progression and are present in approximately 50% of large adenomas (Fearon and Gruber (2001) Molecular abnormalities in colon and rectal cancer, ed. J. Mendelsohm, P. H., M. Israel, and L. Liotta, W.B. Saunders, Philadelphia). The BRAF serine/threonine kinase and PIK3CA lipid kinase are mutated in 5-18% and 28% of sporadic CRCs, respectively (Samuels et al. (2004) *Science* 304:554; Davies et al. (2002) *Nature* 417:949-954; Rajagopalan et al. (2002) *Nature* 418:934; Yuen et al. (2002) *Cancer Res.* 62:6451-6455). BRAF and K-ras mutations are mutually exclusive in CRC, suggesting over-lapping oncogenic activities (Davies et al. (2002) *Nature* 417:949-954; Rajagopalan et al. (2002) *Nature* 418: 934). Mutations associated with CRC progression, specifically the adenoma-to-carcinoma transition, target the TPS3 and the TGF-β pathways (Markowitz et al. (2002) *Cancer Cell* 1:233-236). Greater than 50% of CRCs harbor TP53 inactivating mutations (Fearon and Gruber (2001) Molecular abnormalities in colon and rectal cancer, ed. J. Mendelsohm, P. H., M. Israel, and L. Liotta, W.B. Saunders, Philadelphia) and 30% of cases possess TGFβ-RII mutations (Markowitz (2000) *Biochim. Biophys, Acta* 1470:M13-M20; Markowitz et al. (1995) *Science* 268:1336-1338). MIN cancers consistently inactivate TGFβ-RII by frameshift mutations, whereas CIN cancers target the pathway via inactivating somatic mutations in the TGFβ-RII kinase domain (15%) or in the downstream signaling components of the pathway, including SMAD4 (15%) or SMAD2 (5%) transcription factors (Markowitz (2000) *Biochim. Biophys. Acta* 1470:M13-M20). In some embodiments, the colorectal cancer is microsatellite instable (MSI) colorectal cancer (Llosa et al. (2014) *Cancer Disc.* CD-14-0863; published online Oct. 30, 2014), MSI represents about 15% of sporadic CRC and about 5-6^ of stage IV CRCs. MSI is caused by epigenetic silencing or mutation of DNA mismatch repair genes and typically presents with lower stage disease than microsatellite stable subset (MSS) CRC. MSI highly express immune checkpoints, such as PD-1, PD-L1, CTLA-4, LAG-3, and IDO. In other embodiments, the colorectal cancer is MSS CRC.

As used herein, the term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

As used herein, the term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, the term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5-AT-TGCC-3' and a region having the nucleotide sequence 5-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied fay the same nucleotide residue. More preferably, all nucleotide residue positions of each of the portions are occupied by the same nucleotide residue.

As used herein, the term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "humanized antibody," as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. Humanized antibodies may include amino acid residues not encoded by human germline immunoglobulin sequences (e.g., mutations introduced by random or site-specific mutagenesis m vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

As used herein, the term "inhibit" refers to any decrease in, for example a particular action, function, or interaction. For example, cancer is "inhibited" if at least one symptom of the cancer is reduced, slowed, or delayed. As used herein, cancer is also "inhibited" if recurrence or metastasis of the cancer is reduced, slowed, or delayed.

The term "interaction," when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting costimulation). To inhibit such an interaction results in the disruption of the activity of one or more molecules involved in the interaction. To enhance such an interaction is to prolong or increase the likelihood of said physical contact, and prolong or increase the likelihood of said activity.

An "isolated antibody" is intended to refer to an antibody that is substantially free of other antibodies having different antigenic specificities (e.g., an isolated antibody that specifically binds RGMb polypeptide or a fragment thereof or PD-1 polypeptide or a fragment thereof, is substantially free of antibodies that specifically bind antigens other than said polypeptide or a fragment thereof). Moreover, an isolated antibody may be substantially free of other cellular material and/or chemicals.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations, in which compositions of the invention are separated from cellular components of the cells from which they are isolated or recombinantly produced. In one embodiment, the language "substantially free of cellular material" includes preparations of having less than about 30%, 20%, 10%, or 5% (by dry weight) of cellular material. When an antibody, polypeptide, peptide or fusion protein or fragment thereof, e.g., a biologically active fragment thereof is recombinantly produced, it is also preferably substantially free of culture medium, i.e., culture medium represents less than about 20%, more preferably less than about 10%, and most preferably less than about 5% of the volume of the protein preparation.

As used herein, the term "isotype" refers to the antibody class (e.g., IgM or IgG1) that is encoded by heavy chain constant region genes.

As used herein, the term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

A "kit" is any manufacture (e.g. a package or container) comprising at least one reagent, e.g. a probe or small molecule, for specifically detecting and/or affecting the expression of a marker of the invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

A "marker" is a gene whose altered level of expression in a tissue or cell from its expression level in normal or healthy tissue or cell is associated with a disease state, such as cancer. A "marker nucleic acid" is a nucleic acid (e.g., mRNA, cDNA) encoded by or corresponding to a marker of the invention. Such marker nucleic acids include DNA (e.g., cDNA) comprising the entire or a partial sequence of any of the nucleic acid sequences set forth in the Sequence Listing or the complement of such a sequence. The marker nucleic acids also include RNA comprising the entire or a partial sequence of any of the nucleic acid sequences set forth in the Sequence Listing or the complement of such a sequence, wherein all thymidine residues are replaced with uridine residues. A "marker protein" is a protein, encoded by or corresponding to a marker of the invention. A marker protein comprises the entire or a partial sequence of any of the sequences set forth in the Sequence Listing. The terms "protein" and "polypeptide" are used interchangeably.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allow patients with large breast cancer to undergo breast-conserving surgery.

The "normal" level of expression or activity of a marker is the level of expression or activity of the marker in cells of a subject, e.g., a human patient, not afflicted with a disorder of interest, such as a cancer. An "over-expression" or "significantly higher level of expression" of a marker refers to an expression level in a test sample that is greater than the standard error of the assay employed, to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher that) the expression activity or level of the marker in a control sample (e.g., sample from a healthy subject not having the marker associated disease) and preferably, the average expression level of fee marker in several control samples. A "significantly lower level of expression" of a marker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA. DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., hematologic cancers, such as multiple myeloma), development, of one or more clinical factors, development of intestinal cancer, or recovery from the disease.

The term "response to anti-immune checkpoint therapy" or "outcome of therapy" relates to any response of a condition of interest (e.g., cancer) to a therapy, preferably to a change in tumor mass and/or volume after initiation of neoadjuvant or adjuvant chemotherapy, Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Response may also be assessed by caliper measurement or pathological examination of the tumor after biopsy or surgical resection for solid cancers. Responses may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more, in other embodiments, the percentage of patients who are in either CR, PR, and/or SD in any combination at least 30 days, 2 months, 3 months, 4 months, 5 months, 6 months, 7 months, 8 months, 9 months, 10 months, 11 months, 12 months, 18 months, 24 months, 30 months, 36 months, 60 months, or longer is at least 25%, 30%, 35%, 40%, 45%, 50%, 55%, 60%, 65%, 70%, 75%, 80%, 85%, or more. In some embodiments, the percentage is 100% over such a time period. Additional criteria for evaluating the response to cancer therapies are related to "survival," which includes all of the following; survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to copy number, level of expression, level of activity, etc. of a marker determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom the measurement values are known. In certain embodiments, the same doses of cancer therapeutic agents are administered to each subject. In related embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker threshold values that correlate to outcome of a cancer therapy can be determined using methods such as those described in the Examples section. Outcomes can also be measured in terms of a "hazard ratio" (the ratio of death rates for one patient group to another; provides likelihood of death at a certain time point), "overall survival" (OS), and/or "progression free survival." In certain embodiments, the prognosis comprises likelihood of overall survival rate at 1 year, 2 years, 3 years, 4 years, or any other suitable time point. The significance associated with the prognosis of poor outcome in all aspects of the present invention is measured by techniques known in the art. For example, significance may be measured with calculation of odds ratio. In a further embodiment, the significance is measured by a percentage. In one embodiment, a significant risk of poor outcome is measured as odds ratio of 0.8 or less or at least about 1.2, including by not limited to: 0.1, 0.2, 0.3, 0.4, 0.5, 0.6, 0.7, 0.8, 1.2, 1.3, 1.4, 1.5, 1.6, 1.7, 1.8, 1.9, 2.0, 2.5, 3.0, 4.0, 5.0, 10.0, 15.0, 20.0, 25.0, 30.0 and 40.0. In a further embodiment, a significant increase or reduction in risk is at least about 20%, including but not limited to about 25%, 30%, 35%, 40%, 45%, 50%, 55%, 60%, 65%, 70%, 75%, 80%, 85%, 90%, 95% and 98%. In a further embodiment, a significant increase in risk is at least about 50%. Thus, the present invention further provides methods for making a treatment decision for a cancer patient, comprising carrying out the methods for prognosing a cancer patient according to the different aspects and embodiments of the present invention, and then weighing the results in light of other known clinical and pathological risk factors, in determining a course of treatment for the cancer patient. For example, a cancer patient that is shown by the methods of the invention to have an increased risk of poor outcome by combination chemotherapy treatment can be treated with more aggressive therapies, including but not limited to radiation therapy, peripheral blood stem cell transplant, bone marrow transplant, or novel or experimental therapies under clinical investigation.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different, cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing," In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., p<0.05) when, compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

An "RNA interfering agent" as used herein, is defined as any agent which interferes with or inhibits expression of a target gene, e.g., a marker of the invention, by RNA interference (RNAi). Such RNA interfering agents include, but are not limited to, nucleic acid molecules including RNA molecules which, are homologous to the target gene, e.g., a marker of the invention, or a fragment thereof, short interfering RNA (siRNA), and small molecules which interfere with or inhibit expression of a target gene by RNA interference (RNAi).

"RNA interference (RNAi)" is an evolutionarily conserved process whereby die expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn and Culler) (2002) *J. Virol.* 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" or "inhibition of marker gene expression" includes any decrease in expression or protein activity or level of the target gene (e.g., a marker gene of the invention) or protein encoded by the target gene, e.g., a marker protein of the invention. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen." Selective binding is a relative term referring to the ability of an antibody to discriminate the binding of one antigen over another.

The term "sensitize" means to alter cancer cells or tumor cells in a way that allows for more effective treatment of the associated cancer with a cancer therapy (e.g., chemotherapeutic or radiation therapy. In some embodiments, normal cells are not affected to an extent that causes the normal cells to be unduly injured by the cancer therapy (e.g., chemotherapy or radiation therapy). An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

"Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the over hang on one strand is not dependent on the length of the overhang on the second strand. Preferably the siRNA is capable of promoting RNA interference through degradation or specific post-transcriptional gene silencing (PTGS) of the target messenger RNA (mRNA). In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al (2003) RNA April; 9(4):493-501 incorporated by reference herein). RNA interfering agents, e.g., siRNA molecules, may be administered to a subject having or at risk for having cancer, to inhibit expression of a marker gene of the invention, e.g., a marker gene which is overexpressed in cancer (such as the markers listed in Table 3) and thereby treat, prevent, or inhibit cancer in the subject.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) Science 282:63), and natural product extract libraries. In another embodiment, the compounds are small, organic non-peptidic compounds. In a further embodiment, a small molecule is not biosynthetic.

As used herein, "subject" refers to any healthy animal, mammal or human, or any animal, mammal or human afflicted with a disorder of interest such as cancer, e.g., colorectal, lung, ovarian, pancreatic, liver, breast, prostate, and/or colon carcinomas. The term "patient" is interchangeable with "subject."

The language "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

As used herein, the term "survival" includes all of the following; survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "synergistic effect" refers to the combined effect of two or more anticancer agents can be greater than the sum of the separate effects of the anticancer agents or alone. In some embodiments, it can provide for similar efficacy of monotherapy but with other unexpected improvements relative to monotherapy, such as reducing unwanted side effects.

The term "T cell" includes $CD4^+$ T cells and $CD8^+$ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells), as well as other antigen presenting cells (e.g., keratinocytes, endothelial cells, astrocytes, fibroblasts, and oligodendrocytes).

The term "therapeutic effect" refers to a local or systemic effect in animals, particularly mammals, and more particularly humans, caused by a pharmacologically active substance. The term: thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the invention and normal post-transcriptional processing (e.g. splicing), if any, of the RNA transcript, and reverse transcription of the RNA transcript.

As used herein, the term "unresponsiveness" or "tolerance" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2, T cell anergy occurs when T cells are exposed to antigen and receive a first signal (a T cell, receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the API sequence that can be found within the enhancer (Kang et al. (1992) *Science* 257:1134).

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
| --- | --- |
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for fusion protein or polypeptide amino acid sequence, corresponding nucleotide sequences that can encode the fission protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers described in the Examples) are well known in the art and readily available on publicly available databases, such as the National Center for Biotechnology Information (NCBI). For example, exemplary nucleic acid and amino acid sequences derived from publicly available sequence databases and publications are provided below and include, for example, PCT Publ. WO 2014/022759, which is incorporated herein in its entirety by this reference.

For example, the term "PD-1" refers to a member of the immunoglobulin gene superfamily that functions as a coinhibitory receptor having PD-L1 and PD-L2 as known ligands, PD-1 was previously identified using a subtraction cloning based approach to select for genes unregulated during TCR-induced activated T cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) *Int. Immunol.* 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol* 8:773).

The nucleic acid and amino acid sequences of a representative human PD-1 biomarker is available to the public at the GenBank database under NM_005018.2 and NP_005009.2 and is shown in Table 1 (see also Ishida et al (1992) 20 *EMBO J* 11:3887; Shinohara et al. (1994) *Genomics* 23:704; U.S. Pat. No. 5,698,520), PD-1 has an extracellular region containing immunoglobulin superfamily domain, a transmembrane domain, and an intracellular region including an immunoreceptor tyrosine-based inhibitory motif (ITIM) (Ishida et al. (1992) *EMBO J.* 11:3887; Shinohara et al. (1994) *Genomics* 23:704; and U.S. Pat. No. 5,698,520) and an immunoreceptor tyrosine-based switch motif (ITSM). These features also define a larger family of polypeptides, called the immunoinhibitory receptors, which also includes gp49B, PIR-B, and the killer inhibitory receptors (KIRs) (Vivier and Daeron (1997) *Immunol Today* 18:286). It is often assumed that the tyrosyl phosphorylated ITIM and ITSM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) *Immunol Today* 20(6):285-8). Nucleic acid and polypeptide sequences of PD-1 orthologs in organisms other than humans are well known and include, for example, mouse PD-1 (NM_008798.2 and NP_032824.1), rat PD-1 (NM_001106927.1 and NP_001100397.1), dog PD-1 (XM_543338.3 and XP_543338.3), cow PD-1 (NM_001083506.1 and NP_001076975.1), and chicken PD-1 (XM_422723.3 and XP_422723.2).

PD-1 polypeptides are inhibitory receptors capable of transmitting an inhibitory signal to an immune cell to thereby inhibit immune cell effector function, or are capable of promoting costimulation by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell, e.g., by engaging a natural PD-1 ligand on an antigen presenting cell. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

In some embodiments, a condition such as cancer is responsive to PD-1 blockade alone, but is significantly or synergistically more responsive when treated with PD-1 blockade and RGMb blockade in combination. Many conditions responsive to PD-1 blockade alone are known and include, without limitation, melanoma (e.g., advanced or metastatic melanoma), lung cancer (e.g., non small cell lung cancer and small cell lung cancer), breast cancer (e.g., HER-2 negative breast cancer, estrogen-receptor+/HER-2- breast cancer, and triple negative breast cancer), pancreatic cancer (e.g., pancreatic adenocarcinoma), and Hodgkin lymphoma, as well as bladder, gastric, head and neck, renal, prostate, gynecologic, and hematologic cancers.

The term "PD-1 ligand" refers to binding partners of the PD-1 receptor and includes both PD-L1 (Freeman et al. (2000) *J. Exp. Med.* 192:1027) and PD-L2 (Latchman et al. (2001) *Nat. Immunol.* 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) *J. Exp. Med.* 192:1027 for sequence data) and PD-L2 (See Latchman et al. (2001) *Nat. Immunol* 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are unregulated on activated monocyte and dendritic cells, although PD-L1 expression is broader. For example, PD-L1 is known to be constitutively expressed and unregulated to higher levels on murine hematopoietic cells (e.g., T cells, B cells, macrophages, dendritic cells (DCs), and bone marrow-derived, mast cells) and non-hematopoietic cells (e.g., endothelial, epithelial, and muscle cells), whereas PD-L2 is inducibly expressed on DCs, macrophages, and bone marrow-derived mast cells (see Butte et al. (2007) *Immunity* 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologies of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1, B7-2, B7h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (See the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds, Ig folds are comprised of a sandwich of two β sheets, each, consisting of anti-parallel β strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fell within other sets. IgV domains also share sequence patterns and are called V set domains. IgV domains are longer than IgC domains and contain an additional pair of β strands.

Preferred B7 polypeptides are capable of providing costimulatory or inhibitory signals to immune cells to thereby promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation. For example, when bound to a costimulatory receptor, PD-1 ligand can induce costimulation of immune cells or can inhibit immune cell costimulation, e.g., when present in soluble form. When bound to an inhibitory receptor, PD-1 ligand polypeptides can transmit an inhibitory signal to an immune cell. Preferred B7 family members include B7-1, B7-2, B7h, PD-L1 or PD-L2 and soluble fragments or derivatives thereof. In one embodiment, B7 family members bind to one or more receptors on an immune cell, e.g., CTLA4, CD28, ICOS, PD-1 and or other receptors, and, depending on the receptor, have the ability to transmit an inhibitory signal or a costimulatory signal to an immune cell, preferably a T cell.

Modulation of a costimulatory signal results in modulation of effector function of an immune cell. Thus, the term "PD-1 ligand activity" includes the ability of a PD-1 ligand polypeptide to bind its natural receptor(s) (e.g. PD-1 or B7-1), the ability to modulate immune cell costimulatory or inhibitory signals, and the ability to modulate the immune response.

The term "PD-L1" refers to a specific PD-1 ligand. Two forms of human PD-L1 molecules have been identified. One form is a naturally occurring PD-L1 soluble polypeptide, i.e., having a short hydrophilic domain and no transmembrane domain, and is referred to herein as PD-L1S (shown in Table 1 as SEQ ID NO: 4). The second form is a cell-associated polypeptide, i.e., having a transmembrane and cytoplasmic domain, referred to herein as PD-L1M (shown in SEQ ID NO: 6). The nucleic acid and amino acid sequences of representative human PD-L1 biomarkers regarding PD-L1M are also available to the public at the GenBank database under NM_014143.3 and NP_054862.1. PD-L1 proteins comprise a signal sequence, and an IgV domain and an IgC domain. The signal sequence of SEQ ID NO: 4 is shown from about amino acid 1 to about amino acid 18. The signal sequence of SEQ ID NO: 6 is shown from about amino acid 1 to about amino acid 18. The IgV domain of SEQ ID NO: 4 is shown from about amino acid 19 to about amino acid 134 and the IgV domain of SEQ ID NO: 6 is shown from about amino acid 19 to about amino acid 134. The IgC domain of SEQ ID NO: 4 is shown from about amino acid 135 to about amino acid 227 and the IgC domain of SEQ ID NO: 6 is shown from about amino acid 135 to about amino acid 227. The hydrophilic tail of the PD-L1 exemplified in SEQ ID NO: 4 comprises a hydrophilic tail shown from about amino acid 228 to about amino acid 245. The PD-L1 polypeptide exemplified in SEQ ID NO: 6 comprises a transmembrane domain shown from about amino acids 239 to about, amino acid 259 of SEQ ID NO: 6 and a cytoplasmic domain shown from about 30 amino acid 260 to about amino acid 290 of SEQ ID NO: 6. In addition, nucleic acid and polypeptide sequences of PD-L1 orthologs in organisms other than humans are well known and include, for example, mouse PD-L1 (NM_021893.3 and NP_068693.1), rat PD-L1 (NM_001191954.1 and NP_001178883.1), dog PD-L1 (XM_541302.3 and XP_541302.3), cow PD-L1 (NM_001163412.1 and NP_001156884.1), and chicken PD-L1 (XM_424811.3 and XP_424811.3).

The term "PD-L2" refers to another specific PD-1 ligand. PD-L2 is a B7 family member expressed on various APCs, including dendritic cells, macrophages and bone-marrow derived mast cells (Zhong et al. (2007) Eur. J. Immunol, 37:2405). APC-expressed PD-L2 is able to both inhibit T cell activation through ligation of PD-1 and costimulate T cell activation, through a PD-1 independent mechanism (Shin et al. (2005) J. Exp. Med. 201:1531). In addition, ligation of dendritic cell-expressed PD-L2 results in enhanced dendritic cell cytokine expression and survival (Radhakrishnan et al, (2003) J. Immunol. 37:1827; Nguyen et al. (2002) J. Exp. Med. 196:1393). The nucleic acid and amino acid sequences of representative human PD-L2 biomarkers (e.g., SEQ ID NOs: 7 and 8) are well known in the art and are also available to the public at the GenBank database under NM_025239.3 and NP_079515.2. PD-L2 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain. For example, amino acids 1-19 of SEQ ID NO: 8 comprises a signal sequence. As used herein, a "signal sequence" or "signal peptide" serves to direct a polypeptide containing such a sequence to a lipid bilayer, and is cleaved in secreted and membrane bound polypeptides and includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., valine, leucine, isoleucine or phenylalanine). In another embodiment, amino acid residues 220-243 of the native human PD-L2 polypeptide and amino acid residues 201-243 of the mature polypeptide comprise a transmembrane domain. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleueines, tyrosines, or tryptophans. Transmembrane domains are described in, for example, Zagotta, W. N. et al. (1996) Annu. Rev. Neurosci. 19:235-263. In still another embodiment, amino acid residues 20-120 of the native human PD-L2 polypeptide and amino acid residues 1-101 of the mature polypeptide comprise an IgV domain. Amino acid residues 121-219 of the native human PD-L2 polypeptide and amino acid residues 102-200 of the mature polypeptide comprise an IgC domain. As used herein, IgV and IgC domains are recognized in the art as Ig superfamily member domains. These domains correspond to structural units that have distinct folding patterns called Ig folds. Ig folds are comprised of a sandwich of two β sheets, each consisting of antiparallel (3 strands of 5-10 amino acids with a conserved disulfide bond between the two sheets in most, but not all, domains. IgC domains of Ig, TCR, and MHC molecules share the same types of sequence patterns and are called the CI set within the Ig superfamily. Other IgC domains fall within other sets. IgV domains also share sequence patterns and are called V set domains. IgV domains are longer than C-domains and form, an additional pair of strands. In yet another embodiment, amino acid residues 1-219 of the native human PD-L2 polypeptide and amino acid residues 1-200 of the mature polypeptide comprise an extracellular domain. As used herein, the term "extracellular domain" represents the N-terminal amino acids which extend as a tail from the surface of a cell. An extracellular domain of the present invention includes an IgV domain and an IgC domain, and may include a signal peptide domain. In still another embodiment amino acid residues 244-273 of fee native human PD-L2 polypeptide and amino acid residues 225-273 of the mature polypeptide comprise a cytoplasmic domain. As used herein, the term "cytoplasmic domain" represents the C-terminal amino acids which extend as a tail into the cytoplasm of a cell. In addition, nucleic acid and polypeptide sequences of PD-L2 orthologs in organisms other than humans are well known and include, for example, mouse PD-L2 (NM_021396.2 and NP_06737.1), rat PD-L2 (NM_001107582.2 and NP_001101052.2), dog PD-L2 (XM_847012.2 and XP_852105.2), cow PD-L2 (XM_586846.5 and XP_586846.3), and chimpanzee PD-L2 (XM_001140776.2 and XP_001140776.1).

The term "PD-L2 activity," "biological activity of PD-L2," or "functional activity of PD-L2," refers to an activity exerted by a PD-L2 protein, polypeptide or nucleic acid molecule on a PD-L2-responsive cell or tissue, or on a PD-L2 polypeptide binding partner, as determined m vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor RGMb. Alternatively, a PD-L2 activity is an indirect activity, such as a cellular signaling activity mediated by interaction of the PD-L2 polypeptide with its natural binding partner (i.e., physiologically relevant interacting macromolecule involved in an immune function or other biologically relevant function), e.g., RGMb. The biological activities of PD-L2 are described herein. For example, the PD-L2 polypeptides of the present invention can have one or more of the following activities; 1) bind to and/or modulate the activity of the receptor RGMb, PD-1, or other PD-L2 natural binding partners, 2) modulate intra-or intercellular signaling, 3) modulate activation of immune cells, e.g., T lymphocytes, and 4) modulate the immune response of an organism, e.g., a mouse or human organism.

The term "RGMb" or "DRAGON" refers to a glycosylphosphatidylinositol (GPI)-anchored member of the repulsive guidance molecule family, which, consists of RGMa, RGMb and RGMc/hemojuvelin (Severyn et al. (2009) Biochem J. 422:393-403). RGMs are glycosylphosphatidylinositol (gpi)-anchored membrane proteins that do not directly signal but act as co-receptors, that modulate the activity of signaling receptors by binding bone morphogenic proteins (BMPs) and neogenin (Conrad et al. (2010) Mol. Cell Neurosci. 43:222-231). RGMb directly binds to BMP-2 or BMP-4, which in turn bind to type I receptors (ALK1, ALK2, ALK3 and ALK6) and type II receptors (BMPRII, ActRIIa and ActRIIb) (Corradini et al. (2009) Cytokine Growth Factor Rev. 20:389-398 and Yoshioka et al. (2012) Eur. J. Immunol 42:749-759), RGMs coordinate utilization of specific BMP receptors (Corradini et al. (2009) Cytokine Growth Factor Rev. 20:389-398). The function of RGMs was originally described in the developing nervous system where they regulate motility and adhesion of neurons and are critical in embryonic development (Samad et al. (2004) J. Neurosci. 24:2027-2036 and Matsunaga et al. (2004) Nat. Cell Biol. 6:749-755). In addition, RGMb expression is observed in macrophages and other cells of the immune system (Xia et al. (2010) J. Immunol. 186:1369-1376). A role for RGMb in the immune system is only beginning to emerge (Galligan et al. (2007) J. Immunol. 143:2714-2722 and Xia et al. (2010), J. Immunol. 186:1369-1376). For example, the relationship of RGMb-BMP-neogenin signaling in mediating respiratory disorders or that modulating such signaling could effectively treat such respiratory disorders, especially at the effector stage, were not heretofore known.

Co-receptors such as RGMb often have large extracellular domains with multiple motifs enabling them to bind several different ligands. RGMb has been shown to bind neogenin (Bell et al (2013) Science 341:77-80 and Conrad et al (2009) Mol. Cell Neurosci. 43:222-231), bone morphogenetic proteins (BMPs) (Samad et al. (2005) J. Biol. Chem. 280: 14122-14129 and Xia et al. (2010) J. Am. Soc. Nephrol 21:666-677), and more recently, programmed death ligand 2 (PD-L2). The nucleic acid and amino acid sequences of representative human RGMb biomarkers (e.g., SEQ ID NOs: 9 and 10) are well known in the art and are also available to the public at the GenBank database under NM_001012761.2 and NP_001012779.2. RGMb proteins are characterized by common structural elements. In some embodiments, RGMb proteins comprise conserved domains with homology to notch-3, phosphatidylinositol-4-phosphate-5-kinase type II beta, insulin-like growth factor binding protein-2, thrombospondin, ephrin type-B receptor 3 precursor, and Slit-2, all of which are known to influence axonal guidance, neurite outgrowth, and other neuronal developmental functions. The C-terminus of RGMb also contains a hydrophobic domain indicative of a 21 amino acid extracellular GPI anchoring. In addition, nucleic acid and polypeptide sequences of RGMb orthologs in organisms other than humans are well known and include, for example, mouse RGMb (NM_178655.3 and NP_848730.2), chimpanzee RGMb (XM_517848.3 and XP_517848.2), cow RGMb (XM_026894.13.1 and XP_02689459.1), chicken RGMb (XM_42860.3 and XP_424860.3), and zebrafish RGMb (NM_001001727.1 and NP_01001727.1).

Apart from, its role in immunomodulation via the RGMb-PD-L2 interaction, RGMb is also physiologically relevant to the "RGMb-NEO1-BMP signaling pathway," which refers to one of the intracellular signaling pathways activated by the binding of BMP factors to RGMb and NEO1 co-receptors. Without being bound by theory, it is believed that the RGMb-NEO1-BMP signaling pathway signals according to a model whereby RGMb forms a signaling super-complex of BMP-BMP receptors-RGMb-Neogenin (BERN supercomplex). RGMb directly binds to BMP-2 or BMP-4 as natural binding partners, which bind to type I BMP receptors (BMPR1a, BMPR1b, ACVR1, ACVRL1) and recruit type II BMP receptors (BMPR2, ACVR2a, ACVR2b) (Corradini et al. (2009) Cytokine Growth Factor Rev. 20:389-398 and Yoshioka et al. (2012) Eur. J. Immunol. 42:749-759). Then, type II BMP receptors phosphorylate type I BMP receptors, which phosphorylate Smad1/5/8 or p38 mitogen activated protein kinase (MAPK) and extra-cellular signal-regulated protein kinase (ERK), leading to downstream target gene transcription (Corradini et al. (2009) Cytokine Growth Factor Rev. 20:389-398 and Xia et al. (2010) J. Immunol. 186:1369-1376). RGMs facilitate the utilization, of ACVR2a by BMP-2/4. In the absence of an RGM, BMP-2/4 preferentially utilize BMPR2 (Corradini et al. (2009) Cytokine Growth Factor Rev. 20:389-398). RGMb may also signal through neogenin as a natural binding partner and downstream effector Rho, triggering cytoskel-etal rearrangement (Bell et al. (2013) Science 341:77-80 and Conrad et al. (2007) J. Biol. Chem. 282:16423-16433). PD-L2 may interact with this BBRN supercomplex by binding to RGMb, and modulate these signaling pathways. For example, PD-L2 binding to PD-1 which results in tyrosine phosphorylation of the PD-1 cytoplasmic domain, recruitment of tyrosine phosphatases, particularly SHP-2, and attenuation of antigen receptor signals. Thus, PD-L2 may participate in three important signaling circuits, the PD-1, BMP, and neogenin signaling pathways, by binding to either PD-1 or RGMb. In some embodiments, the RGMb-NEO1-BMP signaling pathway is limited to subsets of biomolecules within the pathway, such as RGMb, NEO1, BMP2, and BMP4, or even individual biomolecules within the pathway, such as RGMb. Exemplary agents useful for inhibiting the RGMb-NEO1-BMP signaling pathway, or other biomarkers described herein, include antibodies, small molecules, peptides, peptidomimetics, natural ligands, and derivatives of natural ligands, that can either bind and/or inactivate or inhibit target proteins, or fragments thereof; as well as RNA interference, antisense, nucleic acid aptamers, etc. that can downregulate the expression and/or activity of target nucleic acids, or fragments thereof, in some embodi-ments, a single agent or a combination of agents can be used to disrupt signaling by the BBRN supercomplex. Exemplary inhibitors of the RGMb-NEO1-BMP signaling pathway are also well known in the art and include, but are not limited to BMP inhibitors, such as inhibitors of BMP2 and BMP4 include noggin, chrodin, Cerl, DAN, WISE (USAG-1), SOST (Extodin), and Gremlin, as well as antibodies, nucleic acids, and extracellular domains of BMP receptors such as soluble activin extracellular domains. Similarly, antibodies that bind to RGMb and/or neogenin to block the interaction with its natural binding partners are contemplated, as well as the use of such natural binding partners, or soluble frag-ments thereof.

The term "neogenin" refers to a gene encoding the NEO1 protein. At least three splice variants of human neogenin are known. The nucleic acid sequence of transcript variant 1 is available as NM_0024993, which encodes isoform 1 that is available as NP_002490.2. Transcript variant 2 (NM_001172623.1) lacks an in-frame exon in the coding region relative to transcript variant 1, which encodes an isoform that is shorter than isoform 1 (NP_001166094.1). Transcript variant 3 (NM_001172624.1) also lacks an in-frame exon in the coding region relative to transcript variant 1, which encodes an isoform that is shorter than isoform 1 (NP_001166095.1). Neogenin proteins are characterized by common structural elements. In some embodiments, neo-genin proteins comprise tour N-terminal immunoglobulin-like domains, six fibronectin type III domains, a transmem-brane domain and a C-terminal internal domain that shares homology with the tumor suppressor candidate gene, deleted in colorectal cancer (DOC). In addition, nucleic acid and polypeptide sequences of neogenin orthologs in organisms other than humans are well known and include, for example, mouse neogenin (NM_008684.2, NP_032710.2, NM_001042752.1, and NP_001036217.1), chimpanzee neogenin (XM_510660.3, XP_510660.3, XM_003314752.1, XP_003314800.1, XM_003314751.1, and XP_003314799.1), monkey neogenin (NM_00121500.1 and NP_001248429.1), dog neogenin (XM_05638577.1, XP_005638634.1, XM_005638581.1, XP_005638638.1, XM_05638578.1, XP_005638635.1, XM_005638579.1, XP_005638636.1, XM_005638580.1, XP_005638637.1, XM_544760.4, XP_544760.2, XM_003433937.2, XP_003433985.1, XM_003433936.2, and XP_03433984.1), cow neogenin (XM_005211431.1, XP_05211488.1, XM_005211432.1, XP_005211489.1, XM_02690492.3, XP_02690538.1, XM_003586508.2, XP_003586556.1, XM_005211433.1, XP_005211490.1, XM_003586507.2, and XP_003586555.1), rat neogenin (XM_006243186.1 and XP_006243248.1), chicken neo-genin (XM_004943656.1, XP_004943713.1, XM_004943654.1, XP_104943711.1, XM_004943655.1, XP_004943712.1, XM_413704.4, XP_413704.4, XM_04943657.1, and XP_004943714.1), and zebrafish neo-genin (NM_173218.1 and NP_775325.1).

The term "BMP" refers to a family with more than 20 members related to the transforming growth factor-β (TGF-β) family (Bragdon et al. (2011) Cell Signal 23:609-620 and Yoshioka et al. (2012) Eur. J. Immunol 42:749-759). Sig-naling is initiated when a BMP ligand binds to complexes of two type I mid two type II serine/threonine kinase receptors. Constitutively active type II receptors phosphorylate type I receptors, which phosphorylate Smad proteins. The BMP subfamily signals via one set of receptor-activated Smads (Smad1, Smad5 and Smad8), whereas the TGF-β subfamily signals via another set (Smad2 and Smad3). Phosphorylated receptor-activated Smads form heteromeric complexes with common mediator Smad4, and the Smad complexes trans-locate to the nucleus where they modulate gene transcrip-tion. Regulation of this pathway occurs at multiple levels in order to generate specificity and to finely tune these signals. One key regulatory mechanism is the promotion or inhibi-tion of ligand binding by coreceptors. RGM family members RGMa and RGMb (DRAGON) are the first described co-receptors for the BMP subfamily. Both RGMa and RGMb bind selectively to BMP-2 and BMP-4 ligands, interact with BMP receptors and enhance cellular responses to BMP ligands (Samad et al. (2005) J. Biol. Chem. 280:14122-14129; Babitt et al. (2005) J. Biol. Chem. 280:29820-29827 (2005); and Shi et al. (2003) Cell 113:685-700).

The nucleic acid and amino acid sequences of represen-tative human BMP2 (e.g., SEQ ID NOs: 13 and 14) bio-markers are well known in the art and are also available to the public at the GenBank database under NM_001012761.2 and NP_001012779.2 (preproprotein at residues 1-396, sig-nal peptide at residues 1-23, proprotein at residues 24-396, and the mature peptide at residues 283-396). In addition, nucleic acid and polypeptide sequences of BMP2 orthologs in organisms other than humans are well known and include, for example, mouse BMP2 (NM_007553.3 and NP_031579.2 with preproprotein at residues 1-394, signal peptide at residues 1-23, proprotein at residues 24-394, and the mature peptide at residues 281-394), chimpanzee BMP2 (XM_514508.2 and XP_514508.2), monkey BMP2 (XM_001115987.1 and XP_001115987.1), dog BMP2 (XM_534351.4 and XP_534351.2), cow BMP2 (NM_001099141.1 and NP_001092611.1), rat BMP2 (NM_017178.1 and NP_058874.1), chicken BMP2 (NM_204358.1 and NP_989689.1), and zebrafish BMP2 (NM_131360.1 and NP_571435.1).

At least three splice variants of human BMP4 are known. The nucleic acid sequence of transcript variant 1 is available as NM_00.1202.4. Transcript variant 2 (NM_130850.2) and variant 3 (NM_130851.2) each differ from transcript variant 1 only in the 5' untranslated region (5' UTR) such that all three variants encode the same protein (NP_001193.2, NP_570911.2, and NP_570912.2) (preproprotein at residues 1-408, signal peptide at residues 5-24, proprotein at residues 36-275, and, in some embodiments, the mature peptide at residues 308-408). In addition, nucleic acid and polypeptide sequences of BMP4 orthologs in organisms other than humans are well known and include, for example, mouse BMP4 (NM_007554.2 and NP_031580.2 with preproprotein at residues 1-408, signal peptide at residues 1-19, proprotein at residues 36-276, and, in some embodiments, the mature peptide at residues 308-408), chimpanzee BMP4 (XM_509954.3, XP_509954.3, XM_03314329.1, XP_003314377.1, XM_03314330.1, and XP_003314378.1), monkey BMP4 (XM_001084801.2, XP_001084801.1, XM_001084680.2, XP_001084680.1, XM_002805069.1, XP_002805115.1, XM_00108431.7.1 and XP_001084317.1), dog BMP4 (NM_001287170.1 and NP_001274099.1), cow BMP4 (NM_001045877.1 and NP_001039342.1), rat BMP4 (NM_012827.2 and NP_036959.2), and zebrafish BMP4 (NM_131342.2 and NP_571417.1).

TABLE 1

SEQ ID NO: 1 Human PD-1 cDNA Sequence

```
cactctggtg gggctgctcc aggc atg cag atc cca cag gcg ccc tgg cca         51
               Met Gln Ile Pro Gln Ala Pro Trp Pro
                1                 5 gtc gtc tgg gcg gtg cta caa ctg ggc tgg cgg cca gga tgg ttc tta        99
Val Val Trp Ala Val Leu Gln Leu Gly Trp Arg Pro Gly Trp Phe Leu
 10                  15                  20                  25 gac tcc cca gac agg ccc tgg aac ccc ccc acc ttc tcc cca gcc ctg       147
Asp Ser Pro Asp Arg Pro Trp Asn Pro Pro Thr Phe Ser Pro Ala Leu
                 30                  35                  40 ctc gtg gtg acc gaa ggg gac aac gcc acc ttc acc tgc agc ttc tcc       195
Leu Val Val Thr Glu Gly Asp Asn Ala Thr Phe Thr Cys Ser Phe Ser
                 45                  50                  55 aac aca tcg gag agc ttc gtg cta aac tgg tac cgc atg agc ccc agc       243
Asn Thr Ser Glu Ser Phe Val Leu Asn Trp Tyr Arg Met Ser Pro Ser
             60                  65                  70 aac cag acg gac aag ctg gcc gcc ttc ccc gag gac cgc agc cag ccc       291
Asn Gln Thr Asp Lys Leu Ala Ala Phe Pro Glu Asp Arg Ser Gln Pro
         75                  80                  85 ggc cag gac tgc cgc ttc cgt gtc aca caa ctg ccc aac ggg cgt gac       339
Gly Gln Asp Cys Arg Phe Arg Val Thr Gln Leu Pro Asn Gly Arg Asp
 90                  95                 100                 105 ttc cac atg agc gtg gtc agg gcc cgg cgc aat gac agc ggc acc tac       387
Phe His Met Ser Val Val Arg Ala Arg Arg Asn Asp Ser Gly Thr Tyr
                110                 115                 120 ctc tgt ggg gcc atg tcc ctg gcc ccc aag gcg cag atc aaa gag agc       435
Leu Cys Gly Ala Ile Ser Leu Ala Pro Lys Ala Gln Ile Lys Glu Ser
                125                 130                 135 ctg cgg gca gag ctc agg gtg aca gag aga agg gca gaa gtg ccc aca       483
Leu Arg Ala Glu Leu Arg Val Thr Glu Arg Arg Ala Glu Val Pro Thr
            140                 145                 150 gcc cac ccc agc ccc tca ccc agg tca gcc ggc cag ttc caa acc ctg       531
Ala His Pro Ser Pro Ser Pro Arg Ser Ala Gly Gln Phe Gln Thr Leu
        155                 160                 165 gtg gtt ggt gtc gtg ggc ggc ctg ctg ggc agc ctg gtg ctg cta gtc       579
Val Val Gly Val Val Gly Gly Leu Leu Gly Ser Leu Val Leu Leu Val
170                 175                 180                 185 tgg gtc ctg gcc gtc atc tgc tcc cgg gcc gca cga ggg aca ata gga       627
Trp Val Leu Ala Val Ile Cys Ser Arg Ala Ala Arg Gly Thr Ile Gly
                190                 195                 200
```

TABLE 1-continued

```
gcc agg cgc acc ggc cag ccc ctg aag gag gac ccc tca gcc gtg cct    675
Ala Arg Arg Thr Gly Gln Pro Leu Lys Glu Asp Pro Ser Ala Val Pro
            205                 210                 215 gtg ttc tct gtg gac tat ggg gag ctg gat ttc cag tgg cga gag aag    723
Val Phe Ser Val Asp Tyr Gly Glu Leu Asp Phe Gln Trp Arg Glu Lys
            220                 225                 230 acc ccg gag ccc ccc gtg ccc tgt gtc cct gag cag acg gag tat gcc    771
Thr Pro Glu Pro Pro Val Pro Cys Val Pro Glu Gln Thr Glu Tyr Ala
235                 240                 245 acc att gtc ttt cct agc gga atg ggc acc tca tcc ccc gcc cgc agg    819
Thr Ile Val Phe Pro Ser Gly Met Gly Thr Ser Ser Pro Ala Arg Arg
250                 255                 260                 265 ggc tca gct gac ggc cct cgg agt gcc cag cca ctg agg cct gag gat    867
Gly Ser Ala Asp Gly Pro Arg Ser Ala Gln Pro Leu Arg Pro Glu Asp
            270                 275                 280 gga cac tgc tct tgg ccc ctc tgaccggctt ccttggccac cagtgttctg cag    921
Gly His Cys Ser Trp Pro Leu
            285
```

SEQ ID NO: 2 Human PD-1 Amino Acid Sequence

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Ser Ala Gly Gln Phe Gln Thr Leu Val Val Gly Val Val Gly Gly
                165                 170                 175

Leu Leu Gly Ser Leu Val Leu elu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

TABLE 1-continued

| SEQ ID NO: 3 Human PD-L1S cDNA Acid Sequence | |
|---|---|
| gcttcccgag gctccgcacc agccgcgctt ctgtccgcct gcagggcatt ccagaaag | 58 |

| atg | agg | ata | ttt | gct | gtc | ttt | ata | ttc | atg | acc | tac | tgg | cat | ttg | ctg | 106 |
|---|---|---|---|---|---|---|---|---|---|---|---|---|---|---|---|---|
| Met | Arg | Ile | Phe | Ala | Val | Phe | Ile | Phe | Met | Thr | Tyr | Trp | His | Leu | Leu | |
| 1 | | | | 5 | | | | | 10 | | | | | 15 | | |

| aac | gca | ttt | act | gtc | acg | gtt | ccc | aag | gac | cta | tat | gtg | gta | gag | tat | 154 |
|---|---|---|---|---|---|---|---|---|---|---|---|---|---|---|---|---|
| Asn | Ala | Phe | Thr | Val | Thr | Val | Pro | Lys | Asp | Leu | Tyr | Val | Val | Glu | Tyr | |
| | | | 20 | | | | | 25 | | | | | 30 | | | |

| ggt | agc | aat | atg | aca | att | gaa | tgc | aaa | ttc | cca | gta | gaa | aaa | caa | tta | 202 |
|---|---|---|---|---|---|---|---|---|---|---|---|---|---|---|---|---|
| Gly | Ser | Asn | Met | Thr | Ile | Glu | Cys | Lys | Phe | Pro | Val | Glu | Lys | Gln | Leu | |
| | | 35 | | | | | 40 | | | | | 45 | | | | |

| gac | ctg | gct | gca | cta | att | gtc | tat | tgg | gaa | atg | gag | gat | aag | aac | att | 250 |
|---|---|---|---|---|---|---|---|---|---|---|---|---|---|---|---|---|
| Asp | Leu | Ala | Ala | Leu | Ile | Val | Tyr | Trp | Glu | Met | Glu | Asp | Lys | Asn | Ile | |
| | 50 | | | | | 55 | | | | | 60 | | | | | |

| att | caa | ttt | gtg | cat | gga | gag | gaa | gac | ctg | aag | gtt | cag | cat | agt | agc | 298 |
|---|---|---|---|---|---|---|---|---|---|---|---|---|---|---|---|---|
| Ile | Gln | Phe | Val | His | Gly | Glu | Glu | Asp | Leu | Lys | Val | Gln | His | Ser | Ser | |
| 65 | | | | | 70 | | | | | 75 | | | | | 80 | |

| tac | aga | cag | agg | gcc | cgg | ctg | ttg | aag | gac | cag | ctc | tcc | ctg | gga | aat | 346 |
|---|---|---|---|---|---|---|---|---|---|---|---|---|---|---|---|---|
| Tyr | Arg | Gln | Arg | Ala | Arg | Leu | Leu | Lys | Asp | Gln | Leu | Ser | Leu | Gly | Asn | |
| | | | | 85 | | | | | 90 | | | | | 95 | | |

| gct | gca | ctt | cag | atc | aca | gat | gtg | aaa | ttg | cag | gat | gca | ggg | gtg | tac | 394 |
|---|---|---|---|---|---|---|---|---|---|---|---|---|---|---|---|---|
| Ala | Ala | Leu | Gln | Ile | Thr | Asp | Val | Lys | Leu | Gln | Asp | Ala | Gly | Val | Tyr | |
| | | | 100 | | | | | 105 | | | | | 110 | | | |

| cgc | tgc | atg | atc | agc | tat | ggt | ggt | gcc | gac | tac | aag | cga | att | act | gtg | 442 |
|---|---|---|---|---|---|---|---|---|---|---|---|---|---|---|---|---|
| Arg | Cys | Met | Ile | Ser | Tyr | Gly | Gly | Ala | Asp | Tyr | Lys | Arg | Ile | Thr | Val | |
| | | | 115 | | | | | 120 | | | | | 125 | | | |

| aaa | gtc | aat | gcc | cca | tac | aac | aaa | atc | aac | caa | aga | att | ttg | gtt | gtg | 490 |
|---|---|---|---|---|---|---|---|---|---|---|---|---|---|---|---|---|
| Lys | Val | Asn | Ala | Pro | Tyr | Asn | Lys | Ile | Asn | Gln | Arg | Ile | Leu | Val | Val | |
| | 130 | | | | | 135 | | | | | 140 | | | | | |

| gat | cca | gtc | acc | tct | gaa | cat | gaa | ctg | aca | tgt | cag | gct | gag | ggc | tac | 538 |
|---|---|---|---|---|---|---|---|---|---|---|---|---|---|---|---|---|
| Asp | Pro | Val | Thr | Ser | Glu | His | Glu | Leu | Thr | Cys | Gln | Ala | Glu | Gly | Tyr | |
| 145 | | | | | 150 | | | | | 155 | | | | | 160 | |

| ccc | aag | gcc | gaa | gtc | atc | tgg | aca | agc | agt | gac | cat | ca | gtc | ctg | agt | 586 |
|---|---|---|---|---|---|---|---|---|---|---|---|---|---|---|---|---|
| Pro | Lys | Ala | Glu | Val | Ile | Trp | Thr | Ser | Ser | Asp | His | Gln | Val | Leu | Ser | |
| | | | | 165 | | | | | 170 | | | | | 175 | | |

| ggt | aag | acc | acc | acc | acc | aat | tcc | aag | aga | gag | gag | aag | ctt | ttc | aat | 634 |
|---|---|---|---|---|---|---|---|---|---|---|---|---|---|---|---|---|
| Gly | Lys | Thr | Thr | Thr | Thr | Asn | Ser | Lys | Arg | Glu | Glu | Lys | Leu | Phe | Asn | |
| | | | 180 | | | | | 185 | | | | | 190 | | | |

| gtg | acc | agc | aca | ctg | aga | atc | aac | aca | aca | act | aat | gag | att | ttc | tac | 682 |
|---|---|---|---|---|---|---|---|---|---|---|---|---|---|---|---|---|
| Val | Thr | Ser | Thr | Leu | Arg | Ile | Asn | Thr | Thr | Thr | Asn | Glu | Ile | Phe | Tyr | |
| | | | 195 | | | | | 200 | | | | | 205 | | | |

| tgc | act | ttt | agg | aga | tta | gat | cct | gag | gaa | aac | cat | aca | gct | gaa | ttg | 730 |
|---|---|---|---|---|---|---|---|---|---|---|---|---|---|---|---|---|
| Cys | Thr | Phe | Arg | Arg | Leu | Asp | Pro | Glu | Glu | Asn | His | Thr | Ala | Glu | Leu | |
| | | | 210 | | | | | 215 | | | | | 220 | | | |

| gtc | atc | cca | ggt | aat | att | ctg | aat | gtg | tcc | att | aaa | ata | tgt | cta | aca | 778 |
|---|---|---|---|---|---|---|---|---|---|---|---|---|---|---|---|---|
| Val | Ile | Pro | Gly | Asn | Ile | Leu | Asn | Val | Ser | Ile | Lys | Ile | Cys | Leu | Thr | |
| 225 | | | | | 230 | | | | | 235 | | | | | 240 | |

| ctg | tcc | cct | agc | acc | tagcatgatg tctgcctatc atagtcattc agtgattgtt | 833 |
|---|---|---|---|---|---|---|
| Leu | Ser | Pro | Ser | Thr | | |
| | | | | 245 | | | gaataaatga atgaatgaat aacactatgt ttacaaaata tatcctaatt cctcacctcc    893 attcatccaa accatattgt tacttaataa acattcagca gatatttatg gaataaaaaa    953 aaaaaaaaaa aaaaa    968

TABLE 1-continued

SEQ ID NO: 4 Human PD-L1S Amino Acid Sequence

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
            210                 215                 220

Val Ile Pro Gly Asn Ile Leu Asn Val Ser Ile Lys Ile Cys Leu Thr
225                 230                 235                 240

Leu Ser Pro Ser Thr
                245

SEQ ID NO: 5 Human PD-L1M cDNA Acid Sequence cgaggctccg caccagccgc gcttctgtcc gcctgcaggg cattccagaa agatgagg    58
                                                        Met Arg
                                                            1 ata ttt gct gtc ttt ata ttc atg acc tac tgg cat ttg ctg aac gca   106
Ile Phe Ala Val Phe Ile Phe Met Thr Tyr Trp His Leu Leu Asn Ala
        5                   10                  15 ttt act gtc acg gtt ccc aag gac cta tat gtg gta gag tat ggt agc   154
Phe Thr Val Thr Val Pro Lys Asp Leu Tyr Val Val Glu Tyr Gly Ser
        20                  25                  30 aat atg aca att gaa tgc aaa ttc cca gta gaa aaa caa tta gac ctg   202
Asn Met Thr Ile Glu Cys Lys Phe Pro Val Glu Lys Gln Leu Asp Leu
35                  40                  45                  50 gct gca cta att gtc tat tgg gaa atg gag gat aag aac att att caa   250
Ala Ala Leu Ile Val Tyr Trp Glu Met Glu Asp Lys Asn Ile Ile Gln
                55                  60                  65 ttt gtg cat gga gag gaa gac ctg aag gtt cag cat agt agc tac aga   298
Phe Val His Gly Glu Glu Asp Leu Lys Val Gln His Ser Ser Tyr Arg
            70                  75                  80 cag agg gcc cgg ctg ttg aag gac cag ctc tcc ctg gga aat gct gca   346
Gln Arg Ala Arg Leu Leu Lys Asp Gln Leu Ser Leu Gly Asn Ala Ala
        85                  90                  95

TABLE 1-continued

| | | | | | | | | | | | | | | | | |
|---|---|---|---|---|---|---|---|---|---|---|---|---|---|---|---|---|
| ctt | cag | atc | aca | gat | gtg | aaa | ttg | cag | gat | gca | ggg | gtg | tac | cgc | tgc | 394 |
| Leu | Gln | Ile | Thr | Asp | Val | Lys | Leu | Gln | Asp | Ala | Gly | Val | Tyr | Arg | Cys | |
| | 100 | | | | 105 | | | | | 110 | | | | | | |
| atg | atc | agc | tat | ggt | ggt | gcc | gac | tac | aag | cga | att | act | gtg | aaa | gtc | 442 |
| Met | Ile | Ser | Tyr | Gly | Gly | Ala | Asp | Tyr | Lys | Arg | Ile | Thr | Val | Lys | Val | |
| 115 | | | | | 120 | | | | 125 | | | | | | 130 | |
| aat | gcc | cca | tac | aac | aaa | atc | aac | caa | aga | att | ttg | gtt | gtg | gat | cca | 490 |
| Asn | Ala | Pro | Tyr | Asn | Lys | Ile | Asn | Gln | Arg | Ile | Leu | Val | Val | Asp | Pro | |
| | | | | 135 | | | | | 140 | | | | | 145 | | |
| gtc | acc | tct | gaa | cat | gaa | ctg | aca | tgt | cag | gct | gag | ggc | tac | ccc | aag | 538 |
| Val | Thr | Ser | Glu | His | Glu | Leu | Thr | Cys | Gln | Ala | Glu | Gly | Tyr | Pro | Lys | |
| | | | | 150 | | | | | 155 | | | | | 160 | | |
| gcc | gaa | gtc | atc | tgg | aca | agc | agt | gac | cat | caa | gtc | ctg | agt | ggt | aag | 586 |
| Ala | Glu | Val | Ile | Trp | Thr | Ser | Ser | Asp | His | Gln | Val | Leu | Ser | Gly | Lys | |
| | | 165 | | | | | 170 | | | | | 175 | | | | |
| acc | acc | acc | acc | aat | tcc | aag | aga | gag | gag | aag | ctt | ttc | aat | gtg | acc | 634 |
| Thr | Thr | Thr | Thr | Asn | Ser | Lys | Arg | Glu | Glu | Lys | Leu | Phe | Asn | Val | Thr | |
| | | 180 | | | | | 185 | | | | | 190 | | | | |
| agc | aca | ctg | aga | atc | aac | aca | aca | act | aat | gag | att | ttc | tac | tgc | act | 682 |
| Ser | Thr | Leu | Arg | Ile | Asn | Thr | Thr | Thr | Asn | Glu | Ile | Phe | Tyr | Cys | Thr | |
| 195 | | | | | 200 | | | | | 205 | | | | | 210 | |
| ttt | agg | aga | tta | gat | cct | gag | gaa | aac | cat | aca | gct | gaa | ttg | gtc | atc | 730 |
| Phe | Arg | Arg | Leu | Asp | Pro | Glu | Glu | Asn | His | Thr | Ala | Glu | Leu | Val | Ile | |
| | | | | 215 | | | | | 220 | | | | | 225 | | |
| cca | gaa | cta | cct | ctg | gca | cat | cct | cca | aat | gaa | agg | act | cac | ttg | gta | 778 |
| Pro | Glu | Leu | Pro | Leu | Ala | His | Pro | Pro | Asn | Glu | Arg | Thr | His | Leu | Val | |
| | | | | 230 | | | | | 235 | | | | | 240 | | |
| att | ctg | gga | gcc | atc | tta | tta | tgc | ctt | ggt | gta | gca | ctg | aca | ttc | atc | 826 |
| Ile | Leu | Gly | Ala | Ile | Leu | Leu | Cys | Leu | Gly | Val | Ala | Leu | Thr | Phe | Ile | |
| | | | | 245 | | | | | 250 | | | | | 255 | | |
| ttc | cgt | tta | aga | aaa | ggg | aga | atg | atg | gat | gtg | aaa | aaa | tgt | ggc | atc | 874 |
| Phe | Arg | Leu | Arg | Lys | Gly | Arg | Met | Met | Asp | Val | Lys | Lys | Cys | Gly | Ile | |
| | | | 260 | | | | | 265 | | | | | 270 | | | |
| caa | gat | aca | aac | tca | aag | aag | caa | agt | gat | aca | cat | ttg | gag | gag | acg | 922 |
| Gln | Asp | Thr | Asn | Ser | Lys | Lys | Gln | Ser | Asp | Thr | His | Leu | Glu | Glu | Thr | |
| 275 | | | | | 280 | | | | | 285 | | | | | 290 | |

| | |
|---|---|
| taatccagca ttggaacttc tgatcttcaa gcagggattc tcaacctgtg gtttaggggt | 982 |
| tcatcggggc tgagcgtgac aagaggaagg aatgggcccg tgggatgcag gcaatgtggg | 1042 |
| acttaaaagg cccaagcact gaaaatggaa cctggcgaaa gcagaggagg agaatgaaga | 1102 |
| aagatggagt caaacaggga gcctggaggg agaccttgat actttcaaat gcctgagggg | 1162 |
| ctcatcgacg cctgtgacag ggagaaagga tacttctgaa caaggagcct ccaagcaaat | 1222 |
| catccattgc tcatcctagg aagacgggtt gagaatccct aatttgaggg tcagttcctg | 1282 |
| cagaagtgcc ctttgcctcc actcaatgcc tcaatttgtt ttctgcatga ctgagagtct | 1342 |
| cagtgttgga acgggacagt atttatgtat gagttttttcc tatttatttt gagtctgtga | 1402 |
| ggtcttcttg tcatgtgagt gtggttgtga atgatttctt ttgaagatat attgtagtag | 1462 |
| atgttacaat tttgtcgcca aactaaactt gctgcttaat gatttgctca catctagtaa | 1522 |
| aacatggagt atttgtaaaa aaaaaaaaaa a | 1553 |

SEQ ID NO: 6 Human PD-L1M Amino Acid Sequence

| | | | | | | | | | | | | | | |
|---|---|---|---|---|---|---|---|---|---|---|---|---|---|---|
| Met | Arg | Ile | Phe | Ala | Val | Phe | Ile | Phe | Met | Thr | Tyr | Trp | His | Leu | Leu |
| 1 | | | | 5 | | | | | 10 | | | | | 15 | |
| Asn | Ala | Phe | Thr | Val | Thr | Val | Pro | Lys | Asp | Leu | Tyr | Val | Val | Glu | Tyr |
| | | | 20 | | | | | 25 | | | | | 30 | | |

TABLE 1-continued

```
Gly Ser Asn Met Thr Ile Glu Cys Lys Phe Pro Val Glu Lys Gln Leu
         35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  85

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
             115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                 165                 170                 175

Gly Lys Thr Thr Thr Thr Asn Ser Lys Arg Glu Glu Lys Leu Phe Asn
             180                 185                 190

Val Thr Ser Thr Leu Arg Ile Asn Thr Thr Asn Glu Ile Phe Tyr
             195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                 245                 250                 255

Phe Ile Phe Arg Leu Arg Lys Gly Arg Met Met Asp Val Lys Lys Cys
                 260                 265                 270

Gly Ile Gln Asp Thr Asn Ser Lys Lys Gln Ser Asp Thr His Leu Glu
             275                 280                 285

Glu Thr
    290
```

SEQ ID NO: 7 Human PD-L2 cDNA Acid Sequence

```
atg atc ttc ctc ctg cta atg ttg agc ctg gaa ttg cag ctt cac cag     48
Met Ile Phe Leu Leu Leu Met Leu Ser Leu Glu Leu Gln Leu His Gln
 1               5                  10                  15 ata gca gct tta ttc aca gtg aca gtc cct aag gaa ctg tac ata ata     96
Ile Ala Ala Leu Phe Thr Val Thr Val Pro Lys Glu Leu Tyr Ile Ile
             20                  25                  30 gag cat ggc agc aat gtg acc ctg gaa tgc aac ttt gac act gga agt    144
Glu His Gly Ser Asn Val Thr Leu Glu Cys Asn Phe Asp Thr Gly Ser
         35                  40                  45 cat gtg aac ctt gga gca ata aca gcc agt ttg caa aag gtg gaa aat    192
His Val Asn Leu Gly Ala Ile Thr Ala Ser Leu Gln Lys Val Glu Asn
 50                  55                  60 gat aca tcc cca cac cgt gaa aga gcc act ttg ctg gag gag cag ctg    240
Asp Thr Ser Pro His Arg Glu Arg Ala Thr Leu Leu Glu Glu Gln Leu
 65                  70                  75                  80 ccc cta ggg aag gcc tcg ttc cac ata cct caa gtc caa gtg agg gac    288
Pro Leu Gly Lys Ala Ser Phe His Ile Pro Gln Val Gln Val Arg Asp
                 85                  90                  95 gaa gga cag tac caa tgc ata atc atc tat ggg gtc gcc tgg gac tac    336
Glu Gly Gln Tyr Gln Cys Ile Ile Ile Tyr Gly Val Ala Trp Asp Tyr
                 100                 105                 110
```

TABLE 1-continued

```
aag tac ctg act ctg aaa gtc aaa gct tcc tac agg aaa ata aac act    384
Lys Tyr Leu Thr Leu Lys Val Lys Ala Ser Tyr Arg Lys Ile Asn Thr
        115                 120                 125 cac atc cta aag gtt cca gaa aca gat gag gta gag ctc acc tgc cag    432
His Ile Leu Lys Val Pro Glu Thr Asp Glu Val Glu Leu Thr Cys Gln
130                 135                 140 gct aca ggt tat cct ctg gca gaa gta tcc tgg cca aac gtc agc gtt    480
Ala Thr Gly Tyr Pro Leu Ala Glu Val Ser Trp Pro Asn Val Ser Val
145                 150                 155                 160 cct gcc aac acc agc cac tcc agg acc cct gaa ggc ctc tac cag gtc    528
Pro Ala Asn Thr Ser His Ser Arg Thr Pro Glu Gly Leu Tyr Gln Val
                165                 170                 175 acc agt gtt ctg cgc cta aag cca ccc cct ggc aga aac ttc agc tgt    576
Thr Ser Val Leu Arg Leu Lys Pro Pro Pro Gly Arg Asn Phe Ser Cys
            180                 185                 190 gtg ttc tgg aat act cac gtg agg gaa ctt act ttg gcc agc att gac    624
Val Phe Trp Asn Thr His Val Arg Glu Leu Thr Leu Ala Ser Ile Asp
        195                 200                 205 ctt caa agt cag atg gaa ccc agg acc cat cca act tgg ctg ctt cac    672
Leu Gln Ser Gln Met Glu Pro Arg Thr His Pro Thr Trp Leu Leu His
    210                 215                 220 att ttc atc ccc tcc tgc atc att gct ttc att ttc ata gcc aca gtg    720
Ile Phe Ile Pro Ser Cys Ile Ile Ala Phe Ile Phe Ile Ala Thr Val
225                 230                 235                 240 ata gcc cta aga aaa caa ctc tgt caa aag ctg tat tct tca aaa gac    768
Ile Ala Leu Arg Lys Gln Leu Cys Gln Lys Leu Tyr Ser Ser Lys Asp
                245                 250                 255 aca aca aaa aga cct gtc acc aca aca aag agg gaa gtg aac agt gct    816
Thr Thr Lys Arg Pro Val Thr Thr Thr Lys Arg Glu Val Asn Ser Ala
            260                 265                 270 atc                                                                819
Ile
```

SEQ ID NO: 8 Human PD-L2 Amino Acid Sequence

```
Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Gly Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175
```

TABLE 1-continued

```
Thr Ser Val Leu Arg Leu Lys Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
        210                 215                 220

Ile Phe Ile Pro Ser Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Lys Arg Glu Val Asn Ser Ala
            260                 265                 270

Ile
```

SEQ ID NO: 9 Human RGMb cDNA sequence

```
   1 atgataagga agaagaggaa gcgaagcgcg ccccccggcc catgccgcag ccacgggccc
  61 agacccgcca cggcgcccgc gccgccgccc tcgccggagc ccacgagacc tgcatggacg
 121 ggcatgggct tgagagcagc accttccagc gccgccgctg ccgccgccga ggttgagcag
 181 cgccgcagcc ccgggctctg ccccccgccg ctggagctgc tgctgctgct gctgttcagc
 241 ctcgggctgc tccacgcagg tgactgccaa cagccagccc aatgtcgaat ccagaaatgc
 301 accacggact tcgtgtccct gacttctcac ctgaactctg ccgttgacgg ctttgactct
 361 gagttttgca aggccttgcg tgcctatgct ggctgcaccc agcgaacttc aaaagcctgc
 421 cgtggcaacc tggtatacca ttctgccgtg ttgggtatca gtgacctcat gagccagagg
 481 aattgttcca aggatggacc cacatcctct accaaccccg aagtgaccca tgatccttgc
 541 aactatcaca gccacgctgg agccagggaa cacaggagag ggaccagaa ccctcccagt
 602 taccttttt gtggcttgtt tggagatcct cacctcagaa ctttcaagga taacttccaa
 661 acatgcaaag tagaaggggc ctggccactc atagataata attatctttc agttcaagtg
 721 acaaacgtac ctgtggtccc tggatccagt gctactgcta caaataagat cactattatc
 781 ttcaaagccc accatgagtg tacagatcag aaagtctacc aagctgtgac agatgacctg
 841 ccggccgcct ttgtggatgg caccaccagt ggtggggaca gcgatgccaa gagcctgcgt
 901 atcgtggaaa gggagagtgg ccactatgtg agatgcacg cccgctatat agggaccaca
 961 gtgtttgtgc ggcaggtggg tcgctacctg acccttgcca tccgtatgcc tgaagacctg
1021 gccatgtcct acgaggagag ccaggacctg cagctgtgcg tgaacggctg ccccctgagt
1081 gaacgcatcg atgacgggca gggccaggtg tctgccatcc tgggacacag cctgcctcgc
1141 acctccttgg tgcaggcctg gcctggctac acactggaga ctgccaacac tcaatgccat
1201 gagaagatgc cagtgaagga catctatttc cagtcctgtg tcttcgacct gctcaccact
1261 ggtgatgcca actttactgc cgcagcccac agtgccttgg aggatgtgga ggccctgcac
1321 ccaaggaagg aacgctggca cattttcccc agcagtggca atgggactcc ccgtggaggc
1381 agtgatttgt ctgtcagtct aggactcacc tgcttgatcc ttatcgtgtt tttgtag
```

SEQ ID NO: 10 Human RGMb Amino Acid Sequence

```
   1 mirkkrkrsa ppgpcrshgp rpatapappp spepTrpawt gmglraapss aaaaaaeveq
  61 rrspglcppp lellllllfs lgllhagdcq qpaqcriqkc ttdfvsitsh lnsavdgfds
 121 efckalraya gctqrtskac rgnlvyhsav lgisdlmsqr ncakdgptss tnpevthdpc
 181 nyhshagare hrrgdqnpps ylfcglfgdp hlrtfkdnfq tckveqawpl idnnylsvqv
```

TABLE 1-continued

```
241 tnvpvvpgss atatnkitii fkahhectdq kvyqavtddl paafvdgtts ggdsdakslr 301 iveresghyv emharyigtt vfvrqvgryl tlairmpedl amayeesqdl qlcvngcpls 361 eriddgqgqv sailghslpr tslvqawpgy tletantqch ekmpvkdiyf qscvfdlltt 421 gdanftaaah saledvealh prkerwhifp ssgngtprgg sdlsvslglt clilivfl
```

II. Methods of Treating Disorders Benefiting from: Upregulated Immune Responses a. Agents Useful for Upregulating Immune Responses

It is demonstrated herein that simultaneously inhibiting or blocking both RGMb and PD-1 function surprisingly to block the establishment and progression of malignancies (e.g., colorectal cancer) in animals. Thus, the agents of the present invention described herein that modulate the expression or activity of RGMb and PD-1, whether directly or indirectly, can upregulate immune responses.

Both RGMb and PD-1 are immune checkpoints/regulators. Thus, in one embodiment, agents that neutralize RGMb activity and PD-1 expression and/or activity can prevent inhibitory signaling and upregulate an immune response. In another embodiment, agents which directly block the interaction between RGMb and its natural receptor(s) like PD-L2, and PD-1 and its natural receptor(s) like PD-L1 and/or PD-L2 (e.g., anti-RGMb and anti-PD-1 blocking antibodies) can prevent inhibitory signaling and upregulate an immune response. Alternatively, agents that indirectly block the interaction between RGMb and its natural receptor(s), and PD-1 and its natural receptor(s) can prevent inhibitory signaling and upregulate an immune response. For example, soluble PD-L1 or soluble PD-L2, by binding to a PD-1 polypeptide indirectly reduces the effective concentration of PD-1 polypeptide available to bind molecules related to inhibited immune responses. Similarly, soluble PD-L2 or soluble BMPs, such as BMP-2 or BMP-4, by binding to an RGMb polypeptide indirectly redues the effective concentration of RGMb polypeptide available to bind molecules related to inhibited immune responses. Exemplary agents for upregulating an immune response include antibodies against RGMb and/or PD-1 that block the interaction between RGMb and its natural receptor(s) k and PD-1 and its natural receptor(s); a non-activating form of RGMb and/or PD-1 (e.g., a dominant negative polypeptide), small molecules or peptides that block the interaction between RGMb and its natural receptor(s), or PD-1 and its natural receptor(s); fusion proteins (e.g. the extracellular portion of RGMb or PD-1 fused to the Fc portion of an antibody or immunoglobulin) that bind to their natural receptor(s); nucleic acid molecules that block RGMb and/or PD-1 transcription or translation; and the like.

Additional agents useful in the methods of the present invention include antibodies, small molecules, peptides, peptidomimetics, natural ligands, and derivatives of natural ligands, that can either bind and/or inactivate or inhibit protein biomarkers of the invention, including the biomarkers listed in Table 1, or fragments thereof; as well as RNA interference, antisense, nucleic acid aptamers, etc. that can downregulate the expression and/or activity of the biomarkers of the invention, including the biomarkers listed in Table 1, or fragments thereof.

In one embodiment, isolated nucleic acid molecules that specifically hybridize with or encode one or more biomarkers of the invention, listed in Table 1 for example, or biologically active portions thereof. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecules corresponding to the one or more biomarkers listed in Table 1 or described herein can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., a lymphoma cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of one or more biomarkers listed in Table 1 or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence of one or more biomarkers listed in Table 1 or a portion thereof (i.e., 100, 200, 300, 400, 450, 500, or more nucleotides), can be isolated using standard molecular biology techniques and the sequence information provided herein. For example, a human cDNA can be isolated from a human cell line using all or portion of the nucleic acid molecule, or fragment thereof as a hybridization probe and standard hybridization techniques (i.e., as described in Sambrook, J., Fritsh, E. F., and Maniatis, T. *Molecular Cloning: A Laboratory Manual. 2nd, ed. Cold Spring Harbor Laboratory*, Cold Spring Harbor Laboratory Press, Cold Spring Harbor, N.Y., 1989). Moreover, a nucleic acid molecule encompassing all or a portion of the nucleotide sequence of one or more biomarkers listed in Table 1 or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence, or fragment thereof, can be isolated by the polymerase chain reaction using oligonucleotide primers designed based upon the sequence of the one or more biomarkers listed in Table 1, or fragment thereof, or the homologous nucleotide sequence. For example, mRNA can be isolated from muscle cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed according to well-known methods in the art. A nucleic acid of the invention can be amplified using cDNA or, alternatively, genomic DNA, as a template and appropriate oligonucleotide primers according to standard PCR amplification, techniques. The nucleic acid so amplified can be cloned into an appropriate vector and characterized by DNA sequence analysis. Furthermore, oligonucleotides corresponding to the nucleotide sequence of one or more biomarkers listed in Table 1 can be prepared by standard synthetic techniques, i.e., using an automated DNA synthesizer.

Probes based on the nucleotide sequences of one or more biomarkers listed in Table 1 can be used to detect or confirm the desired transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express one or more biomarkers listed in Table 1, such as by measuring a level of one or more biomarkers nucleic acid in a sample of cells from a subject, i.e., detecting mRNA levels of one or more biomarkers listed in Table 1.

Nucleic acid molecules encoding proteins corresponding to one or more biomarkers listed in Table 1, or portions thereof, from different species are also contemplated. For example, rat or monkey cDNA can be identified based on the nucleotide sequence of a human and/or mouse sequence and such sequences are well known in the art. In one embodiment, the nucleic acid molecule(s) of the invention encodes a protein or portion thereof which includes an amino acid sequence which is sufficiently homologous to an amino acid sequence of one or more biomarkers listed in Table 1, such that the protein or portion thereof modulates (e.g., enhance), one or more of the following biological activities: a) binding to the biomarker; b) modulating the copy number of the biomarker; c) modulating the expression level of the biomarker; and d) modulating the activity level of the biomarker.

As used herein, the language "sufficiently homologous" refers to proteins or portions thereof which have amino acid sequences which include a minimum number of identical or equivalent (e.g., an amino acid residue which has a similar side chain as an amino acid residue in one or more biomarkers listed in Table 1, or fragment thereof) amino acid residues to an amino acid sequence of the biomarker, or fragment thereof, such that the protein or portion thereof modulates (e.g., enhance) one or more of the following biological activities: a) binding to the biomarker; b) modulating the copy number of the biomarker; c) modulating the expression level of the biomarker; and d) modulating the activity level of the biomarker.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of the biomarker, or a fragment thereof.

Portions of proteins encoded by nucleic acid molecules of the one or more biomarkers listed in Table 1 are preferably biologically active portions of the protein. As used herein, the term "biologically active portion" of one or more biomarkers listed in Table 1 is intended to include a portion, e.g., a domain/motif, that has one or more of the biological activities of the full-length protein.

Standard binding assays, e.g., immunoprecipitations and yeast two-hybrid assays, as described herein, or functional assays, e.g., RNAi or overexpression experiments, can be performed to determine the ability of the protein or a biologically active fragment thereof to maintain a biological activity of the full-length protein.

The invention further encompasses nucleic acid molecules that differ from the nucleotide sequence of the one or more biomarkers listed in Table 1, or fragment thereof due to degeneracy of the genetic code and thus encode the same protein as that encoded by the nucleotide sequence, or fragment thereof. In another embodiment, an isolated nucleic acid molecule of the invention has a nucleotide sequence encoding a protein having an amino acid sequence of one or more biomarkers listed in Table 1, or fragment thereof or a protein having an amino acid sequence which is at least about 70%, 75%, 80%, 85%, 90%, 91%, 92%, 93%, 94%, 95%, 96%, 97%, 98%, 99% or more homologous to the amino acid sequence of the one or more biomarkers listed in Table 1, or fragment thereof. In another embodiment, a nucleic acid encoding a polypeptide consists of nucleic acid sequence encoding a portion of a full-length fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of the one or more biomarkers listed in Table 1 may exist within a population a mammalian and/or human population). Such genetic polymorphisms may exist among individuals within a population due to natural allelic variation. As used herein, the terms "gene" and "recombinant gene" refer to nucleic acid molecules comprising an open reading frame encoding one or more biomarkers listed in Table 1, preferably a mammalian, e.g., human, protein. Such natural allelic variations can typically result in 1-5% variance in the nucleotide sequence of the one or more biomarkers listed in Table 1. Any and all such nucleotide variations and resulting amino acid polymorphisms in the one or more biomarkers listed in Table 1 that are the result of natural allelic variation and that do not alter the functional activity of the one or more biomarkers listed in Table 1 are intended to be within the scope of the invention. Moreover, nucleic acid molecules encoding one or more biomarkers listed in Table 1 from other species.

In addition to naturally-occurring allelic variants of the one or more biomarkers listed in Table 1 that may exist in the population, the skilled artisan will, further appreciate that changes can be introduced by mutation into the nucleotide sequence, or fragment thereof, thereby leading to changes in the amino acid sequence of the encoded one or more biomarkers listed in Table 1, without altering the functional ability of the one or more biomarkers listed in Table 1. For example, nucleotide substitutions leading to amino acid substitutions at "non-essential" amino acid residues can be made in the sequence, or fragment thereof. A "non-essential" amino acid residue is a residue that can be altered from the wild-type sequence of the one or more biomarkers listed in Table 1 without altering the activity of the one or more biomarkers listed in Table 1, whereas an "essential" amino acid residue is required for the activity of the one or more biomarkers listed in Table 1. Other amino acid residues, however, (e.g., those that are not conserved or only semi-conserved between mouse and human) may not be essential for activity and thus are likely to be amenable to alteration without altering the activity of the one or more biomarkers listed in Table 1.

The comparison of sequences and determination of percent homology between two sequences can be accomplished using a mathematical algorithm, Preferably, tee alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4, For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (J. Mol. Biol. (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a protein homologous to one or more biomarkers listed in Table 1, or fragment thereof, can be created by introducing one or more nucleotide substitutions, additions or deletions into the nucleotide sequence, or fragment thereof, or a homologous nucleotide sequence such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side drains (e.g., lysine, arginine, histidine), acidic side chains (e.g., aspartic acid), glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in one or more biomarkers listed in Table 1 is preferably replaced with another amino acid residue from the same side chain family. Alternatively, in another embodiment, mutations can be introduced randomly along all or part of the coding sequence of the one or more biomarkers listed in Table 1, such as by saturation mutagenesis, and the resultant mutants can be screened for an activity described herein to identify mutants that retain desired activity. Following mutagenesis, the encoded protein can be expressed recombinantly according to well-known methods in the art and the activity of the protein can be determined using, for example, assays described herein.

The levels of one or more biomarkers listed in Table 1 may be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, the levels of one or more biomarkers listed in Table 1 are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomezynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof such as an oligonucleotide of at least 7, 15, 30, 50, 100, 250 or 500 nucleotides in length and sufficient to specifically hybridize under stringent conditions to a. mRNA or genomic DNA encoding one or more biomarkers listed in Table 1. Other suitable probes for use in the diagnostic assays of the invention are described herein. Hybridization of an mRNA with the probe indicates that one or more biomarkers listed in Table 1 is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Asymetrix™ gene chip array. A skilled artisan can readily adapt known mRNA detection methods for use in detecting the level of the one or more biomarkers listed in Table 1.

An alternative method for determining mRNA expression level in a sample involves the process of nucleic acid amplification, e.g., by RT-PCR (the experimental embodiment set forth in Mullis, 1987, U.S. Pat. No. 4,683,202), ligase chain reaction (Barany, 1991, *Proc. Natl. Acad. Sci. USA*, 88:189-193), self-sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al, 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the one or more biomarkers listed in Table 1.

As an alternative to making determinations based on the absolute expression level, determinations may be based on the normalized expression level of one or more biomarkers listed in Table 1. Expression levels are normalized by correcting the absolute expression level by comparing its expression to the expression of a non-biomarker gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal, sample, or between samples from different sources.

The level or activity of a protein corresponding to one or more biomarkers listed in Table 1 can also be detected and/or quantified by detecting or quantifying the expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), Immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express the biomarker of interest.

The present invention further provides soluble, purified and/or isolated polypeptide forms of one or more biomarkers listed in Table 1, or fragments thereof. In addition, it is to be understood that any and all attributes of the polypeptides described herein, such as percentage identities, polypeptide lengths, polypeptide fragments, biological activities, antibodies, etc. can be combined in any order or combination with respect to any biomarker listed in Table 1 and combinations thereof.

In one aspect, a polypeptide may comprise a full-length amino acid sequence corresponding to one or more biomarkers listed in Table 1 or a full-length amino acid sequence with 1 to about 20 conservative amino acid substitutions. An amino acid sequence of any described herein can also be at least 50, 55, 60, 65, 70, 75, 80, 85, 90, 91, 92, 93, 94, 95, 96, 97, 98, 99, or 99.5% identical to the full-length sequence of one or more biomarkers listed in Table 1, which is either described herein, well known in the art, or a fragment thereof. In another aspect, the present invention contemplates a composition comprising an isolated polypeptide corresponding to one or more biomarkers listed in Table 1 and less than about 25%, or alternatively 15%, or alternatively 5%, contaminating biological macromolecules or polypeptides.

The present invention further provides compositions related to producing, detecting, or characterizing such polypeptides, or fragment thereof, such as nucleic acids, vectors, host cells, and the like. Such compositions may serve as compounds that modulate the expression and/or activity of one or more biomarkers described herein or, for example, listed in Table 1.

An isolated polypeptide or a fragment thereof (or a nucleic acid encoding such a polypeptide) corresponding to one or more biomarkers of the invention, including the biomarkers listed in Table 1 or fragments thereof, can be used as an immunogen to generate antibodies that bind to said immunogen, using standard techniques for polyclonal and monoclonal antibody preparation according to well-known methods in the art. An antigenic peptide comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

In one embodiment, an antibody binds substantially specifically to PD-1 and inhibits or blocks its immunoinhibitory function, such as by interrupting its interaction with an inhibitory ligand like PD-L1 and/or PD-L2. In another embodiment, an antibody binds substantially specifically to RGMb and inhibits or blocks its immunoinhibitory function, such as by interrupting its interaction with PD-L2 and/or BMPs, such, as BMP-2 and/or BMP-4.

For example, a polypeptide immunogen typically is used to prepare antibodies by immunizing a suitable subject (e.g., rabbit, goat, mouse or other mammal) with the immunogen. A preferred animal is a mouse deficient in the desired target antigen. For example, a PD-1 knockout mouse if the desired antibody is an anti-PD-1 antibody, may be used. This results in a wider spectrum of antibody recognition possibilities as antibodies reactive to common mouse and human epitopes are not removed by tolerance mechanisms. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent, Immunization of a suitable subject with an immunogenic preparation induces a polyclonal antibody response to the antigenic peptide contained therein.

Polyclonal antibodies can be prepared as described above by immunizing a suitable subject with, a polypeptide immunogen. The polypeptide antibody titer in the immunized subject can be monitored over time by standard techniques, such, as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique (originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Etiological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well-known protocols used for fusing lymphocytes and immortalized cell lines can be applied for the purpose of generating a monoclonal antibody against one or more biomarkers of the invention, including the biomarkers listed in Table 1, or a fragment thereof (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present, invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that, bind the polypeptide. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791: Markland et al. International Publication No. WO 92/15679; Breitling et al International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology (NY)* 9:1369-1372; Hay et al. (1992) *Hum. Antibod. Hybridomas* 3:81-85; Muse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology (NY)* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Since it is well known in the art that antibody heavy and light chain CDR3 domains play a particularly important role in the binding specificity/affinity of an antibody for an antigen, the recombinant monoclonal antibodies of the present invention prepared as set forth above preferably comprise the heavy and light chain CDR3s of variable regions of the antibodies described herein and well known in the art. Similarly, the antibodies can further comprise the CDR2s of variable regions of said antibodies. The antibodies can further comprise the CDR1s of variable regions of said antibodies. In other embodiments, the antibodies can comprise any combinations of the CDRs.

The CDR1, 2, and/or 3 regions of the engineered antibodies described above can comprise the exact amino acid sequence(s) as those of variable regions of the present invention disclosed herein. However, the ordinarily skilled artisan will appreciate that some deviation from the exact CDR sequences may be possible while still retaining the ability of the antibody to bind a desired target, such as RGMb and/or PD-1 effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention described herein or otherwise publicly available.

The structural features of non-human or human antibodies (e.g., a rat anti-mouse/anti-human antibody) can be used to create structurally related human antibodies that retain at least one functional property of the antibodies of the present invention, such as binding to RGMb and/or PD-1. Another functional property includes inhibiting binding of the original known, non-human or human antibodies in a competition ELISA assay.

In some embodiments, monoclonal antibodies capable of binding and inhibiting/blocking RGMb and/or PD-1 are provided, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented herein or otherwise publicly available.

Similarly, monoclonal antibodies binding and inhibiting/blocking RGMb and/or PD-1, comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented herein or otherwise publicly available, are also provided.

Monoclonal antibodies capable of binding and inhibiting/blocking RGMb and/or PD-1, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented herein or otherwise publicly available; and comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented herein or otherwise publicly available, are also provided.

A skilled artisan will note that such percentage homology is equivalent to and can be achieved by introducing 1, 2, 3, 4, 5, 6, 7, 8, 9, 10, or more conservative amino acid substitutions within a given CDR.

The monoclonal antibodies of the present invention can comprise a heavy chain, wherein the variable domain comprises at least a CDR having a sequence selected from the group consisting of the heavy chain variable domain CDRs presented herein or otherwise publicly available and a light chain, wherein the variable domain comprises at least a CDR having a sequence selected from the group consisting of the light chain variable domain CDRs presented herein or otherwise publicly available.

Such monoclonal antibodies can comprise a light chain, wherein the variable domain comprises at least a CDR having a sequence selected from the group consisting of CDR-L1, CDR-L2, and CDR-L3, as described herein; and/or a heavy chain, wherein the variable domain comprises at least a CDR having a sequence selected from the group consisting of CDR-H1, CDR-H2, and CDR-H3, as described herein. In some embodiments, the monoclonal antibodies capable of binding human RGMb and/or PD-1 comprises or consists of CDR-L1, CDR-L2, CDR-L3, CDR-H1, CDR-H2, and CDR-H3, as described herein.

The heavy chain variable domain of the monoclonal antibodies of the present invention can comprise or consist of the vH amino acid sequence set forth herein or otherwise publicly available and/or the light chain variable domain of the monoclonal antibodies of the present invention can comprise or consist of the vκ amino acid sequence set forth herein or otherwise publicly available.

The present invention further provides fragments of said monoclonal antibodies which include, but are not limited to, Fv, Fab, F(ab')2, Fab', dsFv, scFv, sc(Fv)2 and diabodies; and multispecific antibodies formed from antibody fragments.

Other fragments of the monoclonal antibodies of the present invention are also contemplated. For example, individual immunoglobulin heavy and/or light chains are provided, wherein the variable domains thereof comprise at least a CDR presented herein or otherwise publicly available. In one embodiment, the immunoglobulin heavy chain comprises at least a CDR having a sequence that is at least 80%, 85%, 90%, 91%, 92%, 93%, 94%, 95%, 96%, 97%, 98%, 99%, 99.5% or 100% identical from the group of heavy chain or light chain variable domain CDRs presented herein or otherwise publicly available. In another embodiment, an immunoglobulin light chain comprises at least a CDR having a sequence that is at least 80%, 85%, 90%, 91%, 92%, 93%, 94%, 95%, 96%, 97%, 98%, 99%, 99.5% or 100% identical from the group of light chain or heavy chain variable domain CDRs presented herein or otherwise publicly available, are also provided.

In some embodiments, the immunoglobulin heavy and/or light chain comprises a variable domain comprising at least one of CDR-L1, CDR-L2, CDR-L3, CDR-H1, CDR-H2, or CDR-H3 described herein. Such immunoglobulin heavy chains can comprise or consist of at least one of CDR-H1, CDR-H2, and CDR-H3. Such immunoglobulin light chains can comprise or consist of at least one of CDR-L1, CDR-L2, and CDR-L3.

In other embodiments, an immunoglobulin heavy and/or light chain according to the present invention comprises or consists of a vH or vκ variable domain sequence, respectively, provided herein or otherwise publicly available.

The present invention further provides polypeptides which have a sequence selected from the group consisting of vH variable domain, vκ variable domain, CDR-L1, CDR-L2, CDR-L3, CDR-H1, CDR-H2, and CDR-H3 sequences described herein.

Antibodies, immunoglobulins, and polypeptides of the invention can be used in an isolated (e.g., purified) form or contained in a vector, such as a membrane or lipid vesicle (e.g. a liposome).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Modifications and changes may be made in the structure of the antibodies described herein, and in the DNA sequences encoding them, and still obtain a functional molecule that encodes an antibody and polypeptide with desirable characteristics. For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (<RTI 3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr et al. (1987) and by Edge et al. (1981). Enzymatic cleavage of carbohydrate moieties on antibodies can be achieved by the use of a variety of endo- and exo-glycosidases as described by Thotakura et al. (1987).

Other modifications can involve the formation of immunoconjugates. For example, in one type of covalent modification, antibodies or proteins are covalently linked to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Conjugation of antibodies or other proteins of the present invention with heterologous agents can be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamide), bis-diazonium derivatives (such as bis-(p-diazoniumbenzoyl)-ethylenediamine), diisocyanates (such as toluene 2,6diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features antibodies conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorabicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a related disorder, such as a cancer.

Conjugated antibodies, in addition to therapeutic utility, can be useful for diagnostically or prognostically to monitor polypeptide levels in tissue as part of a clinical testing procedure, e.g., to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}$I, $^{131}$I, $^{35}$S, or $^{3}$H.

[0134] As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

The antibody conjugates of the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, Pseudomonas exotoxin, or diphtheria toxin; a protein such as tumor necrosis factor or interferon-.gamma; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss, Inc. 1985); Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

In some embodiments, conjugations can be made using a "cleavable linker" facilitating release of the cytotoxic agent or growth inhibitory agent in a cell. For example, an acid-labile linker, peptidase-sensitive linker, photolabile linker, dimethyl linker or disulfide-containing linker (See e.g. U.S. Pat. No. 5,208,020) may be used. Alternatively, a fusion protein comprising the antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

Additionally, recombinant polypeptide antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184, 187; Taniguchi, M. European Patent Application 171, 496; Morrison et al. European Patent Application 173,494; Neuberger et al. PCT Application WO 86/01533; Cabilly et al U.S. Pat. No. 4,816,567; Cabilly et al. European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. 84:214-218; Nishimura et al. (1987) Cancer Res. 47:999-1005; Wood et al. (1985) Nature 314:446-449; Shaw et al. (1988) J. Natl. Cancer Inst. 80:1553-1559): Morrison, S. L, (1985) Science 229:1202-1207; Oi et al. (1986) Biotechniques 4:214; Winter U.S. Pat. No. 5,225,539; Jones et al. (1986) Nature 321:552-525; Verhocyan et al. (1988) Science 239:1534; and Beidler et al. (1988) J. Immunol. 141:4053-4060.

In addition, humanized antibodies can be made according to standard protocols such, as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 3,871,907, or 5,733,743. The use of intracellular antibodies to inhibit protein function in a cell is also known in the art (see e.g., Carlson, J. R. (1988) Mol. Cell. Biol. 8:2638-2646; Biocca, S. et al. (1990) EMBO J. 9:101-108; Werge, T. M. et al. (1990) FEBS Lett. 274:193-198; Carlson, J. R, (1993) Proc. Natl. Acad Sci. USA 90:7427-7428; Marasco, W. A. et al. (1993) Proc. Natl. Acad. Sci. USA 90:7889-7893; Biocca, S. et al. (1994) Biotechnology (NY) 12:396-399; Chen, S-Y, et al. (1994) Hum. Gene Ther. 5:595-601; Duan, L et al. (1994) Proc. Natl. Acad. Sci. USA 91:5015-5079; Chen, S-Y. et al. (1994) Proc. Natl. Acad. Sci. USA 93:5932-5936; Beerli, R. R. et al. (1994) J. Biol. Chem. 269:23931-23936; Beerli, R. R. et al. (1994) Biochem. Biophys. Res. Commun. 204:666-672; Mhashilkar, A. M. et al. (1995) EMBO J. 14:1542-1551; Richardson, J. H. et al. (1995) Proc. Natl. Acad. Sci. USA 92:3137-3141; PCT Publication No. WO 94/02610 by Marasco et al.; and PCT Publication No. WO 95/03832 by Duan et al.).

Additionally, fully human antibodies could be made against biomarkers of the invention, including the biomarkers listed in Table 1, or fragments thereof. Fully human antibodies can be made in mice that are transgenic for human immunoglobulin genes, e.g. according to Hogan, et al., "Manipulating the Mouse Embryo: A Laboratory Manuel," Cold Spring Harbor Laboratory. Briefly, transgenic mice are immunized with purified immunogen. Spleen cells are harvested and fused to myeloma cells to produce hybridomas. Hybridomas are selected based on their ability to produce antibodies which bind to the immunogen. Fully human antibodies would reduce the immunogenicity of such antibodies in a human.

In one embodiment, an antibody for use in the instant invention is a bispecific or multispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) Nature 314:628, and Perez et al. (1985) Nature 316:354) and hybridoma technology (Staerz and Bevan (1986) Proc. Natl. Acad. Sci. USA, 83:1453, and Staerz and Bevan (1986) Immunol. Today 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a polypeptide or a fragment thereof of one or more biomarkers of the invention, including one or more biomarkers listed in Table 1, or a fragment thereof. In one embodiment, the bispecific antibody could specifically bind to both a polypeptide or a fragment thereof and its natural binding partner(s) or a fragment(s) thereof.

In another aspect of this invention, peptides or peptide mimetics can be used to antagonize the activity of one or more biomarkers of the invention, including one or more biomarkers listed in Table 1, or a fragment(s) thereof, in one embodiment, variants of one or more biomarkers listed in Table 1 which function as a modulating agent for the respective full length protein, can be identified by screening combinatorial libraries of mutants, e.g., truncation mutants, for antagonist activity. In one embodiment, a variegated library of variants is generated by combinatorial mutagenesis at the nucleic acid level and is encoded by a variegated gene library. A variegated library of variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1.056; Ike et. al. (1983) Nucleic Acid Res. 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of interest (Arkin and Youvan (1992) Proc. Natl. Acad. Sci. USA 89:7811-7815; Delagrave et al. (1993) Protein Eng. 6(3): 327-331). In one embodiment, cell based assays can be exploited to analyze a variegated polypeptide library. For example, a library of expression vectors can be transfected into a cell line which ordinarily synthesizes one or more biomarkers of the invention, including one or more biomarkers listed in Table 1, or a fragment thereof. The transfected cells are then cultured such that the foil length polypeptide and a particular mutant polypeptide are produced and the effect of expression of the mutant on the full length polypeptide activity in cell supernatant can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) Annu. Rev. Biochem. 61:387, incorporated herein by reference); for example, by adding internal cysteine residues capable of forming intramolecular disulfide bridges which cyclize the peptide.

The amino acid sequences disclosed, herein will enable those of skill in the art to produce polypeptides corresponding peptide sequences and sequence variants thereof. Such polypeptides can be produced in procaryotic or eukaryotic host cells by expression of polynucleotides encoding the peptide sequence, frequently as part, of a larger polypeptide. Alternatively, such peptides can be synthesized by chemical methods. Methods for expression of heterologous proteins in recombinant hosts, chemical synthesis of polypeptides, and in vitro translation are well known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E, (1980) *Semisynthetic Proteins*, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used therapeutically to treat disease, e.g., by altering costimulation in a patient.

Peptidomimetics (Fauchere (1986) *Adv. Drug Res.* 15:29; Veber and Freidinger (1985) TINS p. 392; and Evans et. al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of:—CH2NH—, —CH2S—, —CH2-CH2-, —CH=CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F. Vega Data (March 1983), Vol. 1, Issue 3, "Peptide Backbone Modifications" (general review); Moriey, J. S. (1980) *Trends Pharm. Sci.* pp. 463-468 (general review): Hudson, D. et al. (1979) *Int. J. Pept. Prot. Res.* 14:177-185 (—CH2NH—, CH2CH2-); Spatola, A. F. et al. (1986) *Life Sci.* 38:1243-1249 (—CH2-S); Hann, M. M. (1982), *J. Chem. Soc. Perkin Trans.* 1. 307-314 (—CH—CH—, cis and trans); Almquist, R. G. et al. (190) *J. Med. Chem.* 23:1392-1398 (—COCH2-); Jennings-White, C. et al. (1982) *Tetrahedron Lett* 23:2533 (—COCH2-); Szelke, M. et al. European Appln. EP 45665 (1982) CA: 97:39405 (1982)(—CH(OH) CH2-); Holladay, M. W. et al. (1983) *Tetrahedron Lett.* (1983) 24:4401-4404 (—C(OH)CH2-); and Hruby, V. J. (1982) *Life Sci.* (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivatization (e.g., labeling) of peptidomimetics should not substantially interfere with the desired biological or pharmacological activity of the peptidomimetic.

Also encompassed by the present invention are small molecules which can modulate (either enhance or inhibit) interactions, e.g., between biomarkers described herein or listed in Table 1 and their natural binding partners. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anticancer Drug Des.* 12:145).

Examples of methods for the synthesis of molecular libraries can be found in the art, for example in; DeWiit et al. (1993) *Proc. Natl. Acad. Sci. USA* 90:6909; Erb et al. (1994) *Proc. Natl. Acad Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382): (Felici (1991) *J. Mol. Biol.* 222:301-310); (Ladner supra.). Compounds can be screened in cell based or non-cell based assays. Compounds can be screened in pools (e.g. multiple compounds in each testing sample) or as individual compounds.

The invention also relates to chimeric or fusion proteins of the biomarkers of the invention, including the biomarkers listed in Table 1, or fragments thereof. As used herein, a "chimeric protein" or "fusion protein" comprises one or more biomarkers of the invention, including one or more biomarkers listed in Table 1, or a fragment thereof, operatively linked to another polypeptide having an amino acid sequence corresponding to a protein which is not substantially homologous to the respective biomarker. In a preferred embodiment, the fission protein comprises at least one biologically active portion of one or more biomarkers of the invention, including one or more biomarkers listed in Table 1, or fragments thereof. Within the fusion protein, the term "operatively linked" is intended to indicate that the biomarker sequences and the non-biomarker sequences are fused in-frame to each other in such a way as to preserve functions exhibited when expressed independently of the fusion. The "another" sequences can be fused to the N-terminus or C-terminus of the biomarker sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. In another preferred embodiment, the first peptide consists of a portion of a biologically active molecule (e.g. the extracellular portion of the polypeptide or the ligand binding portion). The second peptide can include an immunoglobulin constant region, for example, a human Cγ1 domain, or Cγ4 domain (e.g., the hinge, CH2 and CH3 regions of human IgCγ1, or hitman IgCγ4, see e.g., Capon, et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transacting host cells and purifying proteins and peptides are known in the art.

Preferably, a fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992).

Particularly preferred Ig fusion proteins include the extracellular domain portion or variable region-like domain of RGMb, PD-1, or other biomarker listed in Table 1, coupled to an immunoglobulin constant region (e.g., the Fc region). The immunoglobulin constant region may contain genetic modifications which reduce or eliminate effector activity inherent in the immunoglobulin structure. For example, DNA encoding the extracellular portion of a polypeptide of interest can be joined to DNA encoding the hinge, CH2 and CH3 regions of human IgGγ1 and/or IgGγ4 modified by site directed mutagenesis, e.g., as taught in WO 97/28267.

In another embodiment, the fusion protein contains a heterologous signal sequence at its N-terminus. In certain host cells (e.g., mammalian host cells), expression and/or secretion of a polypeptide can be increased through use of a heterologous signal sequence.

The fusion proteins of the invention can be used as immunogens to produce antibodies in a subject. Such antibodies may be used to purify the respective natural polypeptides from which the fusion proteins were generated, or in screening assays to identify polypeptides which inhibit the interactions between one or more biomarkers polypeptide or a fragment thereof and its natural binding partner(s) or a fragment(s) thereof.

Also provided herein are compositions comprising one or more nucleic acids comprising or capable of expressing at least 1, 2, 3, 4, 5, 10, 20 or more small nucleic acids or antisense oligonucleotides or derivatives thereof wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers of the invention, including one or more biomarkers listed in Table 1, or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least, six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g. cancer cell proliferation inhibition, induction of cancer cell apoptosis, enhancement of cancer cell susceptibility to chemotherapeutic agents, specific miRNA target inhibition). In some embodiments, a functional variant, of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nueleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the worldwide web at microma.sanger.ae.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences of the invention may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin.

In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, anti-miRNA, or a miRNA binding site, or a variant thereof. For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002) *Mol. Cell* 9:1327-1333; Tuschl (2002), *Nat. Biotechnol* 20:446-448; Brummelkamp et al. (2002) *Science* 296:550-553; Miyagishi et al. (2002) *Nat. Biotechnol.* 20:497-500; Paddison et al. (2002) *Genes Dev.* 16:948-958; Lee et al. (2002) *Nat. Biotechnol.* 20:500-505; and Paul et al. (2002) *Nat. Biotechnol.* 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, For example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to biomarkers listed in Table 1). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner (1994) *Nature* 372:

333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic, acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and non-specific biological effects of oligonucleotides. In another embodiment these studies compare levels of the target nucleic acid or protein with that of an internal control nucleic acid or protein. Additionally, it is envisioned that results obtained using fee antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides cam be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. U.S.A. 84:648-652: PCT Publication No. WO88/09810) or the blood-brain barrier (see, e.g., PCT Publication No. WO89/10134), hybridization-triggered cleavage agents. (See, e.g., Krol et al. (1988) BioTech. 6:958-976) or intercalating agents. (See, e.g., Zon (1988) Pharm. Res. 5:539-549). To this end, small nucleic acids and/or antisense oligonucleotides may be conjugated to another molecule, e.g., a peptide, hybridization, triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxyti-ethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methyl-aminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes, in certain embodiments, a conjugate group is attached directly to the oligonucleotide, in certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidom-ethyl) cyclohexane-1-carboxylate (SMCC), 6-amino-hexanoic acid (AHEX or AHA), substituted C1-C10 alkyl, substituted or unsubstituted C2-C10 alkenyl, and substituted or unsubstituted C2-C10 alkynyl. In certain such embodiments, a subsistent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such, as, for example, nuclease stability. Included in stabilizing groups are cap structures. These terminal modifications protect the oligonucleotide from exonuelease degradation, and can help in delivery and/or localization within a cell. The cap can be present at the 5-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5-amino-alkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5-amino, a bridging and/or non-bridging 5-phosphoramidate, a phosphorothioate, and a 5'-mercapto moiety.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl.

Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-0-methylribonucleotide (Inoue et al. (1987) Nucl. Acids Res. 15:6131-6148), or a chimeric RNA-DNA analogue (Inoue et al. (1987) FEBS Lett. 215: 327-330).

Small nucleic acids and/or antisense oligonucleotides of the methods and compositions presented herein may be synthesized by standard methods known in the art, e.g., by use of an automated DNA synthesizer (such as are commercially available from Bioseareh, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmaeon Research (Lafayette, Colo., USA), Pierce Chemical (part of Perbio Science, Rockford, Ill., USA), Glen Research (Sterling, Va., USA), ChemGenes (Ashland, Mass., USA), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g. mRNAs) sequences mediate degradation or in which sequences incompletely complementary to cellular nucleic acids (e.g., mRNAs) mediate translational repression when expressed within cells, or piwiRNAs. In another embodiment, double stranded siRNAs can be processed into single stranded antisense RNAs that bind single stranded cellular RNAs (e.g., microRNAs) and inhibit their expression, RNA interference (RNAi) is the process of sequence-specific, post-transcriptional gene silencing in animals and plants, initiated by double-stranded RNA (dsRNA) that is homologous in sequence to the silenced gene, in vivo, long dsRNA is cleaved by ribonuclease III to generate 21- and 22-nucleotide siRNAs, it has been shown that 21-nucleotide siRNA duplexes specifically suppress expression of endogenous and heterologous genes in different mammalian cell lines, including human embryonic kidney (293) and HeLa cells (Elbashir et al. (2001) Nature 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) RNA 8:842; Xia et al. (2002) Nature Biotechnology 20:1006; and Brummelkamp et al. (2002) Science 296:550). Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) Science 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods presented herein also include RNA endoribonucleases (hereinafter "Cech-type ribozymes") such as the one which occurs naturally in Tetrahymena thermophila (known as the IVS, or L-19IVS RNA) and which has been extensively described by Thomas Cech and collaborators (Zaug et al. (1984) Science 224:574-578; Zaug et al. (1986) Science 231:470-475; Zaug et al. (1986) Nature 324:429-433; WO 88/04300; and Been et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleolides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in viva transcription of DNA sequences encoding the antisense RNA molecule. Such DNA sequences may be incorporated into a wide variety of vectors which incorporate suitable RNA polymerase promoters such as the 17 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that polypeptides, small nucleic acids, and antisense oligonucleotides can be further linked to another peptide or polypeptide (e.g., a heterologous peptide), e.g., that, serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g., antibodies, small molecules, peptides, fusion proteins, or small nucleic acids) can be incorporated into pharmaceutical compositions and administered to a subject in vivo. The compositions may contain a single such molecule or agent or any combination of agents described herein. "Single active agents" described herein can be combined with other pharmacologically active compounds ("second active agents") known in the art according to the methods and compositions provided herein.

b. Pharmaceutical Compositions

Agents that inhibit or block RGMb and PD-1 expression and/or activity, including, e.g., blocking antibodies, peptides, fusion proteins, or small molecules, can be incorporated into pharmaceutical compositions suitable for administration to a subject. Such compositions typically comprise the antibody, peptide, fusion protein or small molecule and a pharmaceutical acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringeability exists. It must be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent, or an edible carrier. They can be enclosed in gelatin capsules or compressed into tablets, for the purpose of oral therapeutic administration, the active compound can be incorporated with excipients and used in the form of tablets, troches, or capsules. Oral compositions can also be prepared using a fluid earner for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, modulatory agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by, and directly dependent on, the unique characteristics of the active compound, the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50, Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The above described modulating agents may be administered it he form of expressible nucleic acids which encode said agents. Such nucleic acids and compositions in which they are contained, are also encompassed by the present invention. For instance, the nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen, et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

c. Prophylactic Methods

In one aspect, the present invention provides a method for preventing in a subject, a cancer, such as a hematologic cancer like multiple myeloma, associated with a less than desirable immune response. Subjects at risk for such a disease can be identified, for example, by any or a combination of diagnostic or prognostic assays known in the art. Administration of a prophylactic agent(s) can occur prior to the manifestation of symptoms associated with an unwanted or less than desirable immune response. The appropriate agent(s) used for treatment (e.g. antibodies, peptides, fusion proteins or small molecules) can be determined based on clinical indications and can be identified using diagnostic assays well known in the art, as well as those described herein.

d. Therapeutic Methods

Another aspect of the invention pertains to therapeutic methods of modulating an immune response, e.g., by inhibiting or blocking the expression and/or activity of RGMb and PD-1.

Modulatory methods of the present invention involve contacting a cell, such as an immune cell with an agent that inhibits or blocks the expression and/or activity of RGMb and PD-1. Exemplary agents useful in such methods are described above. Such agents can be administered in vitro or ex vivo (e.g., by contacting the cell with the agent) or, alternatively, in vivo (e.g., by administering the agent to a subject). As such, the present invention provides methods useful for treating an individual afflicted with a condition that would benefit from an increased immune response, such as an infection or a cancer like colorectal cancer.

Agents that upregulate immune responses can be in the form of enhancing an existing immune response or eliciting an initial immune response. Thus, enhancing an immune response using the subject compositions and methods is useful for treating cancer, but can also be useful for treating an infectious disease (e.g., bacteria, viruses, or parasites), a parasitic infection, and an immunosuppressive disease.

Exemplary infectious disorders include viral skin diseases, such as Herpes or shingles, in which case such an agent can be delivered topically to the skin. In addition, systemic viral diseases, such as influenza, the common cold, and encephalitis might be alleviated by systemic administration of such agents, in one preferred embodiment, agents that upregulate the immune response described herein are useful for modulating the arginase/NOS balance during *Trypanosoma cruzi* infection in order to facilitate a protective immune response against the parasite.

Immune responses can also be enhanced in an infected patient through an ex vivo approach, for instance, by removing immune cells from the patient, contacting immune cells in vitro with an agent described herein and reintroducing the in vitro stimulated immune cells into the patient.

In certain instances, it may be desirable to further administer other agents that upregulate immune responses, for example, forms of other B7 family members that transduce signals via costimulatory receptors, in order to further augment the immune response. Such additional agents and therapies are described further below.

Agents that upregulate an immune response can be used prophylactically in vaccines against various polypeptides (e.g., polypeptides derived from pathogens). Immunity against a pathogen (e.g., a virus) can be induced by vaccinating with a viral protein along with an agent that upregulates an immune response, in an appropriate adjuvant.

In another embodiment, upregulation or enhancement of an immune response function, as described herein, is useful in the induction of tumor immunity.

In another embodiment, the immune response can be stimulated by the methods described herein, such that pre-existing tolerance, clonal deletion, and/or exhaustion (e.g., T cell exhaustion) is overcome. For example, immune responses against antigens to which a subject cannot mount a significant immune response, e.g., to an autologous antigen, such as a tumor specific antigens can be induced by administering appropriate agents described herein that upregulate the immune response. In one embodiment, an autologous antigen, such as a tumor-specific antigen, can be coadministered. In another embodiment, the subject agents can be used as adjuvants to boost responses to foreign antigens in the process of active immunization.

In one embodiment, immune cells are obtained from a subject and cultured ex vivo in the presence of an agent as described herein, to expand the population of immune cells and/or to enhance immune cell activation. In a further embodiment the immune cells are then administered to a subject. Immune cells can be stimulated in vitro by, for example, providing to the immune cells a primary activation signal and a costimulatory signal, as is known in the art. Various agents can also be used to costimulate proliferation of immune cells. In one embodiment immune cells are cultured ex vivo according to the method described in PCT Application No. WO 94/29436. The costimulatory polypeptide can be soluble, attached to a cell membrane, or attached to a solid surface, such as a bead.

In still another embodiment, agents described herein useful for upregulating immune responses can further be linked, or operatively attached, to toxins using techniques that are known in the art, e.g., crosslinking or via recombinant DNA techniques. Such agents can result in cellular destruction of desired cells. In one embodiment, a toxin can be conjugated to an antibody, such as a bispecific antibody. Such antibodies are useful for targeting a specific cell population, e.g., using a marker found only on a certain type of cell. The preparation of immunotoxins is, in general well known in the art (see, e.g., U.S. Pat. No. 4,340,535, and EP 44167). Numerous types of disulfide-bond containing linkers are known which can successfully be employed to conjugate the toxin moiety with a polypeptide. In one embodiment, linkers that contain a disulfide bond that is sterically "hindered" are preferred, due to their greater stability in vivo, thus preventing release of the toxin, moiety prior to binding at the site of action. A wide variety of toxins are known that may be conjugated to polypeptides or antibodies of the invention. Examples include: numerous useful plant-, fungus- or even bacteria-derived toxins, which, by way of example, include various A chain toxins, particularly ricin A chain, ribosome inactivating proteins such as saporin or gelonin, α-sarcin, aspergillin, restrictocin, ribonucleases, such as placental ribonuclease, angiogenic, diphtheria toxin, and *Pseudomonas* exotoxin, etc. A preferred toxin moiety for use in connection with the invention is toxin A chain which has been treated to modify or remove carbohydrate residues, deglycosylated A chain, (U.S. Pat. No. 5,776,427). Infusion of one or a combination of such cytotoxic agents, (e.g., ricin fusions) into a patient may result in the death of immune cells.

In another embodiment, certain combinations work synergistically in the treatment of conditions that would benefit from the modulation of immune responses. Second active agents can be large molecules (e.g., proteins) or small molecules (e.g., synthetic inorganic, organometallic, or organic molecules). For example, anti-RGMb and anti-PD-1 antibodies can be further combined with other agents or therapies useful in treating a condition of interest, such the combination of additional immune checkpoint inhibitors, such as anti-PD-L1, anti-PD-L2, anti-CTLA4, etc. antibodies or combinations thereof.

In one embodiment, anti-cancer immunotherapy is administered in combination to subjects described herein. The term "immunotherapy" refers to any therapy that acts by targeting immune response modulation (e.g., induction, enhancement, suppression, or reduction of an immune response). In certain embodiments, immunotherapy is administered that activates T cells that recognize nonantigen (e.g., mutants that change the normal protein coding sequence and can be processed by the antigen presentation system, bind to MHC and recognized as foreign by T cells).

The term "immune response" includes T cell-mediated and/or B cell-mediated immune responses. Exemplary immune responses include T cell responses, e.g., cytokine production and cellular cytotoxicity. In addition, the term "immune response" includes immune responses that are indirectly effected by T cell activation, e.g., antibody production (humoral responses) and activation of cytokine responsive cells, e.g., macrophages. The term "inhibit" includes the decrease, limitation, or blockage, of, for example a particular action, function, or interaction, in some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented. The term "promote" has the opposite meaning.

The term "immunotherapeutic agent" can include any molecule, peptide, antibody or other agent which can modulate a host immune system in response to an antigen, such as expressed by a tumor or cancer in the subject. Immunotherapeutic strategies include administration of vaccines, antibodies, cytokines, chemokines, as well as small molecular inhibitors, anti-sense oligonucleotides, and gene therapy, as described further below (see, for example, Mocellin et al. (2002) Cancer Immunol. Immunother. 51:583-595; Dy et al. (2002) J. Clin. Oncol 20: 2881-2894).

Immunotherapies that are designed to elicit or amplify an immune response are referred to as "activation immunotherapies." Immunotherapies that are designed to reduce or suppress an immune response are referred to as "suppression immunotherapies." Any agent believed to have an immune system effect on the genetically modified transplanted cancer cells can be assayed to determine whether the agent is an immunotherapy and the effect that a given genetic modification has on the modulation of immune response. In some embodiments, the immunotherapy is cancer cell-specific. In some embodiments, immunotherapy can be "untargeted," which refers to administration of agents that do not selectively interact with immune system cells, yet modulates immune system function. Representative examples of untargeted therapies include, without limitation, chemotherapy, gene therapy, and radiation therapy.

Immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

In one embodiment immunotherapy comprises adoptive cell-based immunotherapies. Well known adoptive cell-based immunotherapeutic modalities, including, without limitation. Irradiated autologous or allogeneic tumor cells, tumor lysates or apoptotic tumor cells, antigen-presenting cell-based immunotherapy, dendritic cell-based immunotherapy, adoptive T cell transfer, adoptive CAR. T cell therapy, autologous immune enhancement therapy (AIET), cancer vaccines, and/or antigen presenting cells. Such cell-based immunotherapies can be further modified to express one or more gene products to further modulate immune responses, such as expressing cytokines like GM-CSF, and/or to express tumor-associated antigen (TAA) antigens, such as Mage-1, gp-100, patient-specific neoantigen vaccines, and the like.

In another embodiment, immunotherapy comprises non-cell-based immunotherapies. In one embodiment, compositions comprising antigens with or without vaccine-enhancing adjuvants are used. Such compositions exist in many well known forms, such as peptide compositions, oncolytic viruses, recombinant antigen comprising fusion proteins, and the like, in still another embodiment, immunomodulatory interleukins, such as IL-2, IL-6, IL-7, IL-12, IL-17, IL-23, and the like, as well as modulators thereof (e.g., blocking antibodies or more potent, or longer lasting forms) are used. In yet another embodiment, immunomodulatory cytokines, such as interferons, G-CSF, imiquimod, TNFalpha, and the like, as well as modulators thereof (e.g., blocking antibodies or more potent or longer lasting forms) are used. In another embodiment, immunomodulatory chemokines, such as CCL3, CCL26, and CXCL7, and the like, as well as modulators thereof (e.g., blocking antibodies or more potent, or longer lasting forms) are used. In another embodiment, immunomodulatory molecules targeting immunosuppression, such as STAT3 signaling modulators, NFkappaB signaling modulators, and immune checkpoint modulators, are used. The terms "immune checkpoint" and "anti-immune checkpoint therapy" are described above.

In still another embodiment, immunomodulatory drugs, such as immunocytostatic drugs, glucocorticoids, cytostatics, immunophilins and modulators thereof (e.g., rapamycin, a calcineurin inhibitor, tacrolimus, ciclosporin (cyclosporin), pimecrolimus, abetimus, gusperimus, ridaforolimus, everolimus, temsirolimus, zotarolimus, etc.), hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (doca) aldosterone, a non-glucocorticoid steroid, a pyrimidine synthesis inhibitor, leflunomide, teriflunomide, a folic acid analog, methotrexate, anti-thymocyte globulin, anti-lymphocyte globulin, thalidomide, lenalidomide, pentoxifylline, bupropion, curcumin, catechin, an opioid, an IMPDH inhibitor, mycophenolic acid, myriocin, fingolimod, an NF-xB inhibitor, raloxifene, drotrecogin alia, denosumab, an NF-xB signaling cascade inhibitor, disulfiram, olmesartan, dithiocarbamate, a proteasome inhibitor, bortezomib, MG132, Prol, NPI-0052, curcumin, genistein, resveratrol, parthenolide, thalidomide, lenalidomide, flavopiridol non-steroidal anti-inflammatory drugs (NSAIDs), arsenic trioxide, dehydroxymethylepoxyquinomycin (DHMEQ), I3C(indole-3-carbinol)/DIM(di-indolmethane) (13C/DIM), Bay 11-7082, luteolin, cell permeable peptide SN-50, IKBa-super repressor overexpression, NFKB decoy oligodeoxynucleotide (ODN), or a derivative or analog of any thereo, are used. In yet another embodiment, immunomodulatory antibodies or protein are used. For example, antibodies that bind to CD40, Toll-like receptor (TLR), OX40, GITR, CD27, or to 4-IBB, T-cell bispecific antibodies, an anti-IL-2 receptor antibody, an anti-CD3 antibody, OKT3 (muromonab), otelixtzumab, teplizumab, visilizumab, an anti-CD4 antibody, elenoliximab, keliximab, zanolimumab, an anti-CD11 a antibody, efalizumab, an anti-CD18 antibody, erlizumab, rovelizumab, an anti-CD20 antibody, afutuzumab, ocreltzumab, ofatumumab, pascolizumab, rituximab, an anti-CD23 antibody, lumiliximab, an anti-CD40 antibody, teneliximab, toralizumab, an anti-CD40L antibody, ruplizumab, an anti-CD62L antibody, aselizumab, an anti-CD80 antibody, galiximab, an anti-CD147 antibody, gavilimomab, a B-Lymphocyte stimulator (BLyS) inhibiting antibody, belimumab, an CTLA4-Ig fusion protein, abatacept, belatacept, an anti-CTLA4 antibody, ipilimumab, tremelimumab, an anti-eotaxin 1 antibody, bertilimumab, an anti-a4-integrin antibody, natalizumab, an anti-IL-6R antibody, tocilmimab, an anti-LFA-1 antibody, odulimomab, an anti-CD25 antibody, basiliximab, daclizumab, inolimomab, an anti-CD5 antibody, zolimomab, an anti-CD2 antibody, siplizumab, nerelimomab, faralimomab, atlizumab, atorolimumab, cedelizumab, dorlimomab aritox, dorlixizumab, fontolizumab, gantenerumab, gomiliximab, lebrilizumab, maslimoraab, morolimumab, pexelizumab, reslizumab, rovelizumab, talizumab, tehmomab aritox, vapalixtmab, vepalimomab, aflibereept, alefacept, rilonacept an IL-1 receptor antagonist, anakinra, an anti-IL-5 antibody, mepolizumab, an IgE inhibitor, omalizumab, talizumab, an IL12 inhibitor, an IL23 inhibitor, ustckinumah, and the like.

Nutritional supplements that enhance immune responses, such as vitamin A, vitamin E, vitamin C, and the like, are well known in the art (see, for example, U.S. Pat. Nos. 4,981,844 and 5,230,902 and PCT Publ. No, WO 2004/004483) can be used in the methods described herein.

Similarly, agents and therapies other than immunotherapy or in combination thereof can be used with in combination with anti-RGMb and anti-PD-1 agents to stimulate an immune response to thereby treat a condition that would benefit therefrom. For example, chemotherapy, radiation, epigenetic modifiers (e.g., histone deacetylase (HDAC) modifiers, methylation modifiers, phosphorylation modifiers, and the like), targeted therapy, and the like are well known in the art.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine: DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research laboratories. Inc.); INO-1001 (Inotek Pharmaceuticals Inc.); PJ34 (Soriano et al., 2001; Pacher et al., 2002b); 3-ammobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity, PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H. E, et al. (2005) Nature 434:913-917; Farmer H, et al. (2005) Nature 434:917-921). The foregoing examples of chemotherapeutic agents are illustrative, and are not intended to be limiting. Additional examples of chemotherapeutic and other anti-cancer agents are described in US Pat. Publs. 2013/0239239 and 2009/0053224.

In still another embodiment, the term "targeted therapy" refers to administration of agents that selectively interact with a chosen biomolecule to thereby treat cancer. For example, bevacizumab (Avastin®) is a humanized monoclonal antibody that targets vascular endothelial growth factor (see, for example, U.S. Pat. Publ. 2013/0121999, WO 2013/083499, and Presta et al. (1997) Cancer Res. 57:4593-4599) to inhibit angiogenesis accompanying tumor growth. In some cases, targeted therapy can be a form of immunotherapy depending on whether the target regulates immunomodulatory function.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In still another embodiment, a step of lymphodepletion prior to, concurrently with, or after the administration of agents that inhibit, or block RGMb and PD-1 expression and/or activity. Methods for achieving lymphodepletion in various forms and at various levels are well known in the art (see, for example, U.S. Pat. No. 7,138,144). For example, the term "transient lymphodepletion" refers to destruction of lymphocytes and T cells, usually prior to immunotherapy. This can be accomplished in a number of ways, including "sublethal irradiation," which refers to administration of one or more doses of radiation that is generally non-lethal to all members of a population of subjects to which the administration is applied. Transient lymphodepletion is generally not myeloablative, as would be the ease in complete lymphodepletion, such that the subjects hematopoietic or immunological capacity remains sufficiently intact to regenerate the destroyed lymphocyte and T cell populations. By contrast, "lethal irradiation" occurs when the administration is generally lethal to some but not all members of the population of subjects and "supralethal irradiation" occurs when the administion is generally lethal to all members of the population of subjects.

Depending on the application and purpose, transient lymphodepletion or complete lymphodepletion may be effected, for example, fay any combination of irradiation, treatment with a myeloablative agent, and/or treatment with an immunosuppressive agent, according to standard protocols. For example, biological methods include, for example, administration of immunity-suppressing cells or by administration of biological molecules capable of inhibiting immunoreactivity, such as, for example, Fas-ligand and CTLA4-Ig. Examples of myeloablative agents include busulfan, dimethyl milcran, melphalan and thiotepa. Examples of immunosuppressive agents include prednisone, methyl prednisolone, azathioprine, cyclosporin A, cyclophosphamide, fludarabin, CTLA4-Ig, anti-T cell antibodies, etc.

In some embodiments, depletion of specific lymphocyte subsets is useful and can be effected through treatment with agents, such as antibodies, to deplete immune system-mediating cell populations, or treatment with agents that preferentially deplete immune system-mediating cell populations (see, for example, Hayakawa et al. (2009) *Stem Cells* 27:175-182). For example, anti-CD4 and anti-CD8 antibodies can be used to neutralize and/or deplete CD4+ T cells and CD8+ T cells, respectively. Similarly, anti-CTLA-4 antibodies can be used to deplete regulatory T cells, anti-CD3 antibodies can be used to deplete all T cells, anti-B220 and/or anti-CD19 antibodies can be used to deplete all B cells, anti-CD11b antibodies can be used to deplete macrophages, anti-Ly-6G (Gr-1) antibodies can be used to deplete monocytes and granulocytes, and anti-NK1.1 antibodies can be used to deplete Natural Killer (NK) cells.

Regarding irradiation, a sublethal dose of irradiation is generally within the range of 1 to 7.5 Gy whole body irradiation, a lethal dose is generally within the range of 7.5 to 9.5 Gy whole body irradiation, and a supralethal dose is within the range of 9.5 to 16.5 Gy whole body irradiation.

Depending on the purpose and application, the dose of irradiation may be administered as a single dose or as a fractionated dose. Similarly, administering one or more doses of irradiation can be accomplished essentially exclusively to the body part or to a portion thereof, so as to induce myeloreduction or myeloablation essentially exclusively in the body part or the portion thereof. As is widely recognized in the art, a subject can tolerate as sublethal conditioning ultra-high levels of selective irradiation to a body part such as a limb, which levels constituting lethal or supralethal conditioning when used for whole body irradiation (see, for example, Breitz (2002) *Cancer Biother Radiopharm.* 17:119; Limit (1997) *J. Nucl. Med.* 38; 1374; and Dritschilo and Sherman (1981) *Environ. Health Perspect.* 39:59). Such selective irradiation of the body part, or portion thereof, can be advantageously used to target particular blood compartments, such as specific lymph nodes, in treating hematopoietic cancers.

The radiation used in radiation therapy can be ionizing radiation. Radiation therapy can also be gamma rays. X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Bellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LU-FRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin. D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that, is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light. In combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that, destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent, called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through, steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine. Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with liber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less that) the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

e. Administration of Agents

The immune modulating agents of the invention are administered to subjects in a biologically compatible form suitable for pharmaceutical administration in vivo, to enhance immune cell mediated immune responses. By "biologically compatible form suitable for administration in vivo" is meant a form to be administered in which any toxic effects are outweighed by the therapeutic effects. The term "subject" is intended to include living organisms in which an immune response can be elicited, e.g., mammals. Examples of subjects include humans, dogs, eats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of an agent may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

Inhibiting or blocking both RGMb and PD-1 expression and/or activity can be accomplished by combination therapy with the modulatory agents described herein. Combination therapy describes a therapy in which both RGMb and PD-1 are inhibited or blocked simultaneously. Simultaneous inhibition or blockade may be achieved by administration of the modulatory agents described herein simultaneously (e.g., in a combination dosage form or by simultaneous administration of single agents) or by administration of single agents according to a schedule that results in effective amounts of each modulatory agent present in the patient at the same time.

The therapeutic agents described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat fee agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol* 7:27).

The agent may also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions of agents suitable for injectable use include sterile aqueous solutions (where water soluble) or dispersions and sterile powders for the extemporaneous preparation of sterile injectable solutions or dispersion. In all cases the composition will preferably be sterile and must be fluid to the extent that easy syringeability exists. It will preferably be stable under the conditions of manufacture and storage and preserved against the contaminating action of microorganisms such, as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about, by including in the composition an agent which delays absorption, for example, aluminum monostearate and gelatin.

Sterile injectable solutions can be prepared by incorporating an agent of the invention (e.g., an antibody, peptide, fusion protein or small molecule) in the required amount, in art appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the agent plus any additional desired ingredient from a previously sterile-filtered solution thereof.

When the agent is suitably protected, as described above, the protein can be orally administered, for example, with an inert diluent or an assimilable edible carrier. As used herein, the term "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. "Dosage unit form", as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit, forms of the invention are dictated by, and directly dependent on, (a) the unique characteristics of the active compound and die particular therapeutic effect to be achieved, and (b) the limitations inherent in the art of compounding such an active compound for the treatment of sensitivity in individuals.

In one embodiment, an agent of the invention is an antibody. As defined, herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat, a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

III. Kits

The present invention also encompasses kits for treating disorders that would benefit from unregulated immunot responses, such as infections and cancers like colorectal cancer, using agents that inhibit or block RGMb and PD-1 expression and/or activity. For example, the kit can comprise an anti-RGMb antibody and an anti-PD-1 antibody packaged in a suitable container and can further comprise instructions for using such, antibodies to treat cancers in a patient in need thereof. The kit may also contain other components, such as administration tools like packaged in a separate container.

This invention is further illustrated by the following examples which should not be construed as limiting. The contents of all references, patents and published patent applications cited throughout this application, as well as the Figures, are incorporated herein by reference.

EXAMPLES

Example 1: Materials and Methods for Examples 2-5 a. Mice

Wild type (WT) BALB/cJ mice were purchased from the Jackson Laboratory. Age-matched female mice were used at 6 weeks. Animal protocols were approved by The Animal Care and Use Committees at the Dana-Farber Cancer Institute, Harvard Medical School.

b. Cancer Cell Line and Culture, Media

Mouse colon cancer cell line CT26, mouse renal cancer cell line RENCA, and mouse breast cancer cell line 4T1 were purchased from the American Type Culture Collection (ATCC). Cells were cultured in RPMI-1640 (Mediatech) supplemented with 10% heat-inactivated FBS (Invitrogen), 1% streptomycin/penicillin, 15 μg/ml gentamicin (Invitrogen), and 1% glutamax (Invitrogen) at 37° C. in a 5% $CO_2$ incubator.

c. Mouse Cancer Model and Antibody Treatment

Under anesthesia with isoflurane, BALB/cJ mice were subcutaneously (s.c.) injected with mouse colon cancer cell line CT26 at 5×10^5 cells/mouse in the left flank on day 0. Mice were then treated with mouse monoclonal antibodies (mAbs) via intraperitoneal (i.p.) injection on days 2, 5, 8, 11, 14, 17, 20 and 23. The antibody treatments were RGMb mAb (307.9D1, rat IgG2a), PD-1 mAb (29F. 1A12, rat IgG2a), and/or isotype control rat IgG2a (clone 2A3, BioX-Cell), at 200 μg of the indicated mAb(s) per mouse per injection as indicated. In order to test the development of anti-tumor immunologic memory, tumor-free mice were challenged (s.c. injected) with CT26, RENCA, or 4T1 tumor cell line cells at 5×10^5 cells/mouse. Specifically, tumor free mice were challenged on day 60 with the CT26 cell line by injection in the left flank, then further challenged on day 130 with the CT26 cell line or the RENCA renal cancer cell line by injection in the right flank. Mice remaining tumor-free after this first challenge were challenged on day 175 with the 4T1 cancer cell line by injection in the right flank. Treatment naive control mice received the same injection. Mice were monitored for survival and two perpendicular diameters of a tumor were measured every 3 days. Tumor volume was calculated using the formula, $V=L \times W^2/2$ (V: volume, L: length, W: width). In some experiments, mice were treated with the indicated mAbs on days 2, 5, 8, 11, and 14. On day 17, cells were isolated from tumors and analyzed by flow cytometry and qRT-PCR.

d. Complete Necropsy

Long-tumor survivor mice following mAb treatment and age-matched control mice, with front and back skin cut open, were fixed with neutral buffered 10% Formalin solution (Sigma). Complete necropsy was performed and analyzed at the Rodent Histopathology Core, Dana-Farber/Harvard Cancer Center in Boston, Mass.

e. Cell Isolation from Tumors

Tumors were removed from mice and cut into tiny pieces, digested in RPMI 1640 with 5% FBS, 1 mg/ml collagenase IV (Sigma), and 200 u/ml DNase I (Roche) at 37° C. for 1 hr., and then treated with red blood cell lysing buffer (Sigma).

f. Flow Cytometry

Cells isolated from tumors were stained with target antibodies and isotype controls using standard flow cytometry procedures. Cells were first stained with LIVE-DEAD® Fixable Near-IR (Invitrogen) at 1:1000. After pre-incubation with mouse Fc receptor mAb (2.4G2), cells were stained for surface markers with multiple fluorescence-conjugated anti-mouse mAbs at 2.5 μg/ml: CD45 (30-F11)-BV605, F4/80 (BM8)-Alex 488, CD11c (N418)-APC, CD11b (M1/70)-PECy7, CD3 (17A2)-BV786, CD4 (RM4-5)-BV650, CD8 (53-6.7)-BV711, CD19 (6D5)-BV510, PD-1 (RPMI-30)-PerCP eFluor710, PD-L1 (10F.9G2)-BV421, plus RGMb (307.9D1)-PE or PD-L2 (TY-25)-PE. All commercial antibodies were purchased from BioLegend, except for PD-1-PerCP eFluor710, which was purchased from eBioscience. Stained cells were analyzed on a Fortessa SORP flow cytometer (BD Biosciences) and data were analyzed with FlowJo 9.2 software (TreeStar).

In order to test if PD-1 mAb clone 29F.1A12 blocks binding of PE-conjugated PD-1 mAb clone RPMI-30 to PD-1, PD-1-transfected 300 cells were pre-incubated with the indicated concentrations of PD-1 mAb clone 29F.1A12, PD-1 mAb clone 332.5E12, or isotype control, then stained with PE-conjugated PD-1 mAb clone RPMI-30 and analyzed by flow cytometry. Staining with isotype control (IgG-PE) was also included.

g. qRT-PCR

Total RNA samples were prepared from cells of whole tumors using the RNeasy mini kit (QIAGEN). Reverse transcription was performed using the QuantiTect® reverse transcription kit (QIAGEN). qPCR using TaqMan® gene expression assays for IL-4, IL-13, IL-12, and RPL19 (Applied Biosystems) were carried out in a 7300 Real-Time PCR system (Applied Biosystems). Fold-changes as compared with RPL19 were calculated using the ΔCt method.

h. Statistical Analysis

Kaplan-Meier survival analysis was used to make survival curves and the Gehan-Breslow-Wilcoxon test was used to determine significance between survival curves. Chi-square test was used to compare the difference in RENCA tumor eradication or growth delay between mAb treated mice and treatment naïve control mice. The non-parametric Kruskai-Wallis test for multiple comparisons was used to compare PD-L2 expression, as well as IL-4, IL-13 and IL-12 mRNA expression with different treatments. Linear regression analysis was used to analyze correlation between tumor size and IL-4 mRNA expression. All statistical analyses were performed using GraphPad Prism version 6.00 for MacOS X, GraphPad Software, La Jolla Calif. USA, graphpad.com. $p<0.03$ was considered as significant.

Example 2: Anti-Tumor Efficacy of Single and Combination Blockade of RGMb and PD-1

Colorectal cancer (CRC) is one of the most common cancer types and one of the leading causes of cancer related death (Edwards et al (2014) *Cancer* 120:1290-1314). CRC appears to be a poor responding cancer type to antibody blockade of programmed death-1 (PD-1) or PD-1 ligand 1 (PD-L1) in clinical trials (Brahmer et al. (2012) *N. Engl. J. Med.* 366:2455-2465; Topalian et al. (2012) *N. Engl J. Med.* 366:2443-2454). Recently, Llosa and colleagues (Llosa et al (2014) *Cancer Discov.* 5:43-51) found that the microsatellite instable subset (MSI) of colorectal cancer was highly infiltrated with activated CD8+ cytotoxic T lymphocytes and activated Th1 cells. In addition, PD-1, PD-L1, cytotoxic T lymphocyte-associated antigen 4 (CTLA-4), lymphocyte activation gene 3 (LAG-3), and indolamine 2,3-dioxygenase (IDO) were highly unregulated in MSI tumor's and these five molecules are currently being targeted clinically. Thus, the MSI subset of colorectal cancer is poised to be a particularly good candidate for checkpoint blockade immunotherapy (Xiao and Freeman (2015) *Cancer Discov.* 5:16-18). MSI is caused by epigenetic silencing or mutation of DNA mismatch repair genes, but MSI CRC comprises only about 15% of sporadic CRC and most familial CRC while microsatellite stable (MSS) CRC composes the remaining 85% (Smyrk et al. (2001) *Cancer* 91:2417-2422). Most MSI CRC typically presents with lower stage disease than MSS CRC, thus the MSI subtype represents only 5-6% of the stage IV CRC population typically enrolled in clinical trials (Lochhead et al (2013) *J. Natl. Cancer Inst.* 105:1151-1156). Therefore, most CRC patients in clinical trials are poor responders to antibody blockade of the PD-1 pathway. This leaves a great need for effective immunotherapies in the remaining 95% of stage IV CRC patients (Xiao and Freeman (2015) *Cancer Discov.* 5:16-18). The CT26 colon carcinoma cell line is one of the most commonly used cell lines in mouse cancer models. Castle et al showed that none of the mismatch repair genes are mutated in CT26 (Castle et al. (2014) *BMC Genomics* 15:190). Thus, the CT26 cell line is not of MSI type and is representative of the 95% of stage IV CRC.

The syngeneic mouse CT26 colon cancer model was used to investigate the immunotherapeutic effect of antibody blockade of RGMb. BALB/c mice were injected with CT26 cancer cells subcutaneously (s.c.) in the left flank on day 0. Mice were treated with the indicated monoclonal antibodies (mAb) on days 2, 5, 8, 11, 14, 17, 20 and 23 (FIG. 1A). Tumor volume and survival data show that blockade of RGMb did not show anti-tumor efficacy (FIGS. 1B-1F). PD-1 antibody blockade alone had moderate efficacy (26% survival) (FIG. 1G). However, the combination of RGMb antibody blockade with PD-1 antibody blockade increased mouse survival as compared to PD-1 antibody blockade alone (50% vs 26%) (FIG. 1G). Survivors in both combination and single blockade groups were tumor-free (FIGS. 1C and 1E).

Example 3: Anti-Tumor Immune Memory in Long-Term Survivors Treated with Single and Combination Blockade of RGMb and PD-1

Figure 2:
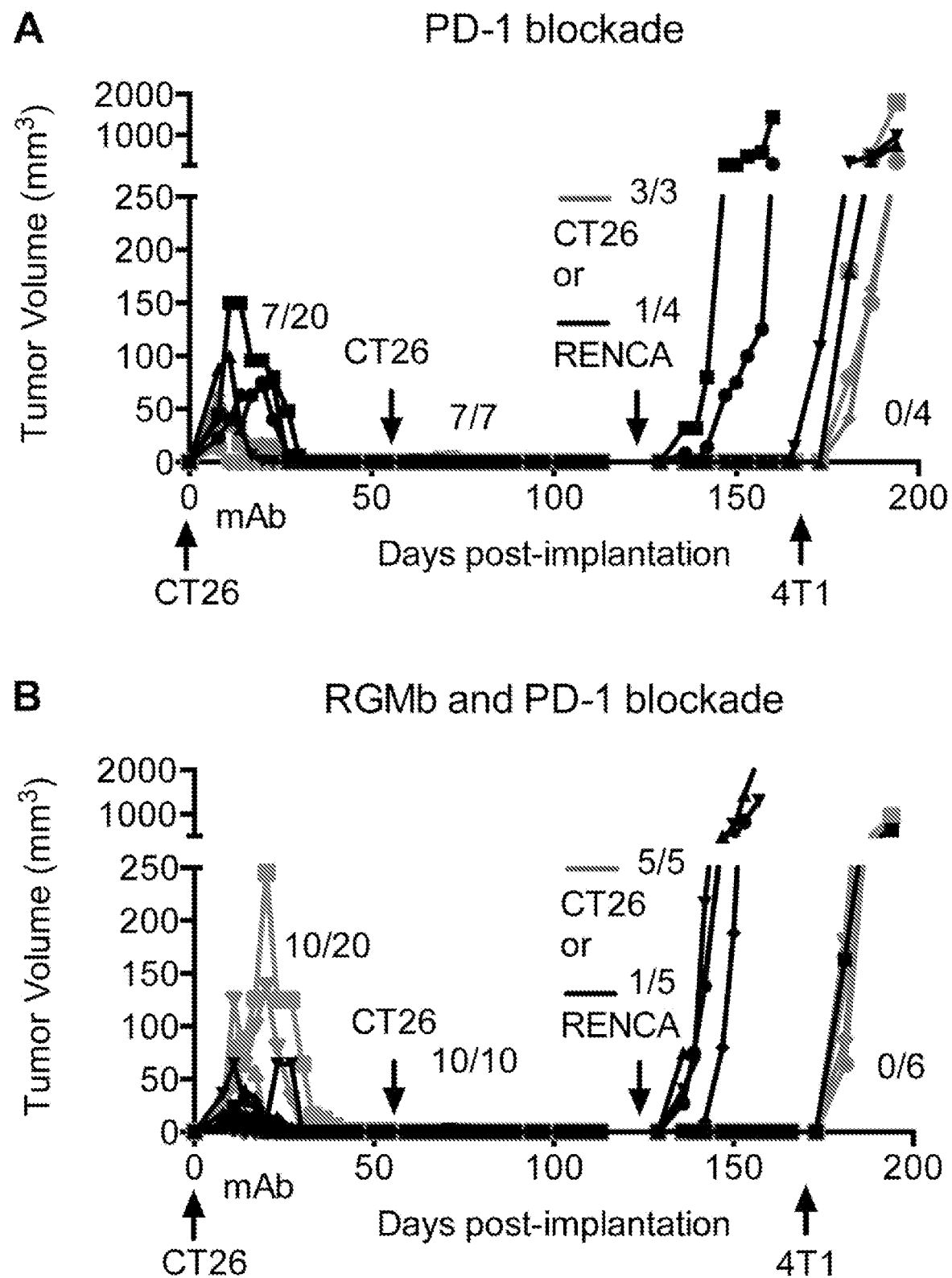
FIG. 2 includes 2 panels, identified as panels A and B, which show anti-tumor immune memory in long-term survivors. Mice were implanted with CT26 tumor cells and treated as in FIG. 1. Long-term survivors were challenged on day 60 with CT26 cells. All mice survived and were re-challenged on day 130 with, either CT26 cells or RENCA. Mice surviving this re-challenge were challenged on day 175 with 4T1 cells, as indicated by arrows. The 7 of 20 mice who survived with PD-1 mAb treatment were challenged with tumor as indicated (panel A). The 10 of 20 mice who survived with PD-1 mAb plus RGMb mAb treatment were challenged with tumor as indicated (panel B).

In order to test the development of anti-tumor immunologic, memory, tumor-free mice were challenged with tumor cells by s.c, injection in the flank (FIGS. 2A-2B). The 7 of 20 mice who survived with PD-1 mAb treatment (FIG. 2A) and the 10 of 20 mice who survived with PD-1 mAb plus RGMb mAb treatment (FIG. 2B) were challenged on day 60 with CT26 cell line. All mice eradicated the new tumor to remain tumor-free survivors.

In order to determine whether this immune memory was specific to CT26 tumors, these tumor-free mice were then challenged on day 130 with a CT26 cell line or a mouse renal cancer cell line, RENCA. Again, all mice challenged with CT26 eradicated tumors to be tumor-free survivors. Surprisingly, one of the four mice in the group with PD-1 mAb treatment (FIG. 2A) and one of the five mice in the group with PD-1 mAb plus RGMb mAb treatment (FIG. 2B) also eradicated RENCA tumors to be tumor free survivors. One of the four mice in the group with PD-1 mAb treatment had a very delayed RENCA tumor growth starting on day 36 after challenge (FIG. 2A). Treatment naïve control mice that received the same RENCA cell injection showed tumor growth starting before day 10, and none of 17 mice exhibited tumor eradication or growth delay. The difference in complete RENCA tumor eradication or tumor growth delay between these mAb-treated survivor mice and treatment naïve control mice (3/9 vs 0/17, $p=0.0295$, Chi-square test) indicates that some of these mAb treated survivor mice gained immunity against RENCA tumor from the anti-CT26 immunological response.

In order to determine whether this phenomenon also applied to other tumor types, the remaining 10 tumor free survivors were challenged on day 175 with mouse breast cancer cell line 4T1. None of these mice showed anti-4T1 tumor responses, indicating that anti-CT26 memory did not extend to the 4T1 tumor.

Taken together, the data indicate that the anti-tumor memory responses developed from PD-1/RGMb antibody treatment of CT26 tumor rendered these mice long-term survivors and resistant to CT26 re-challenge. In addition, the memory responses have some effectiveness against some (RENCA), but not all (4T1), other tumor re-challenges. Since RENCA and CT26 are unlikely to share identical mutations that generate a neoantigen, this suggests some immunologic memory against a conserved self-antigen like gp100.

Long-term tumor free survivors (>6 months) showed no gross symptoms of adverse events. The long-term tumor survivors were further analyzed with complete necropsies, which included sections of all organs. Six mice with PD-1 mAb or PD-1 mAb plus RGMb mAb treatment that survived for more than 6 months, as well as two age-matched mice, were analyzed. No inflammation or other lesions suggesting toxicity were observed. Some common lesions in older mice were observed, such as osteoarthritis in the joint and dilated horn of the uterus.

Figure 3:
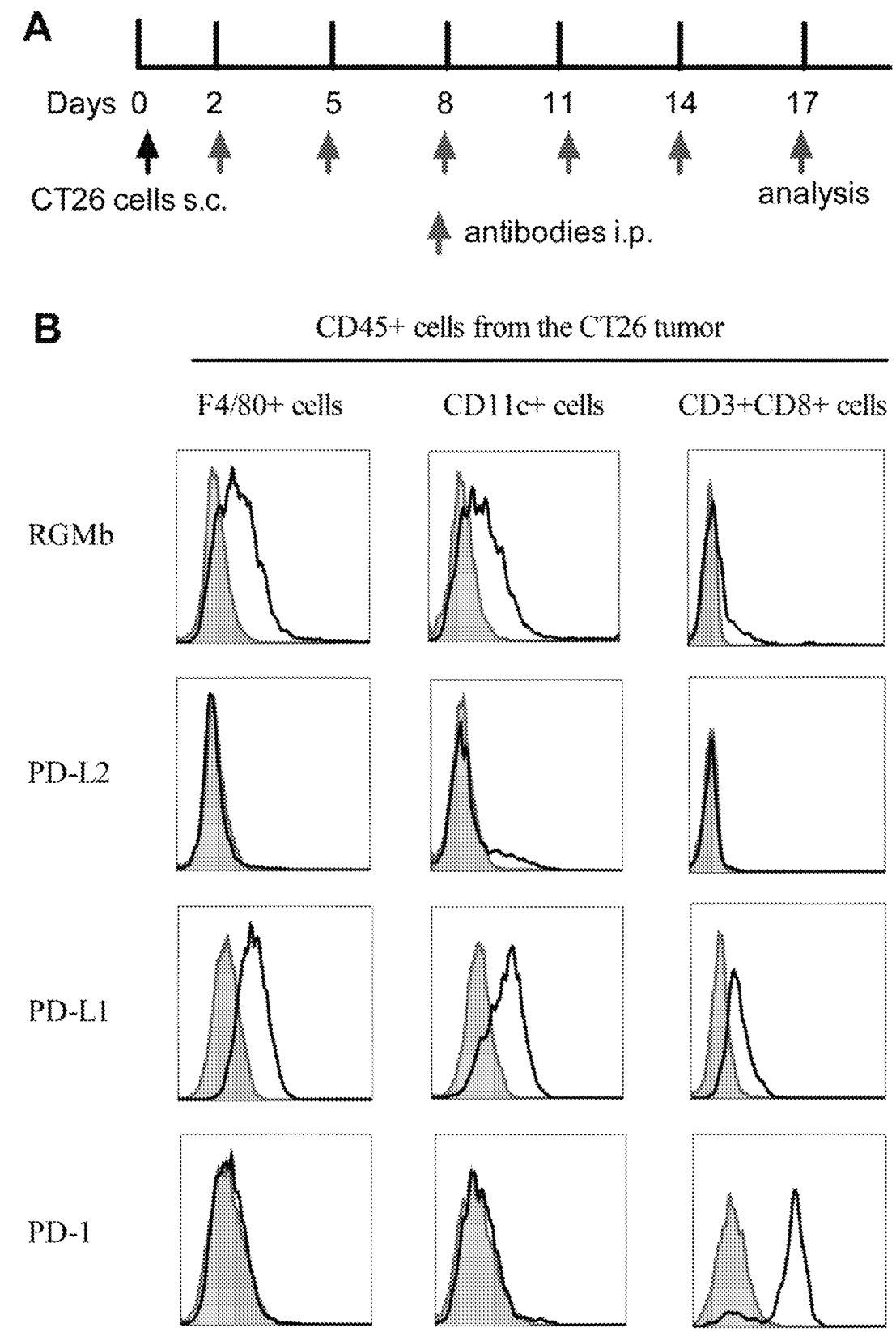
FIG. 3 includes 2 panels, identified as panels A and B, which show expression of RGMb PD-L2, PD-1, and PD-L1 on CT26 tumor infiltrating immune cells. Panel A shows the experimental protocol used in FIGS. 3 and 5. BALB/c mice were s.c. injected with CT26 cells in the left flank on day 0. Mice were treated with the indicated mAbs on days 2, 5, 8, 11, and 14. On day 17, cells were isolated from CT26 tumors and analyzed by flow cytometry. Panel B shows the results of FACS analyses of isotype control treated mice. Expression of RGMb, PD-L2, PD-1, and PD-L1 on tumor infiltrating macrophages (CD45$^+$F4/80$^+$), dendritic cells (CD45$^+$CD11c$^+$), and CD8$^+$ T cells (CD45$^+$CD3$^+$CD8$^+$) were determined. One representative mouse is shown (n=5).
Figure 4:
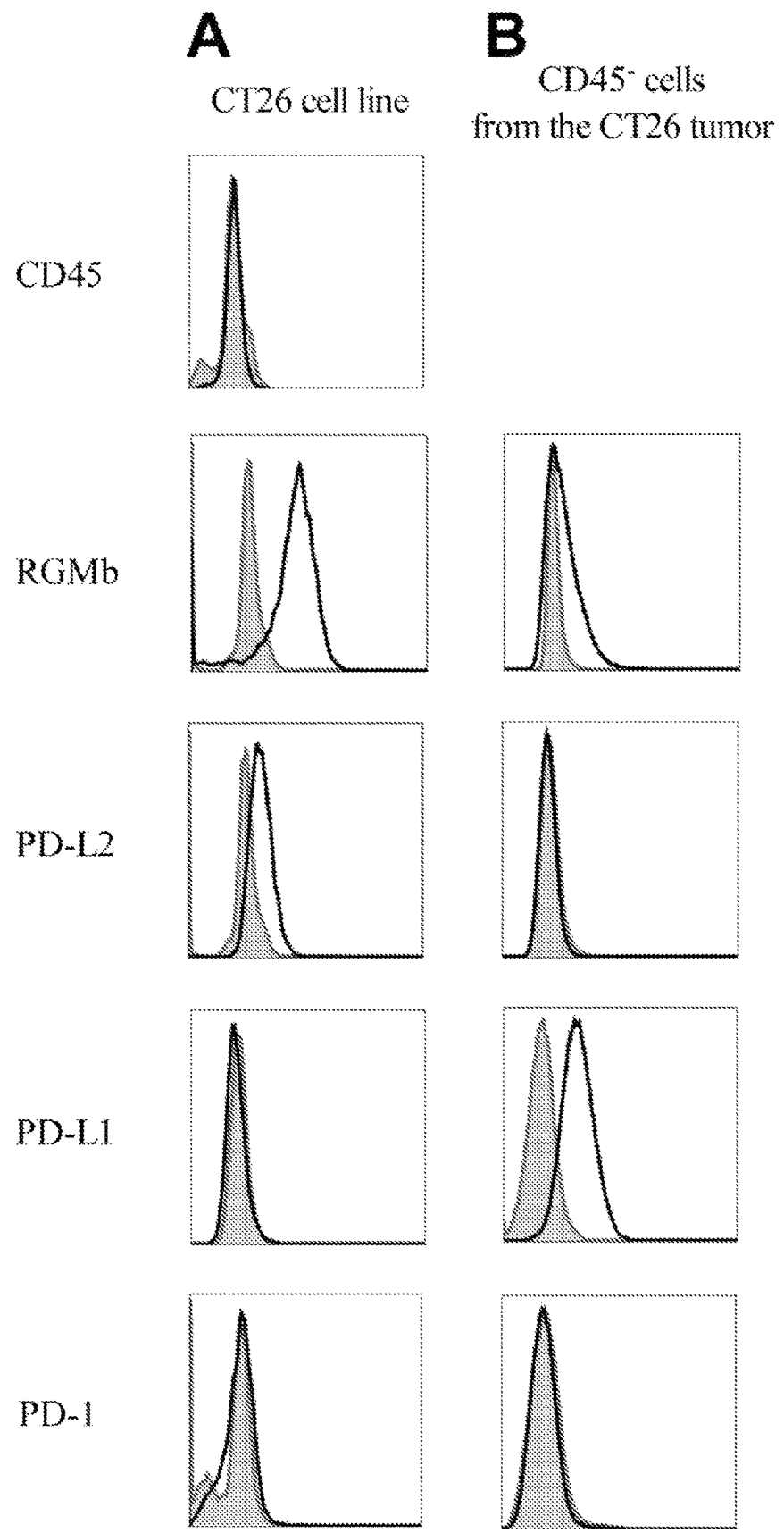
FIG. 4 includes 2 panels, identified as panels A and B, which show cell surface expression of RGMb, PD-L2, PD-1, and PD-L1 on CT26 cells in vitro and in vivo. Panel A shows the results of the CT26 cell line in vitro analyzed by FACS for expression of the indicated proteins. Panel B shows the results of the CT26 cell line in vivo (CD45− cells from isotype control treated tumor on day 17) analyzed by FACS for expression of the indicated proteins.

Example 4: Expression of RGMb, PD-L2, PD-1, and PD-L1 on Tumor Infiltrating Immune Cells The expression of RGMb, PD-L2, PD-1, and PD-L1 on cells from the whole CT26 tumor, which includes tumor cells and infiltrating immune cells, was analyzed. Mice were s.c. injected with CT26 cells on day 0, then treated with the indicated mAbs on days 2, 5, 8, 11, and 14. On day 17, cells were isolated from tumors and analyzed by multi-color flow cytometry (FIG. 3A). CD45+ tumor infiltrating immune cells and CD45− tumor cells from control mAb treated mice were analyzed and then surface expression among mice with different treatments (i.e., control PD-1, and PD-1 plus RGMb mAbs) was compared. For CD45+ tumor infiltrating immune cells from control mAb treated mice, marker expression on macrophages (CD45+F4/80+), dendritic cells (CD45+CD11c+) and CD8+ T cells (CD45+CD3+CD8+), was examined (FIG. 3B). Highly up-regulated levels of cell surface RGMb expression on tumor infiltrating macrophages and dendritic cells were observed. In contrast, under physiological resting conditions, cell surface expression of RGMb on immune cells was undetectable (Xiao et al. (2014) *J. Exp. Med* 211:943-959), PD-L2 expression was undetectable on macrophages and CD8+ T cells, and barely detectable on dendritic cells. Consistent with previous work, PD-L1 was mainly expressed on macrophages and dendritic cells and was low on CD8+ T cells, while PD-1 was highly expressed on CD8+ T cells and not on macrophages and dendritic cells. CD45− cells were the major cell population in the CT26 tumor and should be CT26 tumor cells. It was determined that the CT26 cell line was CD45− and also expressed high levels of RGMb, low levels of PD-L2, and no PD-L1 or PD-1 on the cell surface (FIG. 4A). However, CD45− tumor cells in control mAb treated mice showed lower levels of RGMb and no PD-L2 expression on the cell surface. As expected, PD-L1 expression was highly up-regulated and there was no PD-1 expression on CD45− tumor cells (FIG. 4B). Thus, the expression data demonstrated that hi the tumor microenviroment without immunotherapy, cell surface RGMb was up-regulated on CD45+ immune cells but down-regulated on CD45− tumor cells. PD-L2 was down-regulated on CD45− tumor cells, PD-L1 was expressed on CD45+ immune cells and highly up-regulated on CD45− tumor cells, while PD-1 was highly expressed on CD8+ T cells.

Example 5: Expression of PD-2, IL-4, and PD-1 in Mice with Tumors Treated with Single and Combination Blockade of RGMb and PD-1

Figure 5:
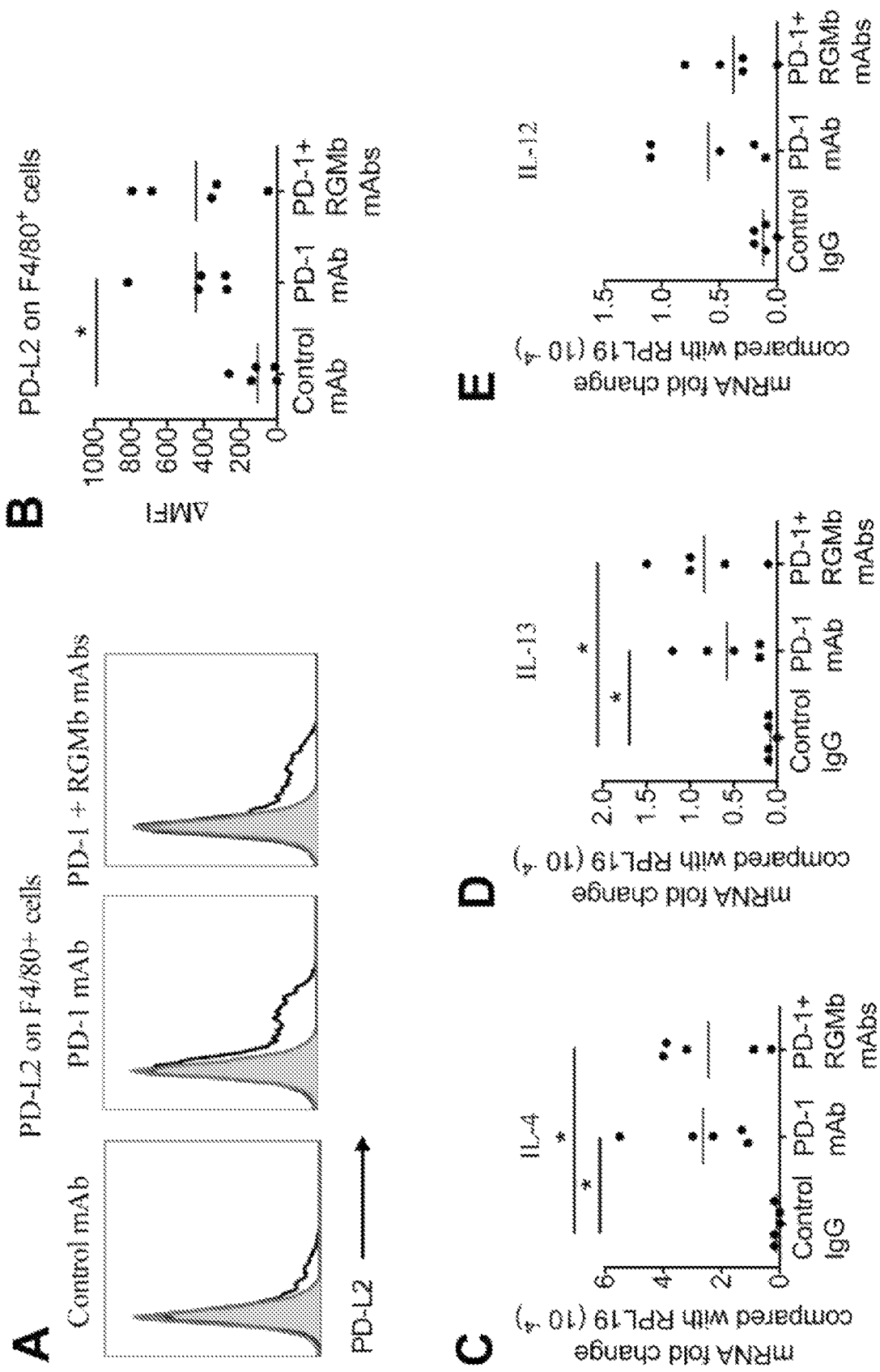
FIG. 5 includes 8 panels, identified as panels A, B, C, D, E, F, G, and E, show PD-L2 and IL-4 expression in CT26 mice treated with PD-1 or PD-1 plus RGMb mAbs. Cells from mice treated as described in Panel. A of FIG. 3. Panel A shows representative histograms of expression of PD-L2 on tumor infiltrating macrophages (CD45$^+$F4/80$^+$) following the indicated treatments. Panel B shows a graphical representation of data in panel A. MFI: mean fluorescence intensity; ΔMFI=MFI of target staining minus MFI of isotype control staining. Panels C-E show IL-4, IL-13, and IL-12 mRNA expression in total cells isolated from CT26 tumor with the indicated antibody treatments. For Panels B-E, the mean of each group is indicated; n=5; p<0.05; and nonparametric Kruskai-Wallis test for multiple comparisons. Panels F-H show a correlation between turner size and IL-4 mRNA expression in cells isolated from CT26 tumor on day 17 following the indicated antibody treatments using linear regression analysis (n=5).
Figure 5:
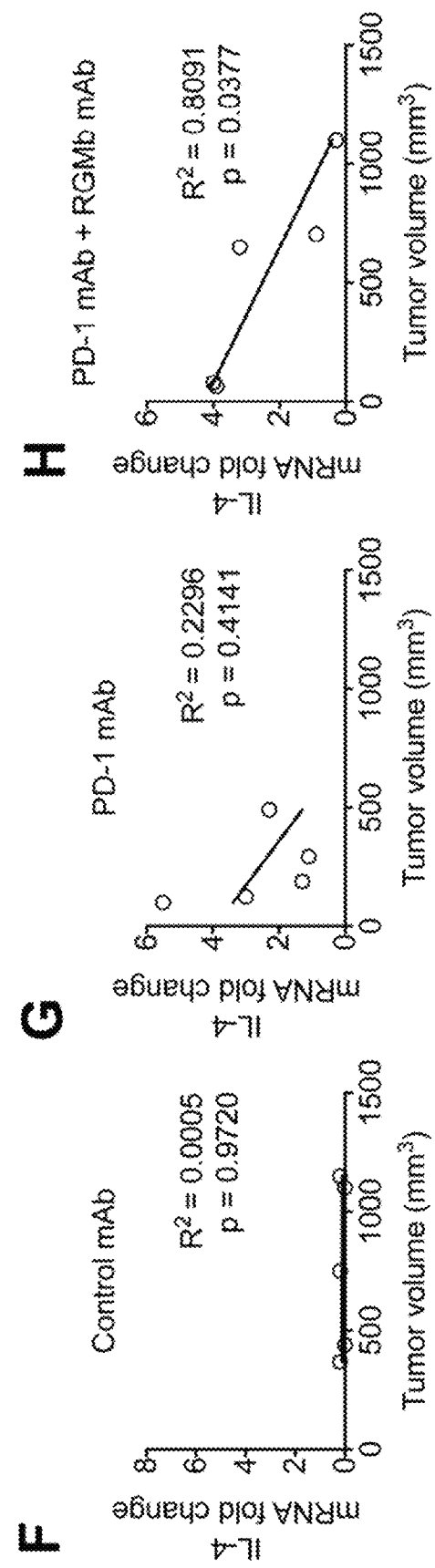

Among treatment groups with control, PD-1, and PD-1 plus RGMb mAbs, PD-L2 expression was up-regulated on macrophages on day 17 in mice with PD-1 mAb treatment (FIGS. 5A-5B), but not on dendritic cells or CD8+ T cells. The up-regulation of PD-L2 expression after PD-1 mAb treatment may explain the better efficacy of PD-1 mAb when combined with RGMb mAb which can block both RGMb and PD-L2 interaction. In order to explore the mechanism for PD-L2 up-regulation, mRNA expression of Th2 cytokines, which are well-known to upregulate PD-L2 expression, was analyzed. As expected, mRNA expression of Th2 cytokines IL-4 and IL-13, but not Th1 cytokine IL-12, was increased in cells isolated from CT26 tumors on day 17 (FIGS. 5C-5E). Furthermore, higher IL-4 mRNA expression correlated with smaller tumor volume in mice with PD-1 and RGMb mAb combination treatment, but not in mice with control IgG or PD-1 mAb single treatment (FIGS. 5F-5H), These data indicate that PD-1 mAb treatment induces Th2-mediated inflammation resulting in PD-L2 up-regulation in some mice that is sensitive to blockade of RGMb-PD-L2, leading to reduced tumor volume.

Figure 6:
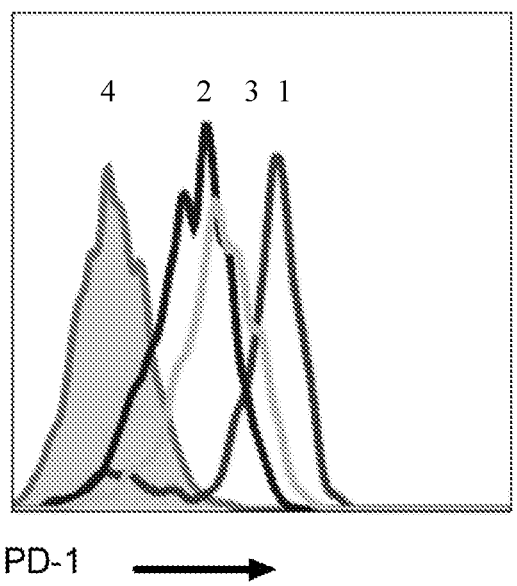
FIG. 6 includes 2 panels, identified as panels A and B, show that the expression of PD-1 on tumor infiltrating CD8$^+$ T cells is decreased after PD-1 mAb treatment. Panel A shows the expression of PD-1 on tumor infiltrating CD45$^+$ CD3$^+$ CD8$^+$ cells from mice following the indicated treatment was analyzed by flow cytometry with PD-1 mAb clone RPMI-30 on day 17 as in FIG. 3. The PD-1 treatment mAb was clone 29F.1A12. Panel B shows the results of PD-1 mAb clone 29F.1A12 blockade of PE-conjugated PD-1 mAb clone RPMI-30 binding to PD-1. PD-1-transfected 300 cells were pre-incubated with the indicated concentrations of PD-1 mAb clone 29F.1A12, PD-1 mAb clone 332.5E12, or isotype control, then stained with PE conjugated PD-1 mAb clone RPMI-30 and analyzed by flow cytometry. Staining with isotype control (IgG-PE) is also shown.
Figure 6:
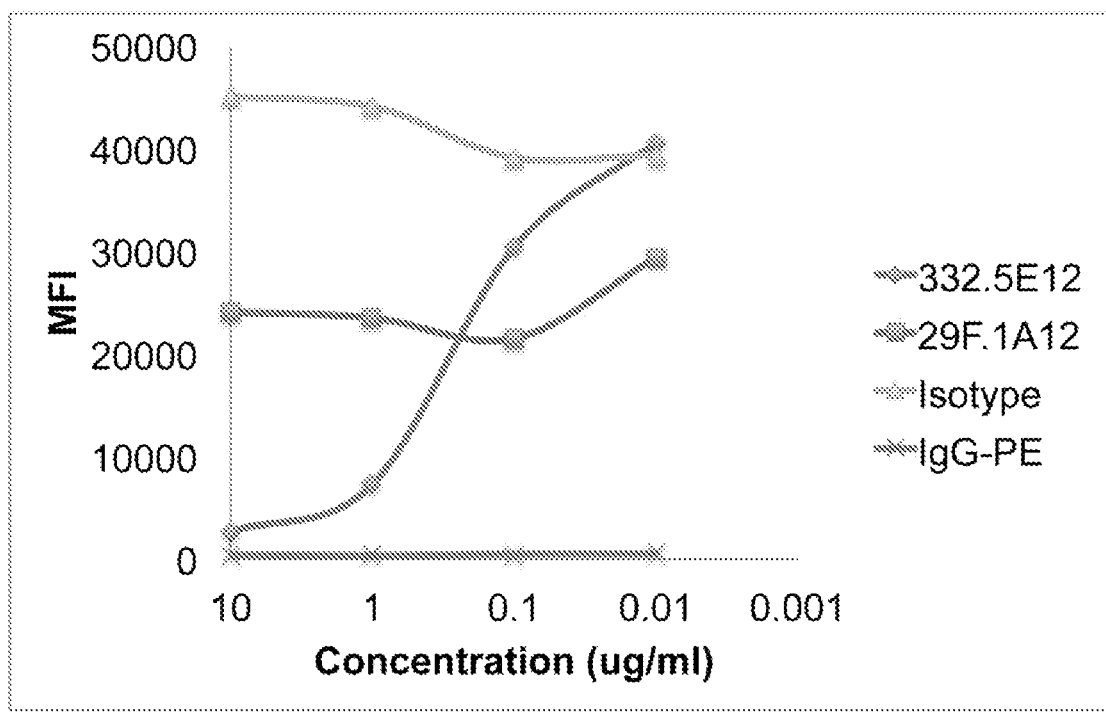

PD-L1 expression did not show significant changes on tumor infiltrating macrophages, dendritic cells, or CD8+ T cells on day 17 with different treatments. However, reduced PD-1 expression on tumor infiltrating CD8+ T cells on day 17 with PD-1 mAb treatment was observed in this study (FIG. 6A) and other studies that were performed. The PD-1 mAb used for treatment was clone 29F.1A12, while the PD-1 mAb for flow cytometry was clone RPMI-30. It has been shown that 29F.1.A12 and RPMI-30 bind to different epitopes and only minimally cross-block (FIG. 6B). These results indicate that PD-1 blockade by allowing a greater level of T cell activation may also have the effect of reducing PD-1 expression on tumor infiltrating CD8+ T cells.

Based on the results described above, the combined antibody blockade of both RGMb and PD-1 increased survival in the syngeneic mouse CT26 colon cancer model, as compared with PD-1 blockade alone (some survival effect) and single RGMb blockade (no survival effect). Survivors were tumor-free and remained tumor-free after tumor challenges, indicating the development of immunologic memory. The immune memory response developed after antibody treatment in CT26 tumor was effective against CT26 tumor and did not protect, mice from 4T1 breast tumor challenge. However, some mice (3/9) showed effective immunity against RENCA tumor after challenge with RENCA cells. CT26 and RENCA cells may share some common self antigens. Therefore, immunotherapy for one type of cancer may have the capacity to prevent, another cancer type sharing the same antigens.

Highly up-regulated cell surface RGMb expression was observed on tumor infiltrating macrophages and dendritic cells. In contrast, under physiological resting conditions, cell surface expression of RGMb on immune cells was undetectable (Xiao et al. (2014) *J. Exp. Med* 211:943-959). A high level of cell surface RGMb expression on CT26 cell line (CD45+) was also observed, but RGMb expression was down-regulated on CD45+ tumor cells isolated from CT26 tumor. Previous studies have shown RGMb expression on various cancer cell lines or cancer tissues (Li et al. (2012) *Int. J. Oncol.* 40:544-550; Li et al. (2011) *Anticancer Res.* 31:1703-1711; Li et al. (2012) *J. Cell Biochem.* 113:2523-2531; Li et al. (2015) *Diagn. Pathol* 10:63; Shi et al. (2015) *Oncotarget* 6:20540-20554; and Xiao et al. (2014) *J. Exp. Med.* 211:943-959). For the non-immune function of RGMb in tumor cell growth, two studies showed that RGMb inhibited the growth of beast cancer and prostate cancer through the BMP pathway (Li et al. (2012) *Int. J. Oncol* 40:544-550; Li et al. (2012) *J. Cell Biochem.* 113:2523-2531) and one study found that RGMb promoted CRC growth through the BMP pathway. With the interaction between the tumor and the immune system, the immune system may down-regulate RGMb expression on CT26 tumor cells and the tumor may provide signals to up-regulate RGMb expression on immune cells.

In addition, it was found that PD-L2 expression was up-regulated on tumor infiltrating macrophages after PD-1 mAb treatment and in association with higher level of IL-4 mRNA, which is correlated with smaller tumor volume. These data indicate that PD-1 mAb treatment induces Th2-mediated inflammation resulting in PD-L2 up-regulation on macrophages. Since RGMb was also up-regulated on tumor infiltrating macrophages and dendritic cells, the RGMb and PD-L2 interaction is believed to contribute to immunosuppression in the tumor microenviroment, according to the finding that the RGMb-PD-L2 interaction markedly promotes the development of respiratory tolerance (Xiao et al (2014) *J. Exp. Med.* 211:943-959). Foxp3 expression increase on those cells with PD-1 mAb treatment was not observed and additional studies can clarify the involvement of other mechanisms. Up-regulation of PD-L2 expression after PD-1 mAb treatment provides an opportunity for RGMb and PD-L2 interaction which may explain the better efficacy of PD-1 and RGMb combination antibody blockade.

These results indicate that immune checkpoint combination immunotherapy using anti-RGMb and anti-PD-1 agents for treating CRC and other disorders, such as cancers and infections, especially where PD-1 blockade has some efficacy, are more effective. For example, survival in CRC patients, especially those poor responders to immunotherapy targeting the PD-1 pathway, can be enhanced using a combination.

What is claimed is:

1. A method of treating a subject having a cancer or an infection comprising administering to the subject a therapeutically effective amount of at least one agent that selectively inhibits or blocks the expression or activity of both RGMb and PD-1, wherein the at least one agent is a bispecific or multispecific antibody, or antigen binding fragment thereof, selective for both RGMb and PD-1, or wherein the at least one agent is a combination of agents comprising a first antibody, or an antigen binding fragment thereof, that specifically binds to RGMb, and a second antibody, or an antigen binding fragment thereof, that specifically binds to PD-1, wherein the antibody that specifically binds to RGMb is selected from the group consisting of 1) anti-RGMb antibodies that block the interaction between a BMP and RGMb without blocking the interaction between PD-L2 and RGMb, 2) anti-RGMb antibodies that block the interaction between NEO1 and RGMb without blocking the interaction between PD-L2 and RGMb, 3) anti-RGMb antibodies that block both the BMP/RGMb interaction and NEO1/RGMb interaction and without blocking the interaction between PD-L2 and RGMb, 4) anti-RGMb antibodies that block the interaction between a BMP and RGMb and block the interaction between PD-L2 and RGMb, 5) anti-RGMb antibodies that block the interaction between NEO1 and RGMb and block the interaction between PD-L2 and RGMb, and 6) anti-RGMb antibodies that block both the BMP/RGMb interaction and NEO1/RGMb interaction and further block the interaction between PD-L2 and RGMb.

2. The method of claim 1, wherein the antibody that specifically binds PD-1 is selected from the group consisting of anti-PD-1 antibodies that block the interaction between PD-1 and PD-L1 without blocking the interaction between PD-1 and PD-L2; anti-PD-1 antibodies that block the interaction between PD-1 and PD-L2 without blocking the interaction between PD-1 and PD-L1; and anti-PD-1 antibodies that block both the interaction between PD-1 and PD-L1 and the interaction between PD-1 and PD-L2.

3. The method of claim 1 or 2, wherein said antibody, or antigen binding fragment thereof, is murine, chimeric, humanized, composite, or human.

4. The method of claim 1 or 2, wherein said antibody, or antigen binding fragment thereof, is detectably labeled, comprises an effector domain, comprises an Fc domain, and/or is selected from the group consisting of Fv, F(ab')2, Fab', dsFv, scFv, sc(Fv)2, and diabodies fragments.

5. The method of claim 1 or 2, wherein said antibody, or antigen binding fragment thereof, is conjugated to a cytotoxic agent.

6. The method of claim 5, wherein said cytotoxic agent is selected from the group consisting of a chemotherapeutic agent, a biologic agent, a toxin, and a radioactive isotope.

7. The method of claim 1 or 2, wherein said at least one agent is administered in a pharmaceutically acceptable formulation.

8. The method of claim 1 or 2, wherein anergy, exhaustion, and/or clonal deletion of immune cells in the subject is reduced.

9. The method of claim 1 or 2, further comprising administering one or more additional agents or therapies that upregulates an immune response or treats the cancer or infection.

10. The method of claim 9, wherein the one or more additional agents or therapies is selected from the group consisting of immunotherapy, immune checkpoint inhibition, a vaccine, chemotherapy, radiation, epigenetic modifiers, and targeted therapy.

11. The method of claim 1 or 2, wherein the subject is a mammal.

12. The method of claim 11, wherein the mammal is an animal model of the cancer or infection or is a human.

13. The method of claim 11, wherein the mammal is a human.

* * * * *

SEQUENCE LISTING

```
<160> NUMBER OF SEQ ID NOS: 10

<210> SEQ ID NO 1
<211> LENGTH: 921
<212> TYPE: DNA
<213> ORGANISM: Homo sapiens
<220> FEATURE:
<221> NAME/KEY: CDS
<222> LOCATION: (25)..(888)

<400> SEQUENCE: 1
cactctggtg gggctgctcc aggc atg cag atc cca cag gcg ccc tgg cca          51
                            Met Gln Ile Pro Gln Ala Pro Trp Pro
                             1               5 gtc gtc tgg gcg gtg cta caa ctg ggc tgg cgg cca gga tgg ttc tta         99
Val Val Trp Ala Val Leu Gln Leu Gly Trp Arg Pro Gly Trp Phe Leu
 10              15                  20                  25 gac tcc cca gac agg ccc tgg aac ccc ccc acc ttc tcc cca gcc ctg        147
Asp Ser Pro Asp Arg Pro Trp Asn Pro Pro Thr Phe Ser Pro Ala Leu
                 30                  35                  40 ctc gtg gtg acc gaa ggg gac aac gcc acc ttc acc tgc agc ttc tcc        195
Leu Val Val Thr Glu Gly Asp Asn Ala Thr Phe Thr Cys Ser Phe Ser
             45                  50                  55 aac aca tcg gag agc ttc gtg cta aac tgg tac cgc atg agc ccc agc        243
Asn Thr Ser Glu Ser Phe Val Leu Asn Trp Tyr Arg Met Ser Pro Ser
         60                  65                  70 aac cag acg gac aag ctg gcc gcc ttc ccc gag gac cgc agc cag ccc        291
Asn Gln Thr Asp Lys Leu Ala Ala Phe Pro Glu Asp Arg Ser Gln Pro
     75                  80                  85 ggc cag gac tgc cgc ttc cgt gtc aca caa ctg ccc aac ggg cgt gac        339
Gly Gln Asp Cys Arg Phe Arg Val Thr Gln Leu Pro Asn Gly Arg Asp
 90                  95                 100                 105 ttc cac atg agc gtg gtc agg gcc cgg cgc aat gac agc ggc acc tac        387
Phe His Met Ser Val Val Arg Ala Arg Arg Asn Asp Ser Gly Thr Tyr
                110                 115                 120 ctc tgt ggg gcc atc tcc ctg gcc ccc aag gcg cag atc aaa gag agc        435
Leu Cys Gly Ala Ile Ser Leu Ala Pro Lys Ala Gln Ile Lys Glu Ser
            125                 130                 135 ctg cgg gca gag ctc agg gtg aca gag aga agg gca gaa gtg ccc aca        483
Leu Arg Ala Glu Leu Arg Val Thr Glu Arg Arg Ala Glu Val Pro Thr
        140                 145                 150 gcc cac ccc agc ccc tca ccc agg cca gcc ggc cag ttc caa acc ctg        531
Ala His Pro Ser Pro Ser Pro Arg Ser Ala Gly Gln Phe Gln Thr Leu
    155                 160                 165 gtg gtt ggt gtc gtg ggc ggc ctg ctg ggc agc ctg gtg ctg cta gtc        579
Val Val Gly Val Val Gly Gly Leu Leu Gly Ser Leu Val Leu Leu Val
170                 175                 180                 185 tgg gtc ctg gcc gtc atc tgc tcc cgg gcc gca cga ggg aca ata gga        627
Trp Val Leu Ala Val Ile Cys Ser Arg Ala Ala Arg Gly Thr Ile Gly
                190                 195                 200 gcc agg cgc acc ggc cag ccc ctg aag gag gac cca tca gcc gtg cct        675
Ala Arg Arg Thr Gly Gln Pro Leu Lys Glu Asp Pro Ser Ala Val Pro
            205                 210                 215 gtg ttc tct gtg gac tat ggg gag ctg gat ttc cag tgg cga gag aag        723
```

```
Val Phe Ser Val Asp Tyr Gly Glu Leu Asp Phe Gln Trp Arg Glu Lys
            220                 225                 230 acc ccg gag ccc ccc gtg ccc tgt gtc cct gag cag acg gag tat gcc      771
Thr Pro Glu Pro Pro Val Pro Cys Val Pro Glu Gln Thr Glu Tyr Ala
    235                 240                 245 acc att gtc ttt cct agc gga atg ggc acc tca tcc ccc gcc cgc agg      819
Thr Ile Val Phe Pro Ser Gly Met Gly Thr Ser Ser Pro Ala Arg Arg
250                 255                 260                 265 ggc tca gct gac ggc cct cgg agt gcc cag cca ctg agg cct gag gat      867
Gly Ser Ala Asp Gly Pro Arg Ser Ala Gln Pro Leu Arg Pro Glu Asp
                270                 275                 280 gga cac tgc tct tgg ccc ctc tgaccggctt ccttggccac cagtgttctg cag     921
Gly His Cys Ser Trp Pro Leu
                285

<210> SEQ ID NO 2
<211> LENGTH: 288
<212> TYPE: PRT
<213> ORGANISM: Homo sapiens

<400> SEQUENCE: 2

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Ser Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
```

```
                      275              280              285

<210> SEQ ID NO 3
<211> LENGTH: 968
<212> TYPE: DNA
<213> ORGANISM: Homo sapiens
<220> FEATURE:
<221> NAME/KEY: CDS
<222> LOCATION: (59)..(793)

<400> SEQUENCE: 3
gcttcccgag gctccgcacc agccgcgctt ctgtccgcct gcagggcatt ccagaaag        58 atg agg ata ttt gct gtc ttt ata ttc atg acc tac tgg cat ttg ctg      106
Met Arg Ile Phe Ala Val Phe Ile Phe Met Thr Tyr Trp His Leu Leu
1               5                   10                  15 aac gca ttt act gtc acg gtt ccc aag gac cta tat gtg gta gag tat      154
Asn Ala Phe Thr Val Thr Val Pro Lys Asp Leu Tyr Val Val Glu Tyr
                20                  25                  30 ggt agc aat atg aca att gaa tgc aaa ttc cca gta gaa aaa caa tta      202
Gly Ser Asn Met Thr Ile Glu Cys Lys Phe Pro Val Glu Lys Gln Leu
            35                  40                  45 gac ctg gct gca cta att gtc tat tgg gaa atg gag gat aag aac att      250
Asp Leu Ala Ala Leu Ile Val Tyr Trp Glu Met Glu Asp Lys Asn Ile
        50                  55                  60 att caa ttt gtg cat gga gag gaa gac ctg aag gtt cag cat agt agc      298
Ile Gln Phe Val His Gly Glu Glu Asp Leu Lys Val Gln His Ser Ser
65                  70                  75                  80 tac aga cag agg gcc cgg ctg ttg aag gac cag ctc tcc ctg gga aat      346
Tyr Arg Gln Arg Ala Arg Leu Leu Lys Asp Gln Leu Ser Leu Gly Asn
                85                  90                  95 gct gca ctt cag atc aca gat gtg aaa ttg cag gat gca ggg gtg tac      394
Ala Ala Leu Gln Ile Thr Asp Val Lys Leu Gln Asp Ala Gly Val Tyr
                100                 105                 110 cgc tgc atg atc agc tat ggt ggt gcc gac tac aag cga att act gtg      442
Arg Cys Met Ile Ser Tyr Gly Gly Ala Asp Tyr Lys Arg Ile Thr Val
            115                 120                 125 aaa gtc aat gcc cca tac aac aaa atc aac caa aga att ttg gtt gtg      490
Lys Val Asn Ala Pro Tyr Asn Lys Ile Asn Gln Arg Ile Leu Val Val
        130                 135                 140 gat cca gtc acc tct gaa cat gaa ctg aca tgt cag gct gag ggc tac      538
Asp Pro Val Thr Ser Glu His Glu Leu Thr Cys Gln Ala Glu Gly Tyr
145                 150                 155                 160 ccc aag gcc gaa gtc atc tgg aca agc agt gac cat caa gtc ctg agt      586
Pro Lys Ala Glu Val Ile Trp Thr Ser Ser Asp His Gln Val Leu Ser
                165                 170                 175 ggt aag acc acc acc acc aat tcc aag aga gag gag aag ctt ttc aat      634
Gly Lys Thr Thr Thr Thr Asn Ser Lys Arg Glu Glu Lys Leu Phe Asn
            180                 185                 190 gtg acc agc aca ctg aga atc aac aca aca act aat gag att ttc tac      682
Val Thr Ser Thr Leu Arg Ile Asn Thr Thr Thr Asn Glu Ile Phe Tyr
        195                 200                 205 tgc act ttt agg aga tta gat cct gag gaa aac cat aca gct gaa ttg      730
Cys Thr Phe Arg Arg Leu Asp Pro Glu Glu Asn His Thr Ala Glu Leu
210                 215                 220 gtc atc cca ggt aat att ctg aat gtg tcc att aaa ata tgt cta aca      778
Val Ile Pro Gly Asn Ile Leu Asn Val Ser Ile Lys Ile Cys Leu Thr
225                 230                 235                 240 ctg tcc cct agc acc tagcatgatg tctgcctatc atagtcattc agtgattgtt      833
Leu Ser Pro Ser Thr
                245
```

```
gaataaatga atgaatgaat aacactatgt ttacaaaata tatcctaatt cctcacctcc    893
attcatccaa accatattgt tacttaataa acattcagca gatatttatg gaataaaaaa    953
aaaaaaaaaa aaaaa                                                     968
```

```
<210> SEQ ID NO 4
<211> LENGTH: 245
<212> TYPE: PRT
<213> ORGANISM: Homo sapiens

<400> SEQUENCE: 4
```

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
            245
```

```
<210> SEQ ID NO 5
<211> LENGTH: 1553
<212> TYPE: DNA
<213> ORGANISM: Homo sapiens
<220> FEATURE:
<221> NAME/KEY: CDS
<222> LOCATION: (53)..(922)

<400> SEQUENCE: 5
```

```
cgaggctccg caccagccgc gcttctgtcc gcctgcaggg cattccagaa ag atg agg    58
                                                          Met Arg
                                                          1 ata ttt gct gtc ttt ata ttc atg acc tac tgg cat ttg ctg aac gca    106
Ile Phe Ala Val Phe Ile Phe Met Thr Tyr Trp His Leu Leu Asn Ala
```

-continued

```
              5                   10                  15
ttt act gtc acg gtt ccc aag gac cta tat gtg gta gag tat ggt agc     154
Phe Thr Val Thr Val Pro Lys Asp Leu Tyr Val Val Glu Tyr Gly Ser
 20                  25                  30 aat atg aca att gaa tgc aaa ttc cca gta gaa aaa caa tta gac ctg     202
Asn Met Thr Ile Glu Cys Lys Phe Pro Val Glu Lys Gln Leu Asp Leu
 35                  40                  45                  50 gct gca cta att gtc tat tgg gaa atg gag gat aag aac att att caa     250
Ala Ala Leu Ile Val Tyr Trp Glu Met Glu Asp Lys Asn Ile Ile Gln
                 55                  60                  65 ttt gtg cat gga gag gaa gac ctg aag gtt cag cat agt agc tac aga     298
Phe Val His Gly Glu Glu Asp Leu Lys Val Gln His Ser Ser Tyr Arg
             70                  75                  80 cag agg gcc cgg ctg ttg aag gac cag ctc tcc ctg gga aat gct gca     346
Gln Arg Ala Arg Leu Leu Lys Asp Gln Leu Ser Leu Gly Asn Ala Ala
         85                  90                  95 ctt cag atc aca gat gtg aaa ttg cag gat gca ggg gtg tac cgc tgc     394
Leu Gln Ile Thr Asp Val Lys Leu Gln Asp Ala Gly Val Tyr Arg Cys
     100                 105                 110 atg atc agc tat ggt ggt gcc gac tac aag cga att act gtg aaa gtc     442
Met Ile Ser Tyr Gly Gly Ala Asp Tyr Lys Arg Ile Thr Val Lys Val
115                 120                 125                 130 aat gcc cca tac aac aaa atc aac caa aga att ttg gtt gtg gat cca     490
Asn Ala Pro Tyr Asn Lys Ile Asn Gln Arg Ile Leu Val Val Asp Pro
                 135                 140                 145 gtc acc tct gaa cat gaa ctg aca tgt cag gct gag ggc tac ccc aag     538
Val Thr Ser Glu His Glu Leu Thr Cys Gln Ala Glu Gly Tyr Pro Lys
             150                 155                 160 gcc gaa gtc atc tgg aca agc agt gac cat caa gtc ctg agt ggt aag     586
Ala Glu Val Ile Trp Thr Ser Ser Asp His Gln Val Leu Ser Gly Lys
         165                 170                 175 acc acc acc acc aat tcc aag aga gag gag aag ctt ttc aat gtg acc     634
Thr Thr Thr Thr Asn Ser Lys Arg Glu Glu Lys Leu Phe Asn Val Thr
     180                 185                 190 agc aca ctg aga atc aac aca aca act aat gag att ttc tac tgc act     682
Ser Thr Leu Arg Ile Asn Thr Thr Thr Asn Glu Ile Phe Tyr Cys Thr
195                 200                 205                 210 ttt agg aga tta gat cct gag gaa aac cat aca gct gaa ttg gtc atc     730
Phe Arg Arg Leu Asp Pro Glu Glu Asn His Thr Ala Glu Leu Val Ile
                 215                 220                 225 cca gaa cta cct ctg gca cat cct cca aat gaa agg act cac ttg gta     778
Pro Glu Leu Pro Leu Ala His Pro Pro Asn Glu Arg Thr His Leu Val
             230                 235                 240 att ctg gga gcc atc tta tta tgc ctt ggt gta gca ctg aca ttc atc     826
Ile Leu Gly Ala Ile Leu Leu Cys Leu Gly Val Ala Leu Thr Phe Ile
         245                 250                 255 ttc cgt tta aga aaa ggg aga atg atg gat gtg aaa aaa tgt ggc atc     874
Phe Arg Leu Arg Lys Gly Arg Met Met Asp Val Lys Lys Cys Gly Ile
     260                 265                 270 caa gat aca aac tca aag aag caa agt gat aca cat ttg gag gag acg     922
Gln Asp Thr Asn Ser Lys Lys Gln Ser Asp Thr His Leu Glu Glu Thr
275                 280                 285                 290 taatccagca ttggaacttc tgatcttcaa gcagggattc tcaacctgtg gtttaggggt     982
tcatcggggc tgagcgtgac aagaggaagg aatgggcccg tgggatgcag gcaatgtggg    1042
acttaaaagg cccaagcact gaaaatggaa cctggcgaaa gcagaggagg agaatgaaga    1102
aagatggagt caaacaggga gcctggaggg agaccttgat actttcaaat gcctgagggg    1162
ctcatcgacg cctgtgacag ggagaaagga tacttctgaa caaggagcct ccaagcaaat    1222
```

-continued

```
catccattgc tcatcctagg aagacgggtt gagaatccct aatttgaggg tcagttcctg    1282
cagaagtgcc ctttgcctcc actcaatgcc tcaatttgtt ttctgcatga ctgagagtct    1342
cagtgttgga acgggacagt atttatgtat gagttttcc tatttatttt gagtctgtga    1402
ggtcttcttg tcatgtgagt gtggttgtga atgatttctt ttgaagatat attgtagtag    1462
atgttacaat tttgtcgcca aactaaactt gctgcttaat gatttgctca catctagtaa    1522
aacatggagt atttgtaaaa aaaaaaaaa a                                    1553
```

<210> SEQ ID NO 6
<211> LENGTH: 290
<212> TYPE: PRT
<213> ORGANISM: Homo sapiens

<400> SEQUENCE: 6

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290
```

-continued

```
<210> SEQ ID NO 7
<211> LENGTH: 819
<212> TYPE: DNA
<213> ORGANISM: Homo sapiens
<220> FEATURE:
<221> NAME/KEY: CDS
<222> LOCATION: (1)..(819)

<400> SEQUENCE: 7 atg atc ttc ctc ctg cta atg ttg agc ctg gaa ttg cag ctt cac cag      48
Met Ile Phe Leu Leu Leu Met Leu Ser Leu Glu Leu Gln Leu His Gln
1               5                   10                  15 ata gca gct tta ttc aca gtg aca gtc cct aag gaa ctg tac ata ata      96
Ile Ala Ala Leu Phe Thr Val Thr Val Pro Lys Glu Leu Tyr Ile Ile
                20                  25                  30 gag cat ggc agc aat gtg acc ctg gaa tgc aac ttt gac act gga agt     144
Glu His Gly Ser Asn Val Thr Leu Glu Cys Asn Phe Asp Thr Gly Ser
            35                  40                  45 cat gtg aac ctt gga gca ata aca gcc agt ttg caa aag gtg gaa aat     192
His Val Asn Leu Gly Ala Ile Thr Ala Ser Leu Gln Lys Val Glu Asn
        50                  55                  60 gat aca tcc cca cac cgt gaa aga gcc act ttg ctg gag gag cag ctg     240
Asp Thr Ser Pro His Arg Glu Arg Ala Thr Leu Leu Glu Glu Gln Leu
65                  70                  75                  80 ccc cta ggg aag gcc tcg ttc cac ata cct caa gtc caa gtg agg gac     288
Pro Leu Gly Lys Ala Ser Phe His Ile Pro Gln Val Gln Val Arg Asp
                85                  90                  95 gaa gga cag tac caa tgc ata atc atc tat ggg gtc gcc tgg gac tac     336
Glu Gly Gln Tyr Gln Cys Ile Ile Ile Tyr Gly Val Ala Trp Asp Tyr
                100                 105                 110 aag tac ctg act ctg aaa gtc aaa gct tcc tac agg aaa ata aac act     384
Lys Tyr Leu Thr Leu Lys Val Lys Ala Ser Tyr Arg Lys Ile Asn Thr
            115                 120                 125 cac atc cta aag gtt cca gaa aca gat gag gta gag ctc acc tgc cag     432
His Ile Leu Lys Val Pro Glu Thr Asp Glu Val Glu Leu Thr Cys Gln
        130                 135                 140 gct aca ggt tat cct ctg gca gaa gta tcc tgg cca aac gtc agc gtt     480
Ala Thr Gly Tyr Pro Leu Ala Glu Val Ser Trp Pro Asn Val Ser Val
145                 150                 155                 160 cct gcc aac acc agc cac tcc agg acc cct gaa ggc ctc tac cag gtc     528
Pro Ala Asn Thr Ser His Ser Arg Thr Pro Glu Gly Leu Tyr Gln Val
                165                 170                 175 acc agt gtt ctg cgc cta aag cca ccc cct ggc aga aac ttc agc tgt     576
Thr Ser Val Leu Arg Leu Lys Pro Pro Pro Gly Arg Asn Phe Ser Cys
            180                 185                 190 gtg ttc tgg aat act cac gtg agg gaa ctt act ttg gcc agc att gac     624
Val Phe Trp Asn Thr His Val Arg Glu Leu Thr Leu Ala Ser Ile Asp
        195                 200                 205 ctt caa agt cag atg gaa ccc agg acc cat cca act tgg ctg ctt cac     672
Leu Gln Ser Gln Met Glu Pro Arg Thr His Pro Thr Trp Leu Leu His
    210                 215                 220 att ttc atc ccc tcc tgc atc att gct ttc att ttc ata gcc aca gtg     720
Ile Phe Ile Pro Ser Cys Ile Ile Ala Phe Ile Phe Ile Ala Thr Val
225                 230                 235                 240 ata gcc cta aga aaa caa ctc tgt caa aag ctg tat tct tca aaa gac     768
Ile Ala Leu Arg Lys Gln Leu Cys Gln Lys Leu Tyr Ser Ser Lys Asp
                245                 250                 255 aca aca aaa aga cct gtc acc aca aca aag agg gaa gtg aac agt gct     816
Thr Thr Lys Arg Pro Val Thr Thr Thr Lys Arg Glu Val Asn Ser Ala
                260                 265                 270 atc                                                                 819
Ile
```

Ile

<210> SEQ ID NO 8
<211> LENGTH: 273
<212> TYPE: PRT
<213> ORGANISM: Homo sapiens

<400> SEQUENCE: 8

```
Met Ile Phe Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Ser Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile
```

<210> SEQ ID NO 9
<211> LENGTH: 1437
<212> TYPE: DNA
<213> ORGANISM: Homo sapiens

<400> SEQUENCE: 9

```
atgataagga agaagaggaa gcgaagcgcg ccccccggcc catgccgcag ccacgggccc      60
agacccgcca cggcgcccgc gccgccgccc tcgccggagc ccacgagacc tgcatggacg     120
ggcatgggct tgagagcagc accttccagc gccgccgctg ccgccgccga ggttgagcag     180
cgccgcagcc ccgggctctg cccccccgccg ctggagctgc tgctgctgct gctgttcagc     240
```

```
ctcgggctgc tccacgcagg tgactgccaa cagccagccc aatgtcgaat ccagaaatgc    300
accacggact tcgtgtccct gacttctcac ctgaactctg ccgttgacgg ctttgactct    360
gagttttgca aggccttgcg tgcctatgct ggctgcaccc agcgaacttc aaaagcctgc    420
cgtggcaacc tggtatacca ttctgccgtg ttgggtatca gtgacctcat gagccagagg    480
aattgttcca aggatggacc cacatcctct accaaccccg aagtgaccca tgatccttgc    540
aactatcaca gccacgctgg agccagggaa cacaggagag gggaccagaa ccctcccagt    600
tacctttttt gtggcttgtt tggagatcct cacctcagaa ctttcaagga taacttccaa    660
acatgcaaag tagaaggggc ctggccactc atagataata attatctttc agttcaagtg    720
acaaacgtac ctgtggtccc tggatccagt gctactgcta caaataagat cactattatc    780
ttcaaagccc accatgagtg tacagatcag aaagtctacc aagctgtgac agatgacctg    840
ccggccgcct ttgtggatgg caccaccagt ggtggggaca gcgatgccaa gagcctgcgt    900
atcgtggaaa gggagagtgg ccactatgtg gagatgcacg cccgctatat agggaccaca    960
gtgtttgtgc ggcaggtggg tcgctacctg acccttgcca tccgtatgcc tgaagacctg   1020
gccatgtcct acgaggagag ccaggacctg cagctgtgcg tgaacggctg ccccctgagt   1080
gaacgcatcg atgacgggca gggccaggtg tctgccatcc tgggacacag cctgcctcgc   1140
acctccttgg tgcaggcctg gcctggctac acactggaga ctgccaacac tcaatgccat   1200
gagaagatgc agtgaagga catctatttc agtcctgtg tcttcgacct gctcaccact   1260
ggtgatgcca actttactgc cgcagcccac agtgccttgg aggatgtgga ggccctgcac   1320
ccaaggaagg aacgctggca catttccccc agcagtggca atgggactcc ccgtggaggc   1380
agtgatttgt ctgtcagtct aggactcacc tgcttgatcc ttatcgtgtt tttgtag      1437
```

<210> SEQ ID NO 10
<211> LENGTH: 478
<212> TYPE: PRT
<213> ORGANISM: Homo sapiens

<400> SEQUENCE: 10

```
Met Ile Arg Lys Lys Arg Lys Arg Ser Ala Pro Gly Pro Cys Arg
1               5                   10                  15

Ser His Gly Pro Arg Pro Ala Thr Ala Pro Ala Pro Pro Ser Pro
                20                  25                  30

Glu Pro Thr Arg Pro Ala Trp Thr Gly Met Gly Leu Arg Ala Ala Pro
                35                  40                  45

Ser Ser Ala Ala Ala Ala Ala Glu Val Glu Gln Arg Arg Ser Pro
        50                  55                  60

Gly Leu Cys Pro Pro Leu Glu Leu Leu Leu Leu Leu Phe Ser
65                  70                  75                  80

Leu Gly Leu Leu His Ala Gly Asp Cys Gln Gln Pro Ala Gln Cys Arg
                85                  90                  95

Ile Gln Lys Cys Thr Thr Asp Phe Val Ser Leu Thr Ser His Leu Asn
                100                 105                 110

Ser Ala Val Asp Gly Phe Asp Ser Glu Phe Cys Lys Ala Leu Arg Ala
        115                 120                 125

Tyr Ala Gly Cys Thr Gln Arg Thr Ser Lys Ala Cys Arg Gly Asn Leu
        130                 135                 140

Val Tyr His Ser Ala Val Leu Gly Ile Ser Asp Leu Met Ser Gln Arg
145                 150                 155                 160

Asn Cys Ser Lys Asp Gly Pro Thr Ser Ser Thr Asn Pro Glu Val Thr
```

```
                165                 170                 175
His Asp Pro Cys Asn Tyr His Ser His Ala Gly Ala Arg Glu His Arg
            180             185             190

Arg Gly Asp Gln Asn Pro Pro Ser Tyr Leu Phe Cys Gly Leu Phe Gly
        195             200             205

Asp Pro His Leu Arg Thr Phe Lys Asp Asn Phe Gln Thr Cys Lys Val
    210             215             220

Glu Gly Ala Trp Pro Leu Ile Asp Asn Asn Tyr Leu Ser Val Gln Val
225             230             235             240

Thr Asn Val Pro Val Pro Gly Ser Ser Ala Thr Ala Thr Asn Lys
            245             250             255

Ile Thr Ile Ile Phe Lys Ala His His Glu Cys Thr Asp Gln Lys Val
            260             265             270

Tyr Gln Ala Val Thr Asp Asp Leu Pro Ala Ala Phe Val Asp Gly Thr
            275             280             285

Thr Ser Gly Gly Asp Ser Asp Ala Lys Ser Leu Arg Ile Val Glu Arg
        290             295             300

Glu Ser Gly His Tyr Val Glu Met His Ala Arg Tyr Ile Gly Thr Thr
305             310             315             320

Val Phe Val Arg Gln Val Gly Arg Tyr Leu Thr Leu Ala Ile Arg Met
                325             330             335

Pro Glu Asp Leu Ala Met Ser Tyr Glu Glu Ser Gln Asp Leu Gln Leu
            340             345             350

Cys Val Asn Gly Cys Pro Leu Ser Glu Arg Ile Asp Asp Gly Gln Gly
            355             360             365

Gln Val Ser Ala Ile Leu Gly His Ser Leu Pro Arg Thr Ser Leu Val
        370             375             380

Gln Ala Trp Pro Gly Tyr Thr Leu Glu Thr Ala Asn Thr Gln Cys His
385             390             395             400

Glu Lys Met Pro Val Lys Asp Ile Tyr Phe Gln Ser Cys Val Phe Asp
                405             410             415

Leu Leu Thr Thr Gly Asp Ala Asn Phe Thr Ala Ala His Ser Ala
            420             425             430

Leu Glu Asp Val Glu Ala Leu His Pro Arg Lys Glu Arg Trp His Ile
        435             440             445

Phe Pro Ser Ser Gly Asn Gly Thr Pro Arg Gly Gly Ser Asp Leu Ser
    450             455             460

Val Ser Leu Gly Leu Thr Cys Leu Ile Leu Ile Val Phe Leu
465             470             475
```